(12) United States Patent
Rehage

(10) Patent No.: US 9,624,437 B2
(45) Date of Patent: Apr. 18, 2017

(54) PLANT-BASED COMPOSITIONS AND USES THEREOF

(71) Applicant: GreenStract, LLC, New York, NY (US)

(72) Inventor: Peter Rehage, South Lake Tahoe, CA (US)

(73) Assignee: GreenStract, LLC, New York, NY (US)

( * ) Notice: Subject to any disclaimer, the term of this patent is extended or adjusted under 35 U.S.C. 154(b) by 0 days.

(21) Appl. No.: 15/187,472

(22) Filed: Jun. 20, 2016

(65) Prior Publication Data

US 2016/0298037 A1  Oct. 13, 2016

Related U.S. Application Data

(63) Continuation of application No. 13/842,173, filed on Mar. 15, 2013, now Pat. No. 9,371,489.

(51) Int. Cl.
*C09K 8/68* (2006.01)
*B09C 1/02* (2006.01)
(Continued)

(52) U.S. Cl.
CPC ............ *C10G 1/045* (2013.01); *B08B 3/04* (2013.01); *B09C 1/02* (2013.01); *B09C 1/08* (2013.01); *C02F 1/00* (2013.01); *C05D 9/02* (2013.01); *C05F 11/00* (2013.01); *C05G 1/00* (2013.01); *C05G 3/0076* (2013.01); *C09C 1/02* (2013.01); *C09K 3/22* (2013.01); *C09K 8/62* (2013.01); *C09K 8/68* (2013.01); *C09K 17/14* (2013.01); *C09K 17/40* (2013.01); *C11D 3/042* (2013.01); *C11D 3/044* (2013.01); *C11D 3/046* (2013.01); *C11D 3/2003* (2013.01); *C11D 3/2079* (2013.01); *C11D 3/2082* (2013.01); *C11D 3/2086* (2013.01); *C11D 3/2096* (2013.01);
(Continued)

(58) Field of Classification Search
None
See application file for complete search history.

(56) References Cited

U.S. PATENT DOCUMENTS 3,396,104 A  8/1968 Miller
3,878,110 A  4/1975 Miller et al.
(Continued)

FOREIGN PATENT DOCUMENTS

EP  0146395 A2  6/1985
EP  0238946  11/1991
(Continued)

OTHER PUBLICATIONS

Supplementary European Search Report for European Application No. 12842757.2, mailed May 26, 2015, 8 pages.
(Continued)

*Primary Examiner* — Wayne Langel
(74) *Attorney, Agent, or Firm* — Cooley LLP

(57) ABSTRACT

The present invention relates to compositions comprising a plant material and methods for using the same. The methods include extracting or removing a substance from a substrate, or remediating a substrate from a substance. The substance can comprise a hydrocarbon-containing substance, a protein, lipid, wax, fatty acid or fatty alcohol, or a combination thereof.

46 Claims, 27 Drawing Sheets

(51) Int. Cl.

| | | |
|---|---|---|
| B09C 1/08 | (2006.01) | |
| B08B 3/04 | (2006.01) | |
| C10G 1/04 | (2006.01) | |
| C05F 11/00 | (2006.01) | |
| C09K 8/62 | (2006.01) | |
| C11D 3/382 | (2006.01) | |
| C02F 1/00 | (2006.01) | |
| C09K 3/22 | (2006.01) | |
| C09K 17/14 | (2006.01) | |
| C09K 17/40 | (2006.01) | |
| C05D 9/02 | (2006.01) | |
| C05G 1/00 | (2006.01) | |
| C05G 3/00 | (2006.01) | |
| C11D 3/04 | (2006.01) | |
| C11D 3/20 | (2006.01) | |
| C11D 3/43 | (2006.01) | |
| C11D 7/06 | (2006.01) | |
| C11D 7/08 | (2006.01) | |
| C11D 7/10 | (2006.01) | |
| C11D 7/26 | (2006.01) | |
| C11D 7/44 | (2006.01) | |
| C11D 7/50 | (2006.01) | |
| C11D 11/00 | (2006.01) | |
| C09C 1/02 | (2006.01) | |
| C07C 7/00 | (2006.01) | |

(52) U.S. Cl.
CPC .......... *C11D 3/382* (2013.01); *C11D 3/43* (2013.01); *C11D 7/06* (2013.01); *C11D 7/08* (2013.01); *C11D 7/10* (2013.01); *C11D 7/261* (2013.01); *C11D 7/44* (2013.01); *C11D 7/5004* (2013.01); *C11D 11/0035* (2013.01); *C07C 7/00* (2013.01); *Y02E 50/343* (2013.01); *Y02T 50/678* (2013.01); *Y02W 30/47* (2015.05)

(56) References Cited

U.S. PATENT DOCUMENTS

| | | |
|---|---|---|
| 4,119,435 A | 10/1978 | Nakao et al. |
| 4,645,831 A | 2/1987 | Lawhon |
| 4,811,787 A | 3/1989 | Navratil et al. |
| 4,997,469 A | 3/1991 | Moore |
| 5,021,077 A | 6/1991 | Moore |
| 5,021,247 A | 6/1991 | Moore |
| 5,138,038 A | 8/1992 | Katayama et al. |
| 5,185,174 A | 2/1993 | Sawhill |
| 5,207,941 A | 5/1993 | Kroner et al. |
| 5,209,851 A | 5/1993 | Hume et al. |
| 5,330,005 A | 7/1994 | Card et al. |
| 5,344,574 A | 9/1994 | Hume et al. |
| 5,376,183 A | 12/1994 | Gatt et al. |
| 5,399,350 A | 3/1995 | Potter |
| 5,401,413 A | 3/1995 | Gatt et al. |
| 5,439,055 A | 8/1995 | Card et al. |
| 5,501,275 A | 3/1996 | Card et al. |
| 5,510,112 A | 4/1996 | Gatt et al. |
| 5,513,705 A | 5/1996 | Djabbarah et al. |
| 5,514,412 A | 5/1996 | McArdle |
| 5,542,474 A | 8/1996 | Djabbarah et al. |
| 5,542,987 A | 8/1996 | Gatt et al. |
| 5,589,195 A | 12/1996 | Potter |
| 5,591,473 A | 1/1997 | McArdle |
| 5,626,658 A | 5/1997 | McArdle |
| 5,645,880 A | 7/1997 | McArdle |
| 5,747,416 A | 5/1998 | McArdle |
| 5,798,446 A | 8/1998 | Neumuller |
| 5,942,123 A | 8/1999 | McArdle |
| 6,063,367 A | 5/2000 | Manzo et al. |
| 6,172,011 B1 | 1/2001 | Card et al. |
| 6,197,199 B1 | 3/2001 | McArdle |
| 6,261,629 B1 | 7/2001 | Mazza et al. |
| 6,342,885 B1 | 1/2002 | Knittel et al. |
| 6,395,198 B1 | 5/2002 | McArdle |
| 6,432,885 B1 | 8/2002 | Vollmer |
| 6,509,301 B1 | 1/2003 | Vollmer |
| 6,610,831 B1 | 8/2003 | McInnis et al. |
| 7,071,153 B2 | 7/2006 | Lewis et al. |
| 7,220,709 B1 | 5/2007 | Qu et al. |
| 7,410,937 B2 | 8/2008 | Grascha et al. |
| 7,563,473 B2 | 7/2009 | Scanlin et al. |
| 7,612,027 B2 | 11/2009 | Grasha et al. |
| 7,708,799 B2 | 5/2010 | Grech et al. |
| 7,776,124 B2 | 8/2010 | Binder et al. |
| 7,811,352 B2 | 10/2010 | Binder et al. |
| 7,963,720 B2 | 6/2011 | Hoag et al. |
| 7,976,241 B2 | 7/2011 | Hoag et al. |
| 7,992,656 B2 | 8/2011 | Dusterhoft et al. |
| 8,057,682 B2 | 11/2011 | Hoag et al. |
| 8,206,062 B2 | 6/2012 | Hoag et al. |
| 8,278,260 B2 | 10/2012 | Saint Victor |
| 8,283,304 B2 | 10/2012 | Saint Victor |
| 8,541,356 B2 | 9/2013 | Saint Victor |
| 8,637,284 B2 | 1/2014 | Medoff |
| 8,728,779 B2 | 5/2014 | Medoff |
| 8,735,178 B2 | 5/2014 | Mohan et al. |
| 8,741,373 B2 | 6/2014 | Bromley et al. |
| 8,778,860 B2 | 7/2014 | Saint Victor |
| 8,835,142 B2 | 9/2014 | Medoff |
| 8,841,101 B2 | 9/2014 | Medoff |
| 8,877,472 B2 | 11/2014 | Medoff |
| 8,980,602 B2 | 3/2015 | Medoff |
| 9,078,461 B2 | 7/2015 | Medoff |
| 9,149,045 B2 | 10/2015 | Lee et al. |
| 9,371,489 B2 | 6/2016 | Rehage |
| 9,388,343 B2 | 7/2016 | Rehage |
| 2003/0109679 A1 | 6/2003 | Green et al. |
| 2005/0245420 A1 | 11/2005 | Lewis et al. |
| 2006/0134045 A1 | 6/2006 | Cao et al. |
| 2007/0054031 A1 | 3/2007 | Liu |
| 2007/0092629 A1 | 4/2007 | Scanlin et al. |
| 2007/0131010 A1 | 6/2007 | Binder et al. |
| 2007/0172914 A1 | 7/2007 | Slabbekoorn et al. |
| 2007/0184159 A1 | 8/2007 | Paustian et al. |
| 2007/0207255 A1 | 9/2007 | Crank |
| 2008/0227677 A1 | 9/2008 | Grascha et al. |
| 2009/0093406 A1 | 4/2009 | Hwang et al. |
| 2009/0098261 A1 | 4/2009 | Park et al. |
| 2009/0291189 A1 | 11/2009 | Zacherl et al. |
| 2010/0092414 A1 | 4/2010 | Karagianni et al. |
| 2010/0101605 A1 | 4/2010 | Saint Victor |
| 2010/0124583 A1 | 5/2010 | Medoff |
| 2010/0136148 A1 | 6/2010 | Saint Victor |
| 2010/0144582 A1 | 6/2010 | Saint Victor |
| 2010/0144584 A1 | 6/2010 | Saint Victor |
| 2010/0181110 A1 | 7/2010 | Harr |
| 2010/0227381 A1 | 9/2010 | Hoag et al. |
| 2011/0005773 A1 | 1/2011 | Dusterhoft et al. |
| 2011/0091283 A1 | 4/2011 | Suib et al. |
| 2012/0016026 A1 | 1/2012 | Bromley et al. |
| 2012/0055873 A1 | 3/2012 | Hoag et al. |
| 2012/0141571 A1 | 6/2012 | Lee et al. |
| 2012/0319042 A1 | 12/2012 | Hoag et al. |
| 2013/0288935 A1 | 10/2013 | Rehage |
| 2014/0110177 A1 | 4/2014 | Harr |
| 2014/0135252 A1 | 5/2014 | Jones et al. |
| 2014/0227242 A1 | 8/2014 | Bromley et al. |
| 2014/0260466 A1 | 9/2014 | Rehage |
| 2014/0271928 A1 | 9/2014 | Rehage |
| 2014/0332212 A1 | 11/2014 | Ayers et al. |
| 2014/0348982 A1 | 11/2014 | Medoff |
| 2015/0099681 A1 | 4/2015 | Rehage |
| 2015/0342224 A1 | 12/2015 | Medoff |
| 2015/0353974 A1 | 12/2015 | Medoff |

FOREIGN PATENT DOCUMENTS

| | | |
|---|---|---|
| EP | 0466524 | 8/1994 |
| EP | 0523184 | 12/1998 |
| JP | 2005-177740 | * 7/2005 |

(56) References Cited

FOREIGN PATENT DOCUMENTS

| WO | WO 94/19942 | 9/1994 |
|---|---|---|
| WO | WO 95/13997 | 5/1995 |
| WO | WO 96/03054 | 2/1996 |
| WO | WO 96/35858 | 11/1996 |
| WO | WO 98/23567 | 6/1998 |
| WO | WO 02/34070 | 5/2002 |
| WO | WO 02/062154 | 8/2002 |
| WO | WO 2005/074704 | 8/2005 |
| WO | WO 2007/092131 | 8/2007 |
| WO | WO 2007/126779 | 11/2007 |
| WO | WO 2009/114145 | 9/2009 |
| WO | WO 2009/155350 | 12/2009 |
| WO | WO 2010/078528 | 7/2010 |
| WO | WO 2011/011456 | 1/2011 |
| WO | WO 2013/062782 | 5/2013 |
| WO | WO 2014/145057 | 9/2014 |

OTHER PUBLICATIONS

Office Action for U.S. Appl. No. 13/784,475, mailed Apr. 20, 2015, 13 pages.
Office Action for U.S. Appl. No. 13/784,475, mailed Nov. 17, 2015, 18 pages.
Claims filed on Oct. 19, 2015, in connection with U.S. Appl. No. 13/784,475, 5 pages.
International Search Report and Written Opinion for International Application No. PCT/US2012/059770, mailed Dec. 24, 2012, 13 pages.
Claims filed on Feb. 12, 2016, in connection with U.S. Appl. No. 14/982,859, 5 pages.
Office Action for U.S. Appl. No. 13/842,173, mailed May 28, 2015, 6 pages.
Office Action for U.S. Appl. No. 13/842,173, mailed Nov. 23, 2015, 6 pages.
Claims filed on Feb. 12, 2016, in connection with U.S. Appl. No. 13/842,173, 15 pages.
Office Action for U.S. Appl. No. 14/214,474, mailed Aug. 28, 2015, 13 pages.
Claims filed on Feb. 12, 2016, in connection with U.S. Appl. No. 14/214,474, 3 pages.
International Search Report and Written Opinion for International Application No. PCT/US2014/029711, mailed Aug. 12, 2014, 11 pages.
Office Action for U.S. Appl. No. 14/512,635, mailed Aug. 27, 2015, 5 pages.
Claims filed on Feb. 12, 2016, in connection with U.S. Appl. No. 14/512,635, 6 pages.
Lewis, R. J., Hawley's Condensed Chemical Dictionary, Fourteenth Edition, John Wiley & Sons, Inc., pp. 14, 15, 29, 117, 901 and 977 (2001).
Masliyah, J. et al., "Understanding water-based bitumen extraction from Athabasca oil sands," The Canadian Journal of Chemical Engineering, 82(4):628-654 (2004).
Wayback Machine, How Oil and Gas Wells Are Drilled Horizontally [online], <URL: https://web.archive.org/web/20080614023235/http:/www.energyindustryphotos.com/how_oil_and_gas_wells_are_drille.htm>, Jun. 14, 2008 [Retrieved on May 11, 2016], 3 pages.
Katewongsa, P. et al, "Development of liquid soap containing methanolic extract of cork tree stamen," Research Journal of Pharmaceutical, Biological and Chemical Sciences, 3(1):384-389 (Jan.-Mar. 2012).

* cited by examiner

FIG. 27
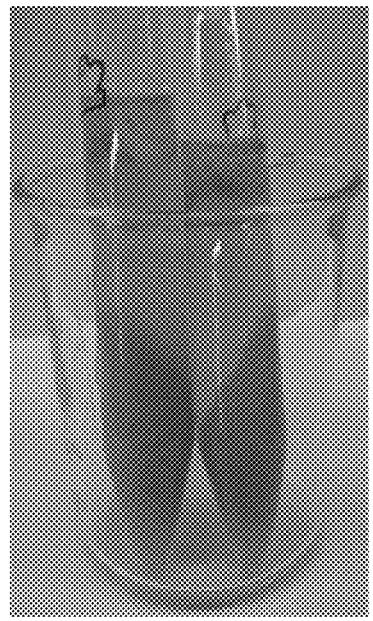
FIG. 28A    FIG. 28B
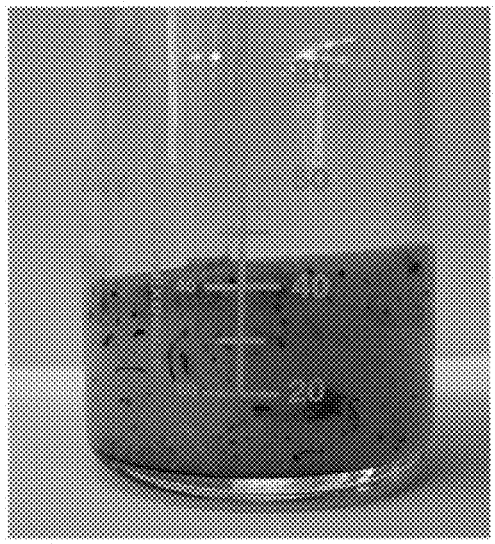 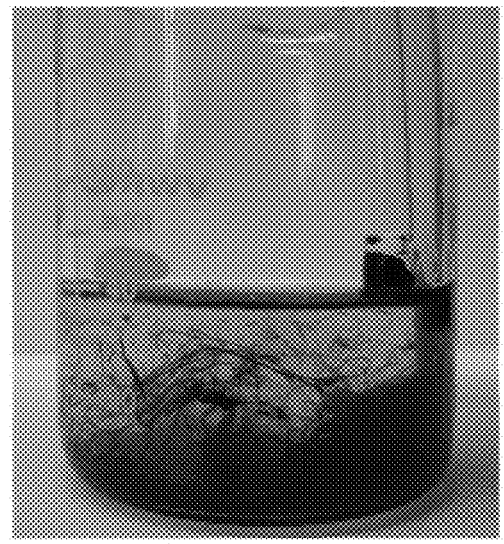

FIG. 39
FIG. 40A       FIG. 40B
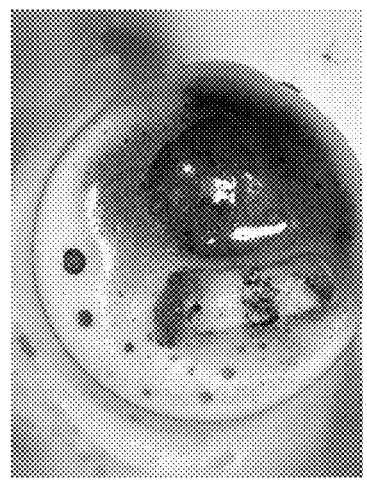  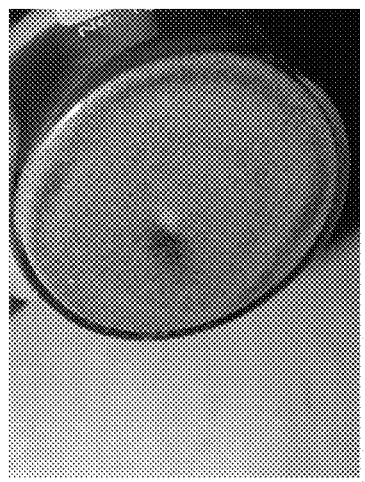
FIG. 41A       FIG. 41B
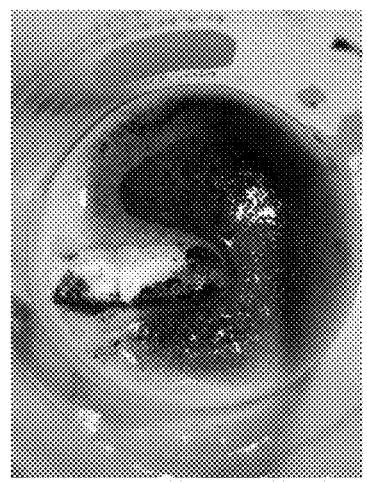  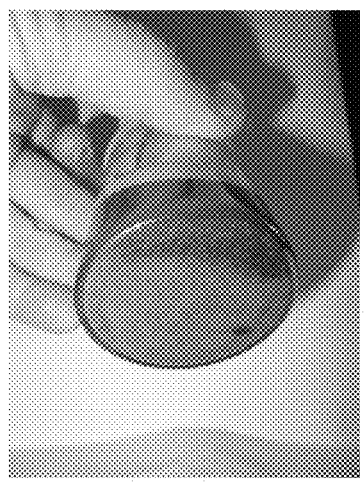

FIG. 42
FIG. 43A FIG. 43B
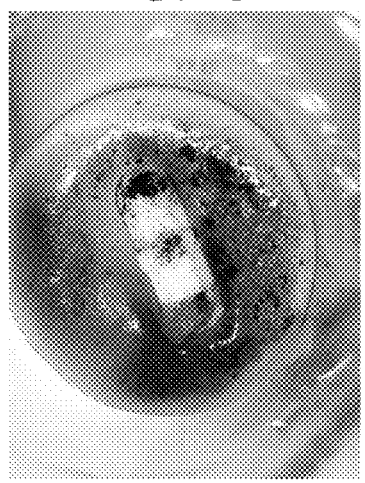 
FIG. 44A FIG. 44B
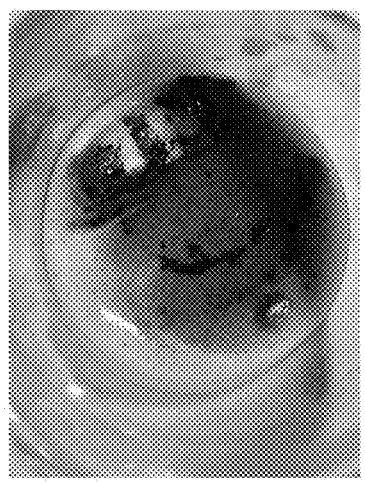 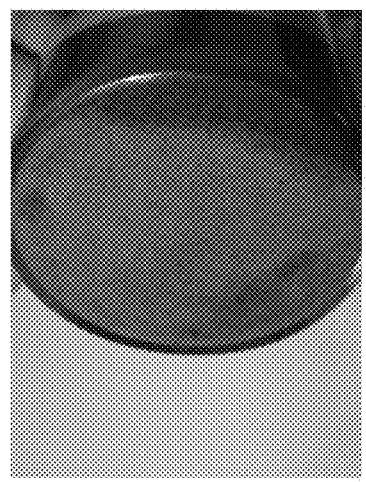

FIG. 45
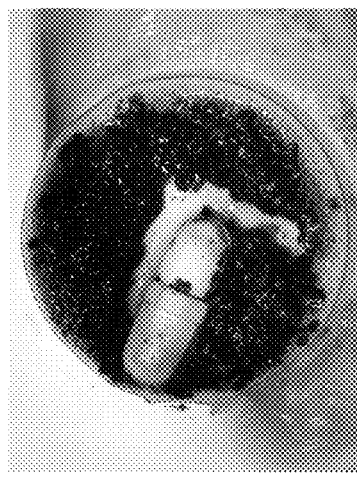
FIG. 46A     FIG. 46B
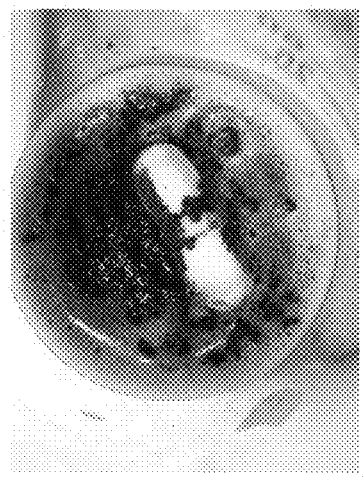 
FIG. 47A     FIG. 47B
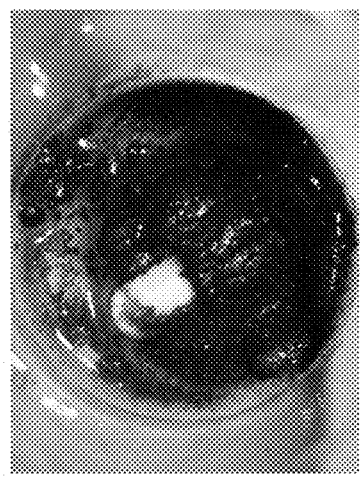 

FIG. 48
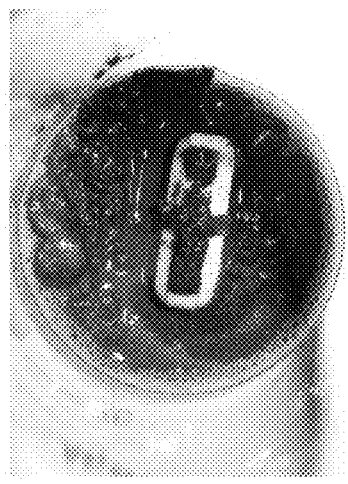
FIG. 49A  FIG. 49B
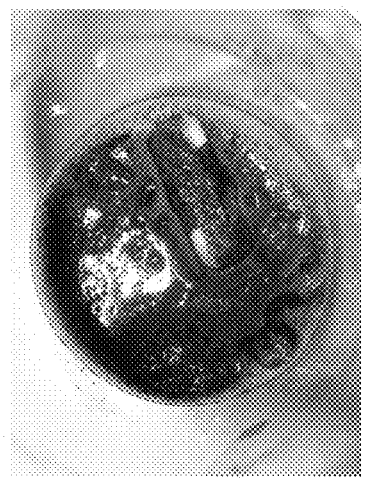 
FIG. 50A  FIG. 50B
 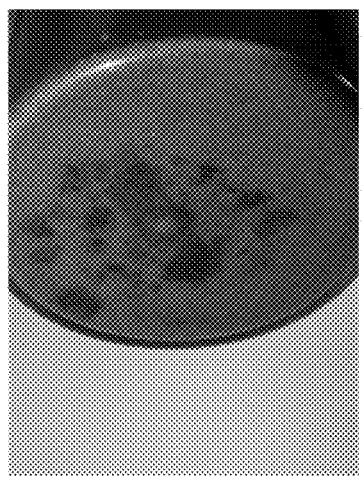

PLANT-BASED COMPOSITIONS AND USES THEREOF

CROSS-REFERENCE TO RELATED APPLICATIONS

This application is a continuation of U.S. application Ser. No. 13/842,173, filed on Mar. 15, 2013, which is incorporated herein by reference in its entirety.

FIELD OF THE INVENTION

The present invention relates generally to compositions comprising plant material and methods for using the same. The methods include extracting a substance from a substrate and remediating a substrate from a substance, wherein the substance can comprise a protein, lipid, wax, fatty acid, fatty alcohol, hydrocarbon-containing substance, or a combination thereof. The methods also include providing a skin benefit; controlling, preventing, or treating oily or greasy hair; promoting hair growth; treating or preventing a periodontal disease, dental plaque or dental decay; and accelerating wound healing with the compositions provided herein. Methods of using the composition for purifying a mixture comprising an alcohol, inhibiting agglomeration of a granulated product, inducing plant growth, and preventing erosion is also provided.

BACKGROUND

World petroleum supplies are finite. Thus, as world petroleum demand has increased (84,337 M bpd worldwide in 2009; US Energy Information Administration), easily accessible reserves have been depleted. Furthermore, much of the world's proven conventional petroleum reserves are located in regions which are politically unstable. Accordingly, supplies of petroleum from such regions might be uncertain since production of petroleum or the transportation of petroleum products from such regions might be interrupted.

Bituminous sands, colloquially known as oil sands or tar sands, are a type of unconventional petroleum deposit. The sands typically comprise naturally occurring mixtures of sand, clay, water, and a dense and viscous form of petroleum known as bitumen. Oil sands reserves have only recently been considered to be part of the world's oil reserves, as higher oil prices and new technology enable oil sands to be profitably extracted and refined. Thus, oil sands are now a viable alternative to conventional crude oil. Oil sands might represent as much as two-thirds of the world's total "liquid" hydrocarbon resources, with at least 1.7 trillion recoverable BOE (barrel of oil equivalent) in the Canadian Athabasca oil sands alone.

Extra-heavy oil and bitumen flow very slowly, if at all, toward oil-producing wells under normal reservoir conditions. Accordingly, in certain oil recovery operations from oil sands, the oil is made to flow into wells by using in situ techniques that reduce its viscosity by injecting steam, solvents, or hot air into the sands. These processes typically use large amounts of water and require large amounts of energy relative to conventional oil extraction. Further, typical extraction processes applied to oil sands generate significantly higher amounts of greenhouse gases per barrel relative to the production of conventional oils due to the increased energy requirements for recovery of oil from oil sands.

In other oil sand mining operations, where oil sands are relatively close to the earth's surface, surface mining has been used to extract the oil contained therein. After removing the overburden (the soil covering the oil sands), the sands are mechanically excavated and transported to a refining facility.

In one surface-mining method, after excavation, hot water and caustic soda (NaOH) are added to the sand. The resultant slurry is piped to the extraction plant where it is agitated and oil is skimmed off the mixture. The combination of hot water, sodium hydroxide, a flocculant and agitation generally releases bitumen from the oil sand, and the oil floats to the top of separation vessels where it is separated. Then, the separated oil is further treated to remove residual water and fine solids before subsequent processing to convert the heavy oil to usable products.

Such conventional processes to extract oil from oil sands also employ mixing the oil sand with high pH water, and then aerating the resultant mixture with air to produce froth (see, e.g., Masliyah, J.; Zhou, Z. J.; Xu, Z.; Czarnecki, J.; Hamza, H.: "Understanding water-based bitumen extraction from Athabasca oil sands." *The Canadian Journal of Chemical Engineering* 2004, 82, (4), 628-654). A slurry of high pH water and oil sand is placed in a primary separation cell (PSC). Agitation and introduction of air assists in separating oil from the oil sand, and creates a froth in which the oil is entrained. The froth is removed, deaerated, and sent to feed tanks for further treatment. The remaining sand, comprising residual oil not removed in the PSC, is treated as "middlings" or as bottoms using the same process for extracting oil from oil sands in the PSC (i.e., high pH water and aeration). The froth from these subsequent processes is recycled to the PSC. The overall enhancement of oil from the oil in the froth is approximately 60% by mass over the iterative removal steps.

About two tons of oil sands are required to produce one barrel (roughly ⅛ of a ton) of oil. After oil extraction, the spent sand and other materials are typically transported back to the mine for disposal. However, even with improved extraction processes, up to 10% of the oil in the oil sands can be left in the resultant tailings. Thus, the process is inefficient. The tailings can contain significant amounts of oil and other pollutants which must be disposed of in an environmentally sound manner. In conventional oil sand mining operations, this has resulted in large lagoons containing high levels of oil and other pollutants. Accordingly, there is a need for improved compositions and methods for extraction of oil from oil sands that are more efficient (e.g., can remove higher amounts of oil), use less energy, and produce tailings that are environmentally benign.

In addition, in conventional oil production processes, methods of enhancing oil recovery are known. These include, but are not limited to hydraulic fracturing of rock formations containing hydrocarbon deposits. In hydraulic fracturing operations, a fluid (e.g., water) which can comprise various additives (e.g., acids, rheology modifiers, detergents, gels, gas, proppant, etc.) is introduced into a rock formation under high pressure to fracture the rock formation. Such fracturing of a hydrocarbon-bearing rock formation effectively increases the surface area of rock exposed to a wellbore (i.e., along the fracture faces), and accordingly, allows more hydrocarbon to flow into the well bore. However, the viscosity of the oils contained in the formation can limit the utility of hydraulically fracturing rock formations which contain heavy oils. That is, if the viscosity of the oil is too high, increasing the surface area of the formation exposed to the well bore along the fracture might not significantly increase production rates. Accordingly, there is a need for hydraulic fracturing fluids which can enhance total oil recovery or increase oil production rates.

In addition, remediation of environmentally compromised sites (e.g., hazardous waste sites) is an ongoing challenge. For example, there are many sites where hydrocarbons (e.g., crude oil, coal tar, creosote, refined oil products) have been spilled or discharged into the environment. Such discharges can result in contamination of soil or water, and can contaminate groundwater supplies. Accordingly, such contaminated sites or waters (e.g., rivers, streams, ponds and harbors) require remediation to extract contaminants.

There are several known remediation technologies. One method comprises excavation of contaminated soil. However, remediation by excavation has traditionally been a "dig and haul" process, wherein contaminated soils are excavated and disposed of in landfills or destroyed by thermal treatments such as incineration. In the case of landfill disposal of contaminated soil, the problem of soil contamination is not resolved as the soil is relocated and moved to another location. In the case of thermal desorption, the hydrocarbon or other pollutants can be destroyed, but typically produces a large carbon footprint, which, in and of itself, is not an environmentally friendly process, since energy is required and greenhouse gases are produced.

Chemical treatment (e.g., oxidation) has also been utilized in the remediation of contaminated soil. This process comprises excavation of the contaminated soil, followed by chemical treatment to chemically modify or degrade the pollutants to potentially less toxic or hazardous forms. However, such methods can require large quantities of specialized chemicals to oxidize the contaminants, and can be ineffective at oxidizing certain pollutants.

Another remediation method comprises injection of a material into the soil to sequester contaminants, with a goal of immobilizing them and preventing them from migrating. For example, stabilization/solidification (S/S) is a remediation or treatment technology that relies on the reaction between a binder and soil to stop, prevent or reduce the mobility of contaminants. Stabilization comprises the addition of liquid or solid materials to contaminated soil to produce more chemically stable constituents. Solidification comprises the addition of liquid or solid reagents to a contaminated material to impart physical, for example, dimensional stability, so that they are constrained in a solid product and to reduce mobility of the contaminants. However, such methods might not be desirable since over time, the solids can break down or degrade, releasing the hydrocarbons or other pollutants back into the environment.

Accordingly, there is a need for cost-effective methods for extracting contaminants (e.g., hydrocarbons) from soils and other substrates at environmentally compromised or contaminated sites and for sequestering contaminants in situ in a cost effective manner.

There is also a need for improved compositions and methods for extracting or removing other undesirable substances from substrates, such as the removal of a protein, lipid, wax, fatty acid or fatty alcohol from a substrate such as fabric, skin or hair. For example, skin sebum contains bulky oils such as long chain fatty esters and triglycerides and can be difficult to remove. Sebum generally comprises a complex mixture of triglycerides, wax esters, squalene, sterol esters and free sterols produced by sebocytes (cells of the sebaceous glands in the skin) and secreted to the skin surface. An excessive amount of sebum on the skin can lead to undesirable skin effects. Similarly, an excessive amount of oils or grease in hair can lead to an undesirable appearance. Thus, there is a need for novel compositions and methods to remove excessive oils from the skin and hair.

The present invention meets these needs and provides related advantages.

SUMMARY OF THE INVENTION

In one embodiment, the present invention provides aqueous compositions comprising: about 1 wt % to about 50 wt % of plant material; 0% to about 20 wt % of a polysaccharide; 0% to about 10 wt % of an alcohol; 0% to about 25 wt % of a base; 0% to about 30 wt % of a salt; 0% to about 10 wt % of an acid; 0% to about 30 wt % of an additive; 0% to about 30 wt % of a sugar; and about 10 wt % to about 95 wt % of water; wherein the aqueous compositions have a pH of from about 9 to about 13, and wherein the plant material is hemp seed, soybean, or combinations thereof.

In another embodiment, the present invention provides extractants comprising: about 0.1 wt % to about 2 wt % of plant material; 0% to about 2 wt % of a polysaccharide; 0% to about 1 wt % of an alcohol; 0% to about 10 wt % of a base; 0% to about 30 wt % of a salt; 0% to about 10 wt % of an acid; 0% to about 30 wt % of an additive; 0% to about 30 wt % of a sugar; and about 90 wt % to about 99.9 wt % water; wherein the plant material is hemp seed, soybean, or combinations thereof.

In another embodiment, the present invention provides substantially anhydrous compositions comprising: about 20 wt % to about 99.9 wt % of plant material; 0 to about 20 wt % of a polysaccharide; 0% to about 1 wt % of an alcohol; 0% to about 30 wt % of a base; 0% to about 50 wt % of a salt; 0% to about 10 wt % of an acid; 0% to about 30 wt % of an additive; and 0% to about 10 wt % water; 0% to about 30 wt % of a sugar; wherein the plant material is hemp seed, soybean, or combinations thereof.

The present invention further provides articles, where the article is a bandage, absorptive dental roll, tampon, sanitary napkin, diaper, body urinal, underarm perspiration pad, breast pad, disposable hat band, wiping cloth, tissue wipe, premoistened towelette, mattress pad, undersheet, surgical dressing, toilet paper or facial tissue and wherein the article contains a Composition of the Invention.

The present invention also provides a method for extracting a substance from a substrate and comprises contacting the substrate with a Composition of the Invention under conditions effective for extracting at least some of the substance from the substrate.

In another aspect, the present invention also provides a method for remediating a substrate from a substance, comprising contacting the substrate with a Composition of the Invention under conditions effective for remediating the substrate from the substance.

Also provided herein is a method for providing a skin benefit. In one embodiment, the method for providing a skin benefit comprises applying to the skin of a subject in need thereof an effective amount of a Composition of the Invention.

In another aspect, the present invention provides a method for controlling, preventing, or treating oily or greasy hair, or promoting hair growth comprising applying to the scalp or hair of a subject in need thereof an effective amount of a Composition of the Invention.

In still another aspect, the present invention provides a method for treating or preventing a periodontal disease, dental plaque or dental decay comprising administering to the oral cavity of a subject in need thereof an effective amount of a Composition of the Invention.

In another aspect, the present invention provides a method for treating a wound comprising contacting a wound of a subject with a Composition of the Invention under conditions effective for accelerating wound healing.

The present invention also provides a method of purifying a mixture comprising an alcohol, including purifying a mixture comprising an alcohol and an impurity.

In another aspect, the present invention provides a method of purifying a mixture comprising an impurity, comprising contacting the mixture with a Composition of the Invention under conditions effective for removing at least some of the impurity from the mixture.

In another aspect, the present invention provides a method of inhibiting agglomeration of a granulated product. In one embodiment, the method comprises contacting the granulated product with a Composition of the Invention under conditions effective for inhibiting agglomeration of the granulated product.

In another aspect, the present invention provides a method for inducing plant growth. In one embodiment, the method comprises contacting a plant seed, plant root, or soil in which the plant seed or root is present in with a Composition of the Invention under conditions effective for inducing growth of the plant.

In another aspect, the present invention provides a method for making a plant fertilizer, wherein the method comprises admixing with sand or soil a Composition of the Invention.

The present invention also provides methods for preventing soil, sand or road surface erosion, comprising applying to the soil, sand, or road surface beach a Composition of the Invention under conditions effective to prevent erosion of the soil, sand or road surface.

The present compositions (each being a "Composition of the Invention") and methods, and advantages thereof, are further illustrated by the following non-limiting detailed description and Examples.

BRIEF DESCRIPTION OF THE DRAWINGS

FIG. 11 shows stringers of oil separating from the oil sand.

FIG. 12 shows stringers of oil separating from the oil sand.

FIG. 15 is a photograph of "free" oil sticking to the glass of the beaker in which the oil sand and extractant were stirred, after decanting the extractant liquid comprising some extracted oil into a second beaker. FIG. 16 is a photograph showing the remaining sand and oil in the beaker in which the oil sand and extractant were stirred after decanting the extractant liquid comprising some extracted oil into the second beaker.

FIG. 27 is a photograph showing an aliquot of a pH 12.7 hemp-based composition, prepared by acid treatment of hemp, after centrifugation.

FIG. 28A is a photograph showing Monarch oil after addition to a 10 wt % solution of the uncentrifuged hemp-based composition of Example 29.

FIG. 28B is a photograph showing coal tar after addition to a 10 wt % solution of the centrifuged hemp-based composition of Example 29.

FIGS. 39, 40A-B and 41A-B are photographs showing the extraction of coal tar from coal tar sand in a 10 wt % solution of the composition of Example 37 over approximately 3 hours and 20 minutes of stirring.

FIGS. 42, 43A-B and 44A-B are photographs showing the extraction of coal tar from coal tar sand in a 10 wt % solution of the composition of Example 38 over approximately 3 hours and 20 minutes of stirring.

FIGS. 45, 46A-B and 47A-B are photographs showing the extraction of Athabasca oil from Athabasca oil sand in a 10 wt % solution of the composition of Example 35 over approximately 3 hours and 20 minutes of stirring.

FIGS. 48, 49A-B and 50A-B are photographs showing the extraction of Athabasca oil from Athabasca oil sand in a 10 wt % solution of the composition of Example 36 over approximately 3 hours and 20 minutes of stirring.

DETAILED DESCRIPTION OF THE INVENTION

Figure 1A:
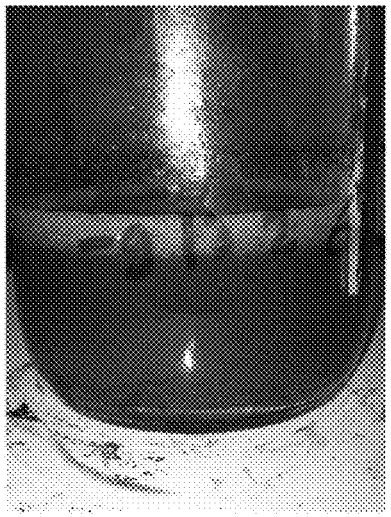
FIGS. 1A-B are photographs showing a side view of the vessel containing the mixture of Example 3 after 60 min of stirring, then briefly allowing the mixture to settle (FIG. 1A), and a top view of the inside of the vessel after decanting the supernatant (FIG. 1B), also after 60 min of stirring.

The word 'about' when immediately preceding a numerical value means a range of plus or minus 10% of that value, e.g., "about 50" means 45 to 55, "about 25,000" means 22,500 to 27,500, etc. Furthermore, the phrases "less than about" a value or "greater than about" a value should be understood in view of the definition of the term "about" provided herein.

Compositions of the Invention

The compositions of the present invention (each being a "Composition of the Invention") may be aqueous, an extractant, or substantially anhydrous. The Compositions of the Invention may further comprise a cosmetically acceptable vehicle or a pharmaceutically acceptable carrier, vehicle, or excipient.

Aqueous Compositions

In one embodiment, the present invention provides aqueous compositions comprising: about 1 wt % to about 50 wt % of plant material; 0% to about 20 wt % of a polysaccharide; 0% to about 10 wt % of an alcohol; 0% to about 25 wt % of a base; 0% to about 30 wt % of a salt; 0% to about 10 wt % of an acid; 0% to about 30 wt % of an additive; 0% to about 30 wt % of a sugar; and about 10 wt % to about 95 wt % of water; wherein the aqueous composition has a pH of from about 9 to about 13, and wherein the plant material is hemp seed, soybean, or combinations thereof.

In another embodiment, the present invention provides aqueous compositions comprising about 0.1 wt % to about 2 wt % of plant material; 0% to about 2 wt % of a polysaccharide; 0% to about 1 wt % of an alcohol; 0% to about 10 wt % of a base; 0% to about 10 wt % of a salt; 0% to about 10 wt % of an acid; 0% to about 10 wt % of an additive; and about 90 wt % to about 99.9 wt % water. In one embodiment, the composition comprises about 0.1 wt % to about 2 wt % of plant material; 0% to about 2 wt % of a polysaccharide; 0% to about 1 wt % of an alcohol; 0% to about 10 wt % of a base; 0% to about 10 wt % of a salt; 0% to about 10 wt % of an acid; 0% to about 10 wt % of an additive; and about 90 wt % to about 99.9 wt % water. In yet another embodiment, the composition comprises about 20 wt % to about 99.9 wt % of plant material; 0 to about 20 wt % of a polysaccharide; 0% to about 1 wt % of an alcohol; 0% to about 15 wt % of a base; 0% to about 10 wt % of a salt; 0% to about 10 wt % of an acid; 0% to about 10 wt % of an additive; and 0% to about 10 wt % water.

In other embodiments, the aqueous compositions comprise from about 1 to about 30 wt % of plant material and 0 to about 10 wt % of a polysaccharide. In certain embodiments, the aqueous compositions comprise from about 1 to about 10 wt % of plant material and 0 to about 5 wt % of a polysaccharide. In still other embodiments, the aqueous compositions comprise from about 1 to about 5 wt % of plant material and 0 to about 1 wt % of a polysaccharide. In some embodiments, the aqueous compositions do not comprise a polysaccharide other than that present in or derived from the plant material. In other embodiments, the aqueous compositions do not comprise a polysaccharide.

Polysaccharides include oligomeric or polymeric sugars comprising at least three monomeric units. The monomeric units may be the same or different, and may include monosaccharides or disaccharides. Polysaccharides which are useful in the present aqueous composition are typically water-soluble, e.g., soluble in water or water-alcohol solutions. In general, the polysaccharides are plant-derived polysaccharides, including related materials such as pectins. Examples of polysaccharides that are useful for the present aqueous compositions include, but are not limited to, water-soluble cellulose derivatives, seaweed polysaccharides such as alginate and carrageenan, seed mucilaginous polysaccharides, complex plant exudate polysaccharides such as gum arabic, tragacanth, guar gum, pectin, ghatti gum and the like, and microbially synthesized polysaccharides such as xanthan gum, or mixtures of such polysaccharides. In certain embodiments, the polysaccharide is guar gum, pectin, gum arabic and mixtures thereof. In some embodiments, the polysaccharide is a synthetic polysaccharide such as synthetic guar. In one embodiment, the polysaccharide is guar gum. In some embodiments, the present aqueous compositions do not comprise one or more of the aforementioned polysaccharides other than that present in or derived from the plant material. In other embodiments, the present aqueous compositions do not comprise one or more of the aforementioned polysaccharides.

The polysaccharide can be present in the aqueous compositions in an amount ranging from 0 to about 20 wt % (e.g., 0 to about 0.5 wt %, about 0.5 wt % to about 1 wt %, about 1 wt % to about 2 wt %, about 2 wt % to about 3 wt %, about 3 wt % to about 4 wt %, about 4 wt % to about 5 wt %, about 5 wt % to about 6 wt %, about 6 wt % to about 7 wt %, about 7 wt % to about 8 wt %, about 8 wt % to about 9 wt %, about 9 wt % to about 10 wt %, about 10 wt % to about 11 wt %, about 11 wt % to about 12 wt %, about 12 wt % to about 13 wt %, about 13 wt % to about 14 wt %, about 14 wt % to about 15 wt %, about 15 wt % to about 16 wt %, about 16 wt % about 17 wt %, about 17 wt % to about 18 wt %, about 18 wt % to about 19 wt %, about 19 wt % to about 20 wt %, or any other value or range of values therein). In some embodiments, the polysaccharide is present in an amount of from about 0.1 wt % to about 5 wt %. In other embodiments, the present aqueous compositions do not comprise a polysaccharide (i.e., 0 wt %).

Similarly, plant material useful in the present aqueous compositions can be those from any plant. The plant material can include any part of the plant, e.g., trunk, stems, seeds, roots, leaves, branches, bark, flowers, nuts, sprouts, or any other part of a plant. In some embodiments, the plant material comprises plant protein. In some embodiments, the plant proteins are prolamines. In certain embodiments, the plant is a cereal plant. Suitable cereal plants include, but are not limited to, corn, rice, wheat, barley, sorghum, millet, rye, triticale, fonio, buckwheat, spelt, quinoa, flax, or mixtures thereof. In other embodiments, the plant material is lentils (e.g., green, yellow, black), soybean, hemp seed, chia, grass, wheat grass and barley (e.g., pearl, groat). In some embodiments, the plant is cotton, and the plant material is cotton seeds. In some embodiments, the plant is flax, and the plant material is flax seeds. In some embodiments, the plant is wheat, and the plant material is wheat germ. In some embodiments, the plant material is corn gluten meal. In still other embodiments, the corn gluten meal comprises a protein, and the protein is gluten. In other embodiments, the gluten is corn gluten.

In some embodiments, the plant is hemp, and the plant material is hemp seeds. In some embodiments, the hemp seeds are hulled hemp seeds. In some embodiments, the plant is soy, and the plant material is soybean. In some embodiments, soybean is partially sprouted.

In some embodiments, the plant material has a protein content of from about 5 wt % to about 100 wt % (e.g., 5 to about 10 wt %, about 10 wt % to about 15 wt %, about 15 wt % to about 20 wt %, about 20 wt % to about 25 wt %, about 25 wt % to about 30 wt %, about 30 wt % to about 35 wt %, about 35 wt % to about 40 wt %, about 40 wt % to about 45 wt %, about 45 wt % to about 50 wt %, about 50 wt % to about 55 wt %, about 55 wt % to about 60 wt %, about 60 wt % to about 65 wt %, about 65 wt % to about 70 wt %, about 70 wt % to about 75 wt %, about 75 wt % to about 80 wt %, about 80 wt % to about 85 wt %, about 85 wt % to about 90 wt %, about 90 wt % about 95 wt %, about 95 wt % to about 100 wt %, or any other value or range of values therein) of the plant material.

In some embodiments, the present aqueous compositions comprise a plant protein as measured by Biuret assay (as described herein), in an amount ranging from about 0.1 ppt (part per thousand) to about 100 ppt (e.g., from about 0.1 ppt to about 0.2 ppt, from about 0.2 ppt to about 0.3 ppt, from about 0.3 ppt to about 0.4 ppt, from about 0.4 ppt to about 0.5 ppt, from about 0.5 ppt to about 0.6 ppt, from about 0.6 ppt to about 0.7 ppt, from about 0.7 ppt to about 0.8 ppt, from about 0.8 ppt to about 0.9 ppt, from about 0.9 ppt to about 1.0 ppt, from about 1 ppt to about 5 ppt, from about 5 ppt to about 10 ppt, from about 10 ppt to about 15 ppt, from about 15 ppt to about 20 ppt, from about 20 ppt to about 25 ppt, from about 25 ppt to about 30 ppt, from about 30 ppt to about 35 ppt, from about 35 ppt to about 40 ppt, from about 40 ppt to about 45 ppt, from about 45 ppt to about 50 ppt, from about 50 ppt to about 55 ppt, from about 55 ppt to about 60 ppt, from about 60 ppt to about 65 ppt, from about 65 ppt to about 70 ppt, from about 70 ppt to about 75 ppt, from about 75 ppt to about 80 ppt, from about 80 ppt to about 85 ppt, from about 85 ppt to about 90 ppt, from about 90 ppt to about 95 ppt, from about 95 ppt to about 100 ppt, or any other value or range of values therein) of the aqueous composition.

Prolamine is a cereal-derived protein that is typically soluble in dilute aqueous alcohol solutions. Examples of suitable prolamines that are useful in the present aqueous compositions include, but are not limited to, corn-derived prolamine (also referred to as zein), barley-derived prolamine or hordein, wheat-derived prolamine or gliadin, or corn gluten. Zein is extractable from corn or maize.

Zein can be extracted from corn gluten by physical separation means or chemical separation means. In one embodiment, the zein has a molecular weight of about 20,000 to about 35,000 Da. In another embodiment, the zein has a molecular weight of from about 19,000 Da to about 22,000 Da.

In certain embodiments, the plant protein is separated from plant material. For example, the plant material can be combined with a solvent or solvent blend to extract plant protein from the plant material. In certain embodiments, the plant material can be combined with a solvent or solvent blend to separate the plant protein from the plant material. Suitable solvents can include water, or an organic solvent, in the absence or presence of water. Suitable organic solvents include, but are not limited to, $C_1$ to $C_4$ alcohols such as methanol, ethanol, n-propanol and i-propanol, n-butanol, sec-butanol, isobutanol and tert-butanol; glycols such as ethylene glycol, propylene glycol, polyethylene glycol; glycol ethers; amine solvents such as butylamine; aminoalcohols such as ethanolamine, diethanolamine, diisopropanolamine; ketone-containing solvents such as acetone, acetic acid and acetamide; aromatic alcohols such as benzyl alcohol; and mixtures thereof.

In other embodiments, the plant material can be combined with a solvent or solvent blend and then can be treated with acid or base to separate plant protein from the plant material. Thus, in some embodiments, the plant material of the present aqueous compositions is an acidified plant material. An acidified plant material is plant material which has been contacted with an acid. For example, a plant material can be contacted with an acid or a solution comprising an acid to afford the acidified plant material. The acid can be an inorganic or organic acid. In some embodiments, the inorganic acid is hydrochloric acid, sulfuric acid or nitric acid. In some embodiments, the organic acid is a $C_1$ to $C_{20}$ organic acid such as formic acid, citric acid, malic acid, adipic acid, tannic acid, lactic acid, ascorbic acid, acetic acid, fumaric acid, and mixtures thereof. In one embodiment, the acid is citric acid. In some embodiments, the acid is aqueous.

In other embodiments, the plant material of the present aqueous compositions is a basified plant material. A basified plant material is plant material which has been contacted with a base. For example, a plant material can be contacted with a base or a solution comprising a base to afford the basified plant material. The base can be an inorganic or organic base. In some embodiments, the inorganic base is an alkali metal or alkaline earth metal compound such as sodium hydroxide, lithium hydroxide, potassium hydroxide, sodium carbonate, potassium carbonate, sodium bicarbonate, potassium bicarbonate, magnesium carbonate and calcium carbonate. In some embodiments, the organic base is an a $C_1$-$C_6$ mono, di or trialkyl amine pyridine or triethylamine. Other suitable bases include ammonium hydroxide and ammonia. In some embodiments, the base is aqueous.

In some embodiments, the acidified plant material is subsequently basified, such that its pH, or the pH of a Composition of the Invention comprising acidified plant material, is raised. The pH of the acidified plant material after being basified, or of a Composition of the Invention comprising acidified plant material after being basified, can be acidic, neutral or basic. Acidified plant material that is subsequently basified can be reacidified. The pH of the reacidified plant material, or of a Composition of the Invention comprising reacidified plant material, can be acidic, neutral or basic.

In some embodiments, the basified plant material is subsequently acidified, such that its pH, or the pH of a Composition of the Invention comprising basified plant material, is lowered. The pH of the basified plant material after being acidified, or of a Composition of the Invention comprising basified plant material after being acidified, can be acidic, neutral or basic. Basified plant material that is subsequently acidified can be rebasified. The pH of the rebasified plant material, or of a Composition of the Invention comprising rebasified plant material, can be acidic, neutral or basic.

Suitable acids and bases for separation of plant protein from plant material are those as described herein which are useful in a preparing a Composition of the Invention. In some embodiments, the pH of the mixture of the plant material and solvent may be adjusted to from about 2 to about 14 (e.g., from about 2 to about 3, from about 3 to about 4, from about 4 to about 5, from about 5 to about 6, from about 6 to about 7, from about 7 to about 8, from about 8 to about 9, from about 9 to about 10, from about 10 to about 11, from about 11 to about 12, from about 12 to about 13, from about 13 to about 14, or any other value or range of values therein). The mixture of the plant material and solvent, which can further comprise an acid or base, may be agitated (e.g., stirring, mixing).

In some embodiments, the plant material or plant protein may be reduced in size prior to use in the present aqueous compositions. For example, the plant material or plant protein may be ground, chopped, pulverized, milled or macerated to reduce the size of the plant material, to enable the dissolution, suspension or admixture of the plant material or protein in the present aqueous compositions. For example, the plant material or plant protein may be ground, chopped or macerated to provide particulate sizes (e.g., length, width or average diameter) ranging from about 0.1 mm to about 1 cm (e.g., from about 0.1 mm to about 0.2 mm, from about 0.2 mm to about 0.3 mm, from about 0.3 mm to about 0.4 mm, from about 0.4 mm to about 0.5 mm, from about 0.5 mm to about 0.6 mm, from about 0.6 mm to about 0.7 mm, from about 0.7 mm to about 0.8 mm, from about 0.8 mm to about 0.9 mm, from about 0.9 mm to about 1 mm, from about 1 mm to about 2 mm, from about 2 mm to about 3 mm, from about 3 mm to about 4 mm, from about 4 mm to about 5 mm, from about 5 mm to about 6 mm, from about 6 mm to about 7 mm, from about 7 mm to about 8 mm, from about 8 mm to about 9 mm, from about 9 mm to about 1 cm, or any other value or range of values therein).

The mixture comprising the plant material can be admixed, optionally with agitation, for a period of about 10 minutes, about 20 minutes, about 30 minutes, about 40 minutes, about 50 minutes, about 1 hour, about 2 hours, about 3 hours, about 4 hours, or any other value or range of values therein or thereabove) and at a temperature of from about 5° C. to about 100° C. (e.g., about 5° C. to about 10° C., about 10° C. to about 15° C., about 15° C. to about 20° C., about 20° C. to about 25° C., about 25° C. to about 30° C., about 30° C. to about 35° C., about 35° C. to about 40° C., about 40° C. to about 45° C., about 45° C. to about 50° C., about 50° C. to about 55° C., about 55° C. to about 60° C., about 60° C. to about 65° C., about 65° C. to about 70° C., about 70° C. to about 75° C., about 75° C. to about 80° C., about 80° C. to about 85° C., about 85° C. to about 90° C., about 90° C. to about 95° C., about 95° C. to about 100° C., or any other value or range of values therein). The solvent and pH can be selected to suspend or solubilize protein present in the plant material. The remaining components (e.g., cellulosic material) from the plant material can precipitate out of solution, and the plant protein can then be separated by decanting the supernatant or by filtration.

In other embodiments, the plant protein may be obtained as a pre-separated material. For example, zein extracted from corn may be obtained commercially from, e.g., Chemieliva Pharmaceutical Co., Ltd., HBC Chem. Inc., Matrix Marketing GMBH, and Spectrum Chemical Mfg. Corp.

In some embodiments, the plant material is present in the aqueous compositions in an amount ranging from about 1 to 50 wt % (e.g., about 1 to about 2 wt %, about 2 wt % to about 3 wt %, about 3 wt % to about 4 wt %, about 4 wt % to about 5 wt %, about 5 wt % to about 6 wt %, about 6 wt % to about 7 wt %, about 7 wt % to about 8 wt %, about 8 wt % to about 9 wt %, about 9 wt % to about 10 wt %, about 10 wt % to about 11 wt %, about 11 wt % to about 12 wt %, about 12 wt % to about 13 wt %, about 13 wt % to about 14 wt %, about 14 wt % to about 15 wt %, about 15 wt % to about 20 wt %, about 20 wt % to about 25 wt %, about 25 wt % to about 30 wt %, about 30 wt % to about 35 wt %, about 35 wt % to about 40 wt %, about 40 wt % to about 45 wt %, about 45 wt % to about 50 wt %, or any other value or range of values therein) of the aqueous composition. In some embodiments, the plant material is present in an amount of from about 1 wt % to about 30 wt %. In certain embodiments, the plant material is present in an amount of from about 1 wt % to about 10 wt %. In other embodiments, the plant material is present in an amount of from about 1 wt % to about 5 wt %.

The present aqueous compositions can further comprise an acid or a base. The acid or base is useful for adjusting the pH of the aqueous compositions. For example, the acid or base is useful for adjusting the pH of the present aqueous compositions to a pH of about 1 to about 14 (e.g., from about 1 to about 2, from about 2 to about 2, from about 3 to about 4, from about 4 to about 5, from about 5 to about 6, from about 6 to about 7, from about 7 to about 8, from about 8 to about 9, from about 9 to about 10, from about 10 to about 11, from about 11 to about 12, from about 12 to about 13, from about 13 to about 14, or any other value or range of values therein). In certain embodiments, the pH of the present aqueous composition ranges from about 3.5 to about 13; in other embodiments, from about 6.5 to about 8.5. In some embodiments, the pH is about 13; in other embodiments, the pH is about 7.5 to about 8.4. In certain embodiments, the pH of the present aqueous composition ranges from about 5 to about 13; from about 6 to about 13; from about 7 to about 13; from about 8 to about 13; from about 9 to about 13; from about 10 to about 13; from about 11 to about 13; from about 12 to about 13.

Such pH adjustment can improve the dispersibility of the protein or polysaccharide, if present, of the present aqueous compositions. Acids useful in the present aqueous compositions include inorganic acids such as carbonic acid, sulfuric acid, or hydrochloric acid. Organic acids can alternatively be employed. Suitable organic acids include $C_1$ to $C_{20}$ organic acids such as formic acid, citric acid, malic acid, adipic acid, tannic acid, lactic acid, ascorbic acid, acetic acid, fumaric acid, and mixtures thereof. In one embodiment, the acid is citric acid.

The acid can be present in the aqueous compositions in an amount from 0 wt % to about 10 wt % (e.g., 0 to about 0.5 wt %, about 0.5 wt % to about 1 wt %, about 1 wt % to about 2 wt %, about 2 wt % to about 3 wt %, about 3 wt % to about 4 wt %, about 4 wt % to about 5 wt %, about 5 wt % to about 6 wt %, about 6 wt % to about 7 wt %, about 7 wt % to about 8 wt %, about 8 wt % to about 9 wt %, about 9 wt % to about 10 wt %, or any other value or range of values therein) of the aqueous composition. In some embodiments, the acid is present from about 0.01 wt % to about 2 wt % of the aqueous compositions. In one embodiment, the acid is present in about 0.03 wt %. In some embodiments, the aqueous compositions do not comprise an acid.

The present aqueous composition can comprise a base. Bases useful in the present aqueous compositions are organic or inorganic bases. Suitable inorganic bases include alkali metal or alkaline earth metal compounds such as sodium hydroxide, lithium hydroxide, potassium hydroxide, sodium carbonate, potassium carbonate, sodium bicarbonate, potassium bicarbonate, magnesium carbonate and calcium carbonate. Other suitable bases include ammonium hydroxide, substituted amine bases and ammonia.

The base can be present in the aqueous compositions in an amount from 0 wt % to about 25 wt % (e.g., 0 to about 0.5 wt %, about 0.5 wt % to about 1 wt %, about 1 wt % to about 2 wt %, about 2 wt % to about 3 wt %, about 3 wt % to about 4 wt %, about 4 wt % to about 5 wt %, about 5 wt % to about 6 wt %, about 6 wt % to about 7 wt %, about 7 wt % to about 8 wt %, about 8 wt % to about 9 wt %, about 9 wt % to about 10 wt %, about 10 wt % to about 11 wt %, about 11 wt % to about 12 wt %, about 12 wt % to about 13 wt %, about 13 wt % to about 14 wt %, about 14 wt % to about 15 wt %, about 15 wt % to about 16 wt %, about 16 wt % to about 17 wt %, about 17 wt % to about 18 wt %, about 18 wt % to about 19 wt %, about 19 wt % to about 20 wt %, about 20 wt % to about 21 wt %, about 21 wt % to about 22 wt %, about 22 wt % to about 23 wt %, about 23 wt % to about 24 wt %, about 24 wt % to about 25 wt %, or any other value or range of values therein). In some embodiments, the base is present from about 1 wt % to about 15 wt % of the aqueous compositions. In one embodiment, the base is present in about 7 wt %. In some embodiments, the aqueous compositions do not comprise a base.

The present aqueous compositions can also comprise a salt. Salts useful in the present aqueous compositions include organic or inorganic salts. Suitable salts include alkali or alkaline earth metal salts such as sodium chloride, sodium nitrate, potassium chloride, calcium chloride, magnesium chloride, ammonium chloride, sodium bromide, potassium bromide, calcium bromide, magnesium bromide, ammonium bromide, sodium iodide, potassium iodide, calcium iodide, magnesium iodide, ammonium iodide, sodium sulfate, potassium sulfate, calcium sulfate, magnesium sulfate, ammonium sulfate.

The salt can present in the aqueous compositions in an amount from 0 wt % to about 30 wt % (e.g., 0 to about 0.5 wt %, about 0.5 wt % to about 1 wt %, about 1 wt % to about 2 wt %, about 2 wt % to about 3 wt %, about 3 wt % to about 4 wt %, about 4 wt % to about 5 wt %, about 5 wt % to about 6 wt %, about 6 wt % to about 7 wt %, about 7 wt % to about 8 wt %, about 8 wt % to about 9 wt %, about 9 wt % to about 10 wt %, about 10 wt % to about 11 wt %, about 11 wt % to about 12 wt %, about 12 wt % to about 13 wt %, about 13 wt % to about 14 wt %, about 14 wt % to about 15 wt %, about 15 wt % to about 16 wt %, about 16 wt % to about 17 wt %, about 17 wt % to about 18 wt %, about 18 wt % to about 19 wt %, about 19 wt % to about 20 wt %, about 20 wt % to about 21 wt %, about 21 wt % to about 22 wt %, about 22 wt % to about 23 wt %, about 23 wt % to about 24 wt %, about 24 wt % to about 25 wt %, about 25 wt % to about 26 wt %, about 26 wt % to about 27 wt %, about 27 wt % to about 28 wt %, about 28 wt % to about 29 wt %, about 29 wt % to about 30 wt %, or any other value or range of values therein) of the aqueous composition. In some embodiments, the salt is present from about 0.01 wt % to about 0.05 wt % of the aqueous compositions. In some embodiments, the aqueous compositions do not comprise a salt.

The present aqueous composition can comprise a sugar. A "sugar" includes any monosaccharide or disaccharide. Sugars which are useful in the present aqueous compositions include glucose, fructose, galactose, xylose, ribose, sucrose, lactose, maltose, and trehalose.

The sugar can present in the aqueous compositions in an amount from 0 wt % to about 30 wt % (e.g., 0 to about 0.5 wt %, about 0.5 wt % to about 1 wt %, about 1 wt % to about 2 wt %, about 2 wt % to about 3 wt %, about 3 wt % to about 4 wt %, about 4 wt % to about 5 wt %, about 5 wt % to about 6 wt %, about 6 wt % to about 7 wt %, about 7 wt % to about 8 wt %, about 8 wt % to about 9 wt %, about 9 wt % to about 10 wt %, about 10 wt % to about 11 wt %, about 11 wt % to about 12 wt %, about 12 wt % to about 13 wt %, about 13 wt % to about 14 wt %, about 14 wt % to about 15 wt %, about 15 wt % to about 16 wt %, about 16 wt % to about 17 wt %, about 17 wt % to about 18 wt %, about 18 wt % to about 19 wt %, about 19 wt % to about 20 wt %, about 20 wt % to about 21 wt %, about 21 wt % to about 22 wt %, about 22 wt % to about 23 wt %, about 23 wt % to about 24 wt %, about 24 wt % to about 25 wt %, about 25 wt % to about 26 wt %, about 26 wt % to about 27 wt %, about 27 wt % to about 28 wt %, about 28 wt % to about 29 wt %, about 29 wt % to about 30 wt %, or any other value or range of values therein). In one embodiment, the aqueous composition does not comprise sugar.

The present aqueous compositions comprise water. The amount of water in the present aqueous compositions can range from about 10 to about 90 wt % (e.g., about 10 wt % to about 15 wt %, about 15 wt % to about 20 wt %, about 20 wt % to about 25 wt %, about 25 wt % to about 30 wt %, about 30 wt % to about 35 wt %, about 35 wt % to about 40 wt %, about 40 wt % to about 45 wt %, about 45 wt % to about 50 wt %, about 50 wt % to about 55 wt %, about 55 wt % to about 60 wt %, about 60 wt % to about 65 wt %, about 65 wt % to about 70 wt %, about 70 wt % to about 75 wt %, about 75 wt % to about 80 wt %, about 80 wt % to about 85 wt %, about 85 wt % to about 90 wt %, or any other value or range of values therein). In certain embodiments, the aqueous compositions comprise from about 80 wt % to about 90 wt % water. In one embodiment, the aqueous compositions comprise about 69 wt % water.

The present aqueous compositions can further comprise an organic solvent, in the absence or presence of water. Suitable organic solvents include, but are not limited to, $C_1$ to $C_4$ alcohols such as methanol, ethanol, n-propanol and i-propanol, n-butanol, sec-butanol, isobutanol and tert-butanol. Alternatively glycols such as ethylene glycol, propylene glycol and polyethylene glycol, and ketone-containing solvents such as acetone can be employed. In certain embodiments, the aqueous organic solvent is ethanol or i-propanol. In one embodiment, the aqueous compositions comprise water and an alcohol; in another embodiment, water and ethanol or i-propanol.

The amount of organic solvent, if present, can be selected based on factors such as its miscibility in water, if present, and the amount of protein. The organic solvent can be present in the aqueous compositions in an amount ranging from 0 wt % to about 10 wt % (e.g., 0 wt % to about 1 wt %, about 1 wt % to about 2 wt %, about 2 wt % to about 3 wt %, about 3 wt % to about 4 wt %, about 4 wt % to about 5 wt %, about 5 wt % to about 6 wt %, about 6 wt % to about 7 wt %, about 7 wt % to about 8 wt %, about 8 wt % to about 9 wt %, about 9 wt % to about 10 wt %, or any other value or range of values therein) of the aqueous composition. In certain embodiments, the organic solvent is present in an amount of about 2.5 wt %. In some embodiments, the aqueous compositions do not comprise an organic solvent.

The present aqueous compositions can also comprise one or more other additives. Suitable additives include, but are not limited to, detergents, as surface tension modifiers, flocculants, dispersants, rheology modifiers, emulsifiers, surfactants and solvents. Illustrative additives are polysorbates, oils (e.g., canola oil, vegetable oils, etc.) In some embodiments, the present aqueous compositions comprise lime (e.g., quick lime, slaked lime, $Ca(OH)_2$, Type-S hydrated lime). In certain embodiments, the lime is Type-S hydrated lime. The additive(s) can be present in the aqueous compositions in amounts ranging from 0 to about 30 wt % (e.g., 0 to about 0.5 wt %, about 0.5 wt % to about 1 wt %, about 1 wt % to about 2 wt %, about 2 wt % to about 3 wt %, about 3 wt % to about 4 wt %, about 4 wt % to about 5 wt %, about 5 wt % to about 6 wt %, about 6 wt % to about 7 wt %, about 7 wt % to about 8 wt %, about 8 wt % to about 9 wt %, about 9 wt % to about 10 wt %, about 10 wt % to about 11 wt %, about 11 wt % to about 12 wt %, about 12 wt % to about 13 wt %, about 13 wt % to about 14 wt %, about 14 wt % to about 15 wt %, about 15 wt % to about 16 wt %, about 16 wt % to about 17 wt %, about 17 wt % to about 18 wt %, about 18 wt % to about 19 wt %, about 19 wt % to about 20 wt %, about 20 wt % to about 21 wt %, about 21 wt % to about 22 wt %, about 22 wt % to about 23 wt %, about 23 wt % to about 24 wt %, about 24 wt % to about 25 wt %, about 25 wt % to about 26 wt %, about 26 wt % to about 27 wt %, about 27 wt % to about 28 wt %, about 28 wt % to about 29 wt %, about 29 wt % to about 30 wt %, or any other value or range of values therein) of the aqueous composition. In certain embodiments, the additive is Type-S hydrated lime and is present in an amount of about 0.5 wt %. In some embodiments, the aqueous compositions do not comprise an additive. In some embodiments, the aqueous compositions do not comprise lime. In some embodiments, the aqueous compositions do not comprise S type hydrated lime.

In some embodiments, the additive of the present aqueous compositions comprises a surfactant. Surfactants are compounds that lower the surface tension of a liquid, the interfacial tension between two liquids, or that between a liquid and a solid. Surfactants may act as detergents, wetting agents, emulsifiers, foaming agents, and dispersants. Surfactants that can be present in the present aqueous compositions include cationic, anionic, and nonionic surfactants. Surfactants suitable for use in the present invention can include polysorbates such as polysorbate 20, polysorbate 40, polysorbate 60 or polysorbate 80.

In some embodiments, the additive of the present aqueous compositions comprises a solvent. Solvents are liquids which can be added to the present compositions, or to a substance (e.g. a hydrocarbon-containing substance), to decrease the density of a substance to be extracted or remediated by a Composition of the Invention. Solvents which are useful in the present aqueous compositions include terpenes such a d-limonene. In some embodiments, the solvent is diesel fuel. Such diesel fuel can be petroleum-derived, that is, obtained from the processing of crude oil. Alternatively, the diesel fuel can be biodiesel. Biodiesel is a vegetable oil or animal fat-based diesel fuel consisting of long-chain alkyl esters, which can be produced by chemically reacting lipids such as vegetable oil or animal fat with an alcohol to produce fatty acid esters. In one embodiment, the aqueous composition does not comprise a solvent.

In particular embodiments of the present invention, the aqueous compositions comprise a polysaccharide that is guar gum and plant material that is corn gluten meal. In other embodiments, the aqueous compositions further comprise one or more of water, isopropanol, citric acid, Type S hydrated lime, sodium hydroxide, and sodium chloride. In other embodiments of the present invention, the aqueous compositions comprise plant material that is corn gluten meal, and do not contain a polysaccharide other than that present in or derived from the corn gluten meal. In other embodiments, the aqueous compositions further comprise one or more of water, isopropanol, citric acid, Type S hydrated lime, sodium hydroxide, and sodium chloride.

Thus, in one embodiment, the present invention provides aqueous compositions comprising about 1 wt % to about 50 wt % of plant material, 0 to about 20 wt % of a polysaccharide, 0% to about 10 wt % of an alcohol, 0% to about 25 wt % of a base, 0% to about 30 wt % of a salt, 0% to about 10 wt % of an acid, 0% to about 30 wt % of an additive, 0% to about 30 wt % of a sugar, and about 10 wt % to about 95 wt % of water, wherein the aqueous composition has a pH of from about 9 to about 13.

In one embodiment, the aqueous compositions comprise from about 1 wt % to about 30 wt % of the plant material and 0 to about 10 wt % of the polysaccharide. In certain embodiments, the aqueous compositions comprise from about 1 wt % to about 10 wt % of the plant material and 0 to about 5 wt % of the polysaccharide. In other embodiments, the aqueous compositions comprise from about 1 wt % to about 5 wt % of the plant material and 0 to about 1 wt % of the polysaccharide. In some embodiments, the plant a cereal. In some embodiments, the cereal is corn, rice, wheat, barley, sorghum, millet, rye, triticale, fonio, flax, buckwheat, spelt or quinoa. In one embodiment, the cereal is corn. In other embodiments, the plant material is lentils (e.g., green, yellow, black), soybean, hemp seed, chia, grass, wheat grass and barley (e.g., pearl, groat). In some embodiments, the plant material comprises a plant protein. In some embodiments, the plant protein is from corn gluten meal.

In some embodiments, the plant is hemp, and the plant material is hemp seed. In some embodiments, the plant is soybean, and the plant material is soybean. In other embodiments, the plant is cotton. In certain embodiments, the plant protein is prolamine, zein, hordein, or gliadin. In some embodiments, the polysaccharide of the present aqueous composition is alginate, carrageenan, gum Arabic, tragacanth gum, guar gum, pectin, ghatti gum, xanthan gum, or mixtures thereof. In some embodiments, the polysaccharide is about 0.5 wt % to about 2 wt % of the aqueous composition. In some embodiments, the aqueous compositions do not comprise any of the aforementioned polysaccharides other than those present in or derived from the plant material. In other embodiments, the aqueous compositions do not comprise any of the aforementioned polysaccharides. In other embodiments, the aqueous compositions do not comprise polysaccharide.

In some embodiments, the aqueous composition further comprises an alcohol. In certain embodiments, the alcohol is ethanol, methanol, or isopropanol. In one embodiment, the alcohol is isopropanol. In some embodiments, the alcohol is about 0 wt % to about 10 wt % of the aqueous composition. In some embodiments, the aqueous composition does not comprise an alcohol. In some embodiments, the aqueous composition further comprises a base. In certain embodiments, the base is an inorganic base or an inorganic base. In other embodiments, the inorganic base is an alkali metal or alkaline earth metal base. In some embodiments, the inorganic base is sodium hydroxide, lithium hydroxide, potassium hydroxide, sodium carbonate, potassium carbonate, sodium bicarbonate, potassium bicarbonate, magnesium carbonate or calcium carbonate. In certain embodiments, the base is about 0 wt % to about 10 wt % of the aqueous composition. In some embodiments, the aqueous composition does not comprise a base.

In some embodiments, the aqueous composition further comprises a salt. In certain embodiments, the salt is sodium chloride, potassium chloride, calcium chloride, magnesium chloride, ammonium chloride, sodium bromide, potassium bromide, calcium bromide, magnesium bromide, ammonium bromide, sodium iodide, potassium iodide, calcium iodide, magnesium iodide, ammonium iodide, sodium sulfate, potassium sulfate, calcium sulfate, magnesium sulfate, ammonium sulfate, sodium nitrate, potassium nitrate, magnesium nitrate, calcium nitrate, ammonium nitrate or mixtures thereof. In certain embodiments, the salt is about 0 wt % to about 10 wt % of the aqueous composition. In some embodiments, the aqueous composition does not comprise a salt.

In some embodiments, the aqueous composition further comprises an acid. In certain embodiments, the acid is an organic acid. In other embodiments, the acids include inorganic acids. In certain embodiments, the inorganic acids include carbonic acid, sulfuric acid, or hydrochloric acid. In some embodiments, the acid is a C1-C20 organic acid. In certain embodiments, the acid is citric acid, formic acid, ascorbic acid, acetic acid, malic acid, adipic acid, tannic acid, lactic acid, fumaric acid, or mixtures thereof. In one embodiment, the acid is citric acid. In certain embodiments, the acid is about 0 wt % to about 10 wt % of the aqueous composition. In some embodiments, the aqueous composition does not comprise an acid.

In some embodiments, the aqueous composition of further comprises an additive. In certain embodiments, the additive is lime. In one embodiment, the lime is Type S Hydrated certain embodiments, the additive is lime. In certain embodiments, the lime is Type S Hydrated Lime. In certain embodiments, the Type S Hydrated Lime is about 0 wt % to about 10 wt % of the aqueous composition. In some embodiments, the aqueous composition does not comprise an additive. In some embodiments, the aqueous composition does not comprise lime.

In some embodiments, the aqueous composition comprises about 10 wt % to about 90 wt % water. In certain embodiments, the aqueous composition comprises about 80 wt % to about 90 wt % water. In certain embodiments, the aqueous composition comprises a polysaccharide and the polysaccharide and plant protein are in the form of a complex. In certain embodiments, the pH of the aqueous composition is from about 6 to about 8. In certain embodiments, the aqueous composition does not comprise a polysaccharide other than that derived from the plant material, wherein the plant material is hemp seed, and wherein the aqueous composition optionally further comprises one or more of isopropanol, citric acid, Type S hydrated lime, sodium hydroxide, and sodium chloride. In one embodiment, the aqueous compositions further comprise a substrate. In certain embodiments, the aqueous composition does not comprise a polysaccharide other than that derived from the plant material, wherein the plant material is hemp seed, and wherein the aqueous composition optionally further comprises one or more of isopropanol, citric acid, Type S hydrated lime, sodium hydroxide, and sodium chloride. In one embodiment, the aqueous compositions further comprise a substrate. In some embodiments, the plant material of the present aqueous compositions is an acidified plant material. In other embodiments, the plant material of the present aqueous compositions is a basified plant material.

Preparation of the Aqueous Compositions

The present aqueous compositions can be prepared by admixing the aqueous compositions' components, optionally in the presence of water or an organic solvent. For example, the aqueous compositions can be prepared by admixing the plant material component, in an amount as described herein, with one or both of water and an organic solvent to form a plant material mixture. The plant material mixture can be in a suspension or solution that can comprise an acid or base. The plant material can be added to the water, the organic solvent or both, or vice versa. The plant material mixture can be stirred or agitated until the plant material is suspended or substantially dissolved (e.g., about 10 minutes, about 20 minutes, about 30 minutes, about 40 minutes, about 50 minutes, about 1 hour, about 2 hours, about 3 hours, about 4 hours, or any other value or range of values therein or thereabove). The plant material mixture can be heated at a temperature of from about 5° C. to about 100° C. (e.g., about 5° C. to about 10° C., about 10° C. to about 15° C., about 15° C. to about 20° C., about 20° C. to about 25° C., about 25° C. to about 30° C., about 30° C. to about 35° C., about 35° C. to about 40° C., about 40° C. to about 45° C., about 45° C. to about 50° C., about 50° C. to about 55° C., about 55° C. to about 60° C., about 60° C. to about 65° C., about 65° C. to about 70° C., about 70° C. to about 75° C., about 75° C. to about 80° C., about 80° C. to about 85° C., about 85° C. to about 90° C., about 90° C. to about 95° C., about 95° C. to about 100° C., or any other value or range of values therein), optionally with mixing. In certain embodiments, the plant material mixture is prepared at ambient temperature (e.g., about 23° C.).

In some embodiments, the plant material is wetted with water (e.g., contacted or admixed with water, soaked in water, saturated with water) prior to admixing with other ingredients to form the present aqueous compositions. For example, the plant material may wetted with water for a time period ranging from about 5 minutes to about 168 hours (e.g., from about 5 minutes to about 10 minutes, from about 10 minutes to about 20 minutes, from about 20 minutes to about 30 minutes, from about 30 minutes to about 40 minutes, from about 40 minutes to about 50 minutes, from about 50 minutes to about 1 hour, from about 1 hour to about 2 hours, from about 2 hours to about 3 hours, from about 3 hours to about 4 hours, from about 4 hours to about 5 hours, from about 5 hours to about 6 hours, from about 6 hours to about 7 hours, from about 7 hours to about 8 hours, from about 8 hours to about 9 hours, from about 9 hours to about 10 hours, from about 10 hours to about 11 hours, from about 11 hours to about 12 hours, from about 12 hours to about 14 hours, from about 14 hours to about 16 hours, from about 16 hours to about 18 hours, from about 18 hours to about 20 hours, from about 20 hours to about 22 hours, from about 22 hours to about 24 hours, from about 24 hours to about 28 hours, from about 28 hours to about 32 hours, from about 32 hours to about 36 hours, from about 36 hours to about 40 hours, from about 40 hours to about 44 hours, from about 44 hours to about 48 hours, from about 48 hours to about 72 hours, from about 72 hours to about 96 hours, from about 96 hours to about 120 hours, from about 120 hours to about 144 hours, from about 144 hours to about 168 hours, or any other value or range of values therein). In some embodiments, the wetted plant material may be admixed with the water employed for wetting. In some embodiments, the plant material is wetted in a sterile environment. In other embodiments, the plant material which has been wetted with water may be separated from the wetting water (e.g., when the plant material has been immersed in water to effect said wetting) by, e.g., decantation or filtration, prior to admixing the protein with additional components of the present aqueous compositions. In some embodiments, the plant material is not wetted.

In other embodiments, an acid or a base is added to water, organic solvent or both, and the resultant solution is added to the plant material mixture, or vice versa, providing an acidified or basified plant material as described herein for use in preparing the present aqueous compositions. The acid or base can be undiluted or present as a mixture with water or an organic solvent. After addition of the acid or base, in certain embodiments the plant material mixture is allowed to stand for a period of time prior to addition of other components. For example, the plant material mixture can be allowed to stand for a period of about 10 minutes, about 20 minutes, about 30 minutes, about 40 minutes, about 50 minutes, about 1 hour, about 2 hours, about 3 hours, about 4 hours, about 8 hours, or any other value or range of values therein or thereabove). The plant material mixture can be allowed to stand at a temperature of from about 5° C. to about 100° C. (e.g., about 5° C. to about 10° C., about 10° C. to about 15° C., about 15° C. to about 20° C., about 20° C. to about 25° C., about 25° C. to about 30° C., about 30° C. to about 35° C., about 35° C. to about 40° C., about 40° C. to about 45° C., about 45° C. to about 50° C., about 50° C. to about 55° C., about 55° C. to about 60° C., about 60° C. to about 65° C., about 65° C. to about 70° C., about 70° C. to about 75° C., about 75° C. to about 80° C., about 80° C. to about 85° C., about 85° C. to about 90° C., about 90° C. to about 95° C., about 95° C. to about 100° C., or any other value or range of values therein). In certain embodiments, after addition of the acid or base, the plant material mixture is allowed to stand at ambient temperature (e.g., about 23° C.).

Where the aqueous compositions comprise a polysaccharide other than that which is present or derived from the plant material, the polysaccharide is added to the plant material mixture, or vice versa. In some embodiments, protein from the plant material and polysaccharide form a protein-polysaccharide complex in solution. Typically the plant material and polysaccharide are admixed with agitation (e.g., stirring, mixing). The mixture comprising the plant material and polysaccharide can be admixed with agitation for a period of about 10 minutes, about 20 minutes, about 30 minutes, about 40 minutes, about 50 minutes, about 1 hour, about 2 hours, about 3 hours, about 4 hours, or any other value or range of values therein or thereabove) and at a temperature of from about 5° C. to about 100° C. (e.g., about 5° C. to about 10° C., about 10° C. to about 15° C., about 15° C. to about 20° C., about 20° C. to about 25° C., about 25° C. to about 30° C., about 30° C. to about 35° C., about 35° C. to about 40° C., about 40° C. to about 45° C., about 45° C. to about 50° C., about 50° C. to about 55° C., about 55° C. to about 60° C., about 60° C. to about 65° C., about 65° C. to about 70° C., about 70° C. to about 75° C., about 75° C. to about 80° C., about 80° C. to about 85° C., about 85° C. to about 90° C., about 90° C. to about 95° C., about 95° C. to about 100° C., or any other value or range of values therein). In certain embodiments, the mixture comprising the plant material and polysaccharide is agitated at ambient temperature (e.g., about 23° C.).

In some embodiments, a salt is added to the plant material mixture, or vice versa, typically with agitation (e.g., stirring, mixing). The plant material mixture can be agitated for a period of about 10 minutes, about 20 minutes, about 30 minutes, about 40 minutes, about 50 minutes, about 1 hour, about 2 hours, about 3 hours, about 4 hours, or any other value or range of values therein or thereabove) and at a temperature of from about 5° C. to about 100° C. (e.g., about 5° C. to about 10° C., about 10° C. to about 15° C., about 15° C. to about 20° C., about 20° C. to about 25° C., about 25° C. to about 30° C., about 30° C. to about 35° C., about 35° C. to about 40° C., about 40° C. to about 45° C., about 45° C. to about 50° C., about 50° C. to about 55° C., about 55° C. to about 60° C., about 60° C. to about 65° C., about 65° C. to about 70° C., about 70° C. to about 75° C., about 75° C. to about 80° C., about 80° C. to about 85° C., about 85° C. to about 90° C., about 90° C. to about 95° C., about 95° C. to about 100° C., or any other value or range of values therein). In certain embodiments, the plant material mixture is agitated at ambient temperature (e.g., about 23° C.).

The plant material mixture can then be admixed with one or more additives described herein. The plant material mixture can be added to the one or more additives, or vice versa. Typically the plant material mixture and one or more additives are admixed with agitation (e.g., stirring, mixing). The resultant mixture can be agitated for a period of time until it becomes uniform, e.g., a solution or a uniform suspension. For example, the resultant mixture can be agitated for a period of about 10 minutes, about 20 minutes, about 30 minutes, about 40 minutes, about 50 minutes, about 1 hour, about 2 hours, about 3 hours, about 4 hours, or any other value or range of values therein or thereabove) and at a temperature of from about 5° C. to about 100° C. (e.g., about 5° C. to about 10° C., about 10° C. to about 15° C., about 15° C. to about 20° C., about 20° C. to about 25° C., about 25° C. to about 30° C., about 30° C. to about 35° C., about 35° C. to about 40° C., about 40° C. to about 45° C., about 45° C. to about 50° C., about 50° C. to about 55° C., about 55° C. to about 60° C., about 60° C. to about 65° C., about 65° C. to about 70° C., about 70° C. to about 75° C., about 75° C. to about 80° C., about 80° C. to about 85° C., about 85° C. to about 90° C., about 90° C. to about 95° C., about 95° C. to about 100° C., or any other value or range of values therein). In certain embodiments, the resultant mixture is agitated at ambient temperature (e.g., about 23° C.).

The resultant mixture is then allowed to stand without agitation to allow any undissolved or unsuspended solids to precipitate. The resultant mixture can be allowed to stand at a temperature of from about 5° C. to about 100° C. (e.g., about 5° C. to about 10° C., about 10° C. to about 15° C., about 15° C. to about 20° C., about 20° C. to about 25° C., about 25° C. to about 30° C., about 30° C. to about 35° C., about 35° C. to about 40° C., about 40° C. to about 45° C., about 45° C. to about 50° C., about 50° C. to about 55° C., about 55° C. to about 60° C., about 60° C. to about 65° C., about 65° C. to about 70° C., about 70° C. to about 75° C., about 75° C. to about 80° C., about 80° C. to about 85° C., about 85° C. to about 90° C., about 90° C. to about 95° C., about 95° C. to about 100° C., or any other value or range of values therein) for a period of about 10 minutes, about 20 minutes, about 30 minutes, about 40 minutes, about 50 minutes, about 1 hour, about 2 hours, about 3 hours, about 4 hours, about 8 hours, or any other value or range of values therein or thereabove). In certain embodiments, after admixture with an additive, the resultant mixture is allowed to stand at ambient temperature (e.g., about 23° C.), until any undissolved or unsuspended solids present have precipitated. The resultant mixture can then be decanted or filtered to remove the solids therefrom, and the solids are discarded, to provide the present aqueous composition in the form of a solvent mixture. The solvent mixture generally has a final pH ranging from about 5 to about 14 (e.g., from about 5 to about 6, from about 6 to about 7, from about 7 to about 8, from about 8 to about 9, from about 9 to about 10, from about 10 to about 11, from about 11 to about 12, from about 12 to about 13, from about 13 to about 14, or any other value or range of values therein). In certain embodiments, the pH ranges from about 6 to about 8. In other embodiments, the pH is about 13. In certain embodiments, the pH of the solvent mixture ranges from about 5 to about 13; from about 6 to about 13; from about 7 to about 13; from about 8 to about 13; from about 9 to about 13; from about 10 to about 13; from about 11 to about 13; from about 12 to about 13.

In certain embodiments, the resultant mixture can be further purified via the application of gravity or another force that can effect separation of one or more unwanted by-products (e.g., solids, gels, suspensions and the like) from the present aqueous compositions. For example, in some embodiments, the resultant mixture is subject to centrifugal force effected by a centrifuge to remove one or more unwanted by-products. The centrifugal force applied can be expressed in terms of relative centrifugal force (RCF), as a number (n) times the force of gravity (g), and has units of g, wherein 1 g is the force of gravity at sea level. RCF can be a convenient value to use when describing the centrifugal force acting on a given material because it is a constant that is independent of the apparatus used. Thus, in some embodiments, the RCF applied to the resultant mixture is from about 100 g to about 20,000 g (e.g., from about 10 g to about 1,000 g, from about 1,000 g to about 2,000 g, from about 2,000 g to about 3,000 g, from about 3,000 g to about 4,000 g, from about 4,000 g to about 5,000 g, from about 5,000 g to about 6,000 g, from about 6,000 g to about 7,000 g, from about 7,000 g to about 8,000 g, from about 8,000 g to about 9,000 g, from about 9,000 g to about 10,000 g, from about 10,000 g to about 11,000 g, from about 11,000 g to about 12,000 g, from about 12,000 g to about 13,000 g, from about 13,000 g to about 14,000 g, from about 14,000 g to about 15,000 g, from about 15,000 g to about 16,000 g, from about 16,000 g to about 17,000 g, from about 17,000 g to about 18,000 g, from about 18,000 g to about 19,000 g, from about 19,000 g to about 20,000 g, or any other value or range of values therein). In some embodiments, the RCF ranges from about 12,000 g to about 18,000 g. In other embodiments, the RCF ranges from about 15,000 g to about 18,000 g. After such centrifugation, the supernatant may be removed by, e.g., suction, decantation, filtration and the like, to afford the present aqueous compositions. In some embodiments, one or more additives as described herein can be added to the present aqueous compositions after purification be, e.g., filtration or centrifugation.

Extractants

The present compositions can be combined with water to form an extractant useful in the methods described herein. Thus, in another embodiment, the present invention relates to extractants comprising: about 0.1 wt % to about 2 wt % of plant material; 0% to about 2 wt % of a polysaccharide; 0% to about 1 wt % of an alcohol; 0% to about 10 wt % of a base; 0% to about 30 wt % of a salt; 0% to about 10 wt % of an acid; 0% to about 30 wt % of an additive; 0% to about 30 wt % of a sugar; and about 90 wt % to about 99.9 wt % water; wherein the plant material is hemp seed, soybean, or combinations thereof. In some embodiments, the plant material of the present extractants is an acidified plant material. In other embodiments, the plant material of the present extractants is a basified plant material.

In another embodiment, the present invention provides an extractant composition comprising about 0.1 wt % to about 2 wt % of plant material; 0% to about 2 wt % of a polysaccharide; 0% to about 1 wt % of an alcohol; 0% to about 10 wt % of a base; 0% to about 10 wt % of a salt; 0% to about 10 wt % of an acid; 0% to about 10 wt % of an additive; and about 90 wt % to about 99.9 wt % water. In one embodiment, the extractant composition comprises about 0.1 wt % to about 2 wt % of plant material; 0% to about 2 wt % of a polysaccharide; 0% to about 1 wt % of an alcohol; 0% to about 10 wt % of a base; 0% to about 10 wt % of a salt; 0% to about 10 wt % of an acid; 0% to about 10 wt % of an additive; and about 90 wt % to about 99.9 wt % water. In yet another embodiment, the extractant composition comprises about 20 wt % to about 99.9 wt % of plant material; 0 to about 20 wt % of a polysaccharide; 0% to about 1 wt % of an alcohol; 0% to about 15 wt % of a base;

0% to about 10 wt % of a salt; 0% to about 10 wt % of an acid; 0% to about 10 wt % of an additive; and 0% to about 10 wt % water.

In some embodiments, the extractant comprises about 0.1 wt % to about 1 wt % of plant material and 0 to about 1 wt % of a polysaccharide. In certain embodiments, the extractant comprises about 0.1 wt % to about 0.5 wt % of plant material and 0 to about 1 wt % of a polysaccharide. In some embodiments, the extractant does not comprise a polysaccharide other than that present in or derived from the plant material. In other embodiments, the aqueous compositions do not comprise a polysaccharide.

The polysaccharide can be present in the extractants in an amount ranging from about 0 to about 2 wt % (e.g., about 0.01 wt % to about 0.05 wt %, about 0.05 wt % to about 0.1 wt %, about 0.1 wt % to about 0.2 wt %, about 0.2 wt % to about 0.3 wt %, about 0.3 wt % to about 0.4 wt %, about 0.4 wt % to about 0.5 wt %, about 0.5 wt % to about 1.0 wt %, about 1.0 wt % to about 1.5 wt %, about 1.5 wt % to about 2.0 wt %, or any other value or range of values therein). In some embodiments, the polysaccharide is present in an amount of from 0 wt % to about 1 wt %. In other embodiments, the present extractants do not comprise a polysaccharide other than that present in or derived from the plant material. When present, polysaccharides which are useful in the present extractants include those as described herein which can be employed in the present aqueous compositions.

In some embodiments, the plant material is present in the extractants in an amount ranging from about 0.1 to about 2 wt % (e.g., about 0.01 wt % to about 0.05 wt %, about 0.05 wt % to about 0.1 wt %, about 0.1 wt % to about 0.2 wt %, about 0.2 wt % to about 0.3 wt %, about 0.3 wt % to about 0.4 wt %, about 0.4 wt % to about 0.5 wt %, about 0.5 wt % to about 0.6 wt %, about 0.6 wt % to about 0.7 wt %, about 0.7 wt % to about 0.8 wt %, about 0.8 wt % to about 0.9 wt %, about 0.9 wt % to about 1.0 wt %, about 1.0 wt % to about 1.5 wt %, about 1.5 wt % to about 2.0 wt %, or any other value or range of values therein). Plant materials which are useful in the present extractant include those as described herein which can be employed in the present aqueous compositions. In some embodiments, the plant material is present in an amount of from about 0.1 wt % to about 1 wt %. In certain embodiments, the plant material is present in an amount of from about 0.1 wt % to about 0.5 wt %.

The present extractants can further comprise an acid or a base. Acids and bases useful in the present extractants are those as described herein which are useful in the present aqueous compositions. The acid can be present in the extractants in an amount from 0 wt % to about 1 wt % (e.g., about 0 to about 0.01 wt %, about 0.01 wt % to about 0.05 wt %, about 0.05 wt % to about 0.1 wt %, about 0.1 wt % to about 0.2 wt %, about 0.2 wt % to about 0.3 wt %, about 0.3 wt % to about 0.4 wt %, about 0.4 wt % to about 0.5 wt %, about 0.5 wt % to about 0.6 wt %, about 0.6 wt % to about 0.7 wt %, about 0.7 wt % to about 0.8 wt %, about 0.8 wt % to about 0.9 wt %, about 0.9 wt % to about 1 wt %, or any other value or range of values therein). In some embodiments, the acid is present from about 0.01 wt % to about 1 wt % of the extractant. In some embodiments, the extractant does not comprise an acid.

The base can be present in the extractants in an amount from 0 wt % to about 30 wt % (e.g., about 0 to about 0.01 wt %, about 0.01 wt % to about 0.05 wt %, about 0.05 wt % to about 0.1 wt %, about 0.1 wt % to about 0.2 wt %, about 0.2 wt % to about 0.3 wt %, about 0.3 wt % to about 0.4 wt %, about 0.4 wt % to about 0.5 wt %, about 0.5 wt % to about 0.6 wt %, about 0.6 wt % to about 0.7 wt %, about 0.7 wt % to about 0.8 wt %, about 0.8 wt % to about 0.9 wt %, about 0.9 wt % to about 1 wt %, about 1 wt % to about 2 wt %, about 2 wt % to about 3 wt %, about 3 wt % to about 4 wt %, about 4 wt % to about 5 wt %, about 5 wt % to about 6 wt %, about 6 wt % to about 7 wt %, about 7 wt % to about 8 wt %, about 8 wt % to about 9 wt %, about 9 wt % to about 10 wt %, about 10 wt % to about 11 wt %, about 11 wt % to about 12 wt %, about 12 wt % to about 13 wt %, about 13 wt % to about 14 wt %, about 14 wt % to about 15 wt %, about 15 wt % to about 16 wt %, about 16 wt % to about 17 wt %, about 17 wt % to about 18 wt %, about 18 wt % to about 19 wt %, about 19 wt % to about 20 wt %, about 20 wt % to about 21 wt %, about 21 wt % to about 22 wt %, about 22 wt % to about 23 wt %, about 23 wt % to about 24 wt %, about 24 wt % to about 25 wt %, about 25 wt % to about 26 wt %, about 26 wt % to about 27 wt %, about 27 wt % to about 28 wt %, about 28 wt % to about 29 wt %, about 29 wt % to about 30 wt %, or any other value or range of values therein). In some embodiments, the base is present from about 0.01 wt % to about 1 wt % of the extractants. In some embodiments, the extractant does not comprise a base.

The present extractants can also comprise a salt. Salts useful in the present extractants are those as described herein which are useful in the present aqueous compositions. The salt can be present in the extractants in an amount from 0 wt % to about 30 wt % (e.g., about 0 to about 0.01 wt %, about 0.01 wt % to about 0.05 wt %, about 0.05 wt % to about 0.1 wt %, about 0.1 wt % to about 0.2 wt %, about 0.2 wt % to about 0.3 wt %, about 0.3 wt % to about 0.4 wt %, about 0.4 wt % to about 0.5 wt %, about 0.5 wt % to about 0.6 wt %, about 0.6 wt % to about 0.7 wt %, about 0.7 wt % to about 0.8 wt %, about 0.8 wt % to about 0.9 wt %, about 0.9 wt % to about 1 wt %, about 1 wt % to about 2 wt %, about 2 wt % to about 3 wt %, about 3 wt % to about 4 wt %, about 4 wt % to about 5 wt %, about 5 wt % to about 6 wt %, about 6 wt % to about 7 wt %, about 7 wt % to about 8 wt %, about 8 wt % to about 9 wt %, about 9 wt % to about 10 wt %, about 10 wt % to about 11 wt %, about 11 wt % to about 12 wt %, about 12 wt % to about 13 wt %, about 13 wt % to about 14 wt %, about 14 wt % to about 15 wt %, about 15 wt % to about 16 wt %, about 16 wt % to about 17 wt %, about 17 wt % to about 18 wt %, about 18 wt % to about 19 wt %, about 19 wt % to about 20 wt %, about 20 wt % to about 21 wt %, about 21 wt % to about 22 wt %, about 22 wt % to about 23 wt %, about 23 wt % to about 24 wt %, about 24 wt % to about 25 wt %, about 25 wt % to about 26 wt %, about 26 wt % to about 27 wt %, about 27 wt % to about 28 wt %, about 28 wt % to about 29 wt %, about 29 wt % to about 30 wt %, or any other value or range of values therein). In some embodiments, the salt is present from about 0.01 wt % to about 1 wt % of the extractant. In some embodiments, the extractant does not comprise a salt.

The present extractants can further comprise an organic solvent. Organic solvents which can be present in the extractants include those described herein which can be present in the aqueous compositions of the invention. The amount of organic solvent, if present, can be in an amount of 0 wt % to about 1 wt % (e.g., about 0 to about 0.01 wt %, about 0.01 wt % to about 0.05 wt %, about 0.05 wt % to about 0.1 wt %, about 0.1 wt % to about 0.2 wt %, about 0.2 wt % to about 0.3 wt %, about 0.3 wt % to about 0.4 wt %, about 0.4 wt % to about 0.5 wt %, about 0.5 wt % to about 0.6 wt %, about 0.6 wt % to about 0.7 wt %, about 0.7 wt % to about 0.8 wt %, about 0.8 wt % to about 0.9 wt %, about 0.9 wt % to about 1 wt %, or any other value or range of values therein). In some embodiments, the extractant dos not comprise an organic solvent. In some embodiments, the extractant dos not comprise an alcohol.

The present extractants can also comprise one or more other additives. Additives that can be present in the extractants include those described herein which can be present in the aqueous compositions of the invention. The additive(s) can be present in the extractants in amounts ranging from 0 to about 30 wt % (e.g., about 0 to about 0.01 wt %, about 0.01 wt % to about 0.05 wt %, about 0.05 wt % to about 0.1 wt %, about 0.1 wt % to about 0.2 wt %, about 0.2 wt % to about 0.3 wt %, about 0.3 wt % to about 0.4 wt %, about 0.4 wt % to about 0.5 wt %, about 0.5 wt % to about 0.6 wt %, about 0.6 wt % to about 0.7 wt %, about 0.7 wt % to about 0.8 wt %, about 0.8 wt % to about 0.9 wt %, about 0.9 wt % to about 1 wt %, about 1 wt % to about 2 wt %, about 2 wt % to about 3 wt %, about 3 wt % to about 4 wt %, about 4 wt % to about 5 wt %, about 5 wt % to about 6 wt %, about 6 wt % to about 7 wt %, about 7 wt % to about 8 wt %, about 8 wt % to about 9 wt %, about 9 wt % to about 10 wt %, about 10 wt % to about 11 wt %, about 11 wt % to about 12 wt %, about 12 wt % to about 13 wt %, about 13 wt % to about 14 wt %, about 14 wt % to about 15 wt %, about 15 wt % to about 16 wt %, about 16 wt % to about 17 wt %, about 17 wt % to about 18 wt %, about 18 wt % to about 19 wt %, about 19 wt % to about 20 wt %, about 20 wt % to about 21 wt %, about 21 wt % to about 22 wt %, about 22 wt % to about 23 wt %, about 23 wt % to about 24 wt %, about 24 wt % to about 25 wt %, about 25 wt % to about 26 wt %, about 26 wt % to about 27 wt %, about 27 wt % to about 28 wt %, about 28 wt % to about 29 wt %, about 29 wt % to about 30 wt %, or any other value or range of values therein). In certain embodiments, the additive is Type-S hydrated lime. In certain embodiments, the additive is polysorbate. In certain embodiments, the additive is diesel fuel. In certain embodiments, the additive is biodiesel. In some embodiments, the extractant dos not comprise an additive. In some embodiments, the extractant does not comprise lime. In some embodiments, the extractant does not comprise Type-S hydrated lime.

The amount of water in the present extractants can range from about 50 to about 99.9 wt % (e.g., about 50 wt % to about 51 wt %, about 51 wt % to about 52 wt %, about 52 wt % to about 53 wt %, about 53 wt % to about 54 wt %, about 54 wt % to about 55 wt %, about 55 wt % to about 56 wt %, about 56 wt % to about 57 wt %, about 57 wt % to about 58 wt %, about 58 wt % to about 59 wt %, about 59 wt % to about 60 wt %, about 60 wt % to about 61 wt %, about 61 wt % to about 62 wt %, about 62 wt % to about 63 wt %, about 63 wt % to about 64 wt %, about 64 wt % to about 65 wt %, about 65 wt % to about 66 wt %, about 66 wt % to about 67 wt %, about 67 wt % to about 68 wt %, about 68 wt % to about 69 wt %, about 69 wt % to about 70 wt %, about 70 wt % to about 71 wt %, about 71 wt % to about 72 wt %, about 72 wt % to about 73 wt %, about 73 wt % to about 74 wt %, about 74 wt % to about 75 wt %, about 75 wt % to about 76 wt %, about 76 wt % to about 77 wt %, about 77 wt % to about 78 wt %, about 78 wt % to about 79 wt %, about 79 wt % to about 80 wt %, about 80 wt % to about 81 wt %, about 81 wt % to about 82 wt %, about 82 wt % to about 83 wt %, about 83 wt % to about 84 wt %, about 84 wt % to about 85 wt %, about 85 wt % to about 86 wt %, about 86 wt % to about 87 wt %, about 87 wt % to about 88 wt %, about 88 wt % to about 89 wt %, about 89 wt % to about 90 wt %, about 90 wt % to about 91 wt %, about 91 wt % to about 92 wt %, about 92 wt % to about 93 wt %, about 93 wt % to about 94 wt %, about 94 wt % to about 95 wt %, about 95 wt % to about 96 wt %, about 96 wt % to about 97 wt %, about 97 wt % to about 98 wt %, about 98 wt % to about 99 wt %, about 99 wt % to about 99.5 wt %, about 99.5 wt % to about 99.9 wt %, or any other value or range of values therein). In certain embodiments, the extractant comprises from about 95 wt % to about 99.9% wt % water.

In particular embodiments of the present invention, the extractants comprise a polysaccharide that is guar gum and plant material that is hemp seed. In other embodiments of the present invention, the extractants comprise plant material that is hemp seed meal and does not contain a polysaccharide other than that present in the hemp seed. In other embodiments, the extractants optionally further comprise one or more water, isopropanol, citric acid, Type S hydrated lime, sodium hydroxide, and sodium chloride.

Thus, in some embodiments, the present invention extractants comprise about 0.1 wt % to about 2 wt % of plant material, 0 to about 2 wt % of a polysaccharide, 0% to about 1 wt % of an alcohol, 0% to about 30 wt % of a base, 0% to about 30 wt % of a salt, 0% to about 10 wt % of an acid, 0% to about 30 wt % of an additive, and about 50 wt % to about 99.9 wt % water. In certain embodiments, the extractant comprises from about 0.1 wt % to about 1 wt % of the plant material and 0 to about 1 wt % of the polysaccharide. In certain embodiments, the extractant comprises about 0.1 wt % to about 0.5 wt % of the plant material and 0 to about 0.1 wt % of the polysaccharide. In some embodiments, the plant material comprises plant protein. In some embodiments, the plant proteins are prolamines. In some embodiments, the plant of the extractant is a cereal. In certain embodiments, the cereal is corn, rice, wheat, barley, sorghum, millet, rye, triticale, fonio, buckwheat, wheat grass, wheat, spelt or quinoa. In certain embodiments, the cereal is corn. In other embodiments, the plant material is lentils (e.g., green, yellow, black), soybean, hemp seed, chia, grass, wheat grass and barley (e.g., pearl, groat). In some embodiments, the polysaccharide of the extractant is alginate, carrageenan, gum Arabic, tragacanth gum, guar gum, pectin, ghatti gum, xanthan gum, or mixtures thereof. In certain embodiments, the extractant does not comprise polysaccharide other than that present in or derived from the plant material. In certain embodiments, the extractant does not comprise any of the aforementioned polysaccharides other than that present in or derived from the plant material. In certain embodiments, the polysaccharide is about 0.05 wt % to about 0.2 wt % of the extractant. In some embodiments, the extractant does not comprise polysaccharide.

In some embodiments, the extractant further comprises an alcohol. In certain embodiments, the alcohol is ethanol, methanol, or isopropanol. In one embodiment, the alcohol is isopropanol. In some embodiments, the alcohol is about 0 wt % to about 1 wt % of the extractant. In some embodiments, the extractant does not comprise an alcohol.

In certain embodiments, the extractant further comprises a base. In other embodiments, the base is an inorganic base or an inorganic base. In some embodiments, the inorganic base is an alkali metal or alkaline earth metal base. In certain embodiments, the inorganic base is sodium hydroxide, lithium hydroxide, potassium hydroxide, sodium carbonate, potassium carbonate, sodium bicarbonate, potassium bicarbonate, magnesium carbonate or calcium carbonate. In one embodiment, the base is 0 wt % to about 1 wt % of the extractant. In some embodiments, the extractant does not comprise a base.

In certain embodiments, the extractant further comprises a salt. In some embodiments, the salt is sodium chloride, potassium chloride, calcium chloride, magnesium chloride, ammonium chloride, sodium bromide, potassium bromide, calcium bromide, magnesium bromide, ammonium bromide, sodium iodide, potassium iodide, calcium iodide, magnesium iodide, ammonium iodide, sodium sulfate, potassium sulfate, calcium sulfate, magnesium sulfate, ammonium sulfate, sodium nitrate, potassium nitrate, magnesium nitrate, calcium nitrate, ammonium nitrate or mixtures thereof. In certain embodiments, the salt is 0 wt % to about 1 wt % of the extractant. In some embodiments, the extractant does not comprise a salt.

In certain embodiments, the extractant further comprises an acid. In other embodiments, the acids include inorganic acids. In certain embodiments, the inorganic acids include carbonic acid, sulfuric acid, or hydrochloric acid. In some embodiments, the acid is an organic acid. In certain embodiments, the acid is a C1-C20 organic acid. In other embodiments, the acid is citric acid, formic acid, ascorbic acid, acetic acid, malic acid, adipic acid, tannic acid, lactic acid, fumaric acid, or mixtures thereof. In one embodiment, the acid is citric acid. In certain embodiments, the acid is 0 wt % to about 1 wt % of the extractant. In some embodiments, the extractant does not comprise an acid.

In some embodiments, the extractant further comprises an additive. In certain embodiments, the additive is lime. In one embodiment, the lime is Type S Hydrated Lime. In some embodiments, the extractant does not comprise an additive. In certain embodiments, the Type S Hydrated Lime is 0 wt % to about 1 wt % of the extractant. In some embodiments, the extractant does not comprise lime. In some embodiments, the extractant does not comprise S type hydrated lime. In certain embodiments, the extractant comprises about 95 wt % to about 99 wt % water. In some embodiments, the pH of the extractant is from about 5 to about 14. In certain embodiments, the pH of the extractant is from about 6 to about 8. In certain embodiments, the pH of the extractant ranges from about 5 to about 13; from about 6 to about 13; from about 7 to about 13; from about 8 to about 13; from about 9 to about 13; from about 10 to about 13; from about 11 to about 13; from about 12 to about 13. In certain embodiments, the extractant does not comprise a polysaccharide other than that present in or derived from the plant material. In one embodiment, the extractant does not comprise a polysaccharide other than that derived from the plant material, the plant material is corn gluten meal, and the aqueous composition further comprises isopropanol, citric acid, Type S hydrated lime, sodium hydroxide, and sodium chloride. In certain embodiments, the aqueous composition does not comprise a polysaccharide other than that derived from the plant material, wherein the plant material is hemp seed, and wherein the aqueous composition optionally further comprises one or more of isopropanol, citric acid, Type S hydrated lime, sodium hydroxide, and sodium chloride. In certain embodiments, the extractant further comprises a substrate. In some embodiments, the plant material of the present extractants is an acidified plant material. In other embodiments, the plant material of the present extractants is a basified plant material.

Preparation of the Extractants

The present extractants can be made by adding water to the aqueous compositions of the invention as described herein. A desired water percentage of the present extractants can be selected in view of a particular application, such as oil sand extraction, coal tar extraction, hydraulic fracturing, soil remediation, or spill cleanup as described herein.

Thus, in one embodiment, the present invention provides a method for making an extractant comprising about 0.1 wt % to about 2 wt % of plant material, 0 to about 2 wt % of a polysaccharide, 0% to about 1 wt % of an alcohol, 0% to about 30 wt % of a base, 0% to about 30 wt % of a salt, 0% to about 10 wt % of an acid, 0% to about 30 wt % of an additive, and about 50 wt % to about 99.9 wt % water, comprising adding water to an aqueous composition of the present invention in an amount of from about 90 wt % to about 99.9 wt %. In certain embodiments, the method comprises preparing an extractant comprising about 0.1 wt % to about 2 wt % of plant material, 0 to about 2 wt % of a polysaccharide, 0% to about 1 wt % of an alcohol, 0% to about 10 wt % of a base, 0% to about 10 wt % of a salt, 0% to about 10 wt % of an acid, 0% to about 10 wt % of an additive, and about 90 wt % to about 99.9 wt % water, comprising adding water to a substantially anhydrous composition as described herein in an amount of from about 90 wt % to about 99.9 wt %. In some embodiments, one or more additives may be added after adding water to the aqueous composition.

Substantially Anhydrous Compositions

The present aqueous compositions or extractants can be dried to form a substantially anhydrous composition. "Substantially anhydrous" means that the compositions comprise no more than about 10% water; in another embodiment, no more than about 5% water; in another embodiment, no more than about 2% water; in another embodiment, no more than about 1% water by weight of the composition; in another embodiment, no more than about 0.5% water by weight of the composition; and in another embodiment, no more than about 0.1% by weight of the composition.

Thus, in another aspect, the present invention relates to substantially anhydrous compositions comprising: about 20 wt % to about 99.9 wt % of plant material; 0 to about 20 wt % of a polysaccharide; 0% to about 1 wt % of an alcohol; 0% to about 30 wt % of a base; 0% to about 50 wt % of a salt; 0% to about 10 wt % of an acid; 0% to about 30 wt % of an additive; and 0% to about 10 wt % water; 0% to about 30 wt % of a sugar; wherein the plant material is hemp seed, soybean, or combinations thereof. In some embodiments, the plant material of the present anhydrous compositions is an acidified plant material. In other embodiments, the plant material of the present anhydrous compositions is a basified plant material.

In another embodiment, the present invention provides substantially anhydrous compositions comprising about 0.1 wt % to about 2 wt % of plant material; 0% to about 2 wt % of a polysaccharide; 0% to about 1 wt % of an alcohol; 0% to about 10 wt % of a base; 0% to about 10 wt % of a salt; 0% to about 10 wt % of an acid; 0% to about 10 wt % of an additive; and about 90 wt % to about 99.9 wt % water. In yet another embodiment, the substantially anhydrous composition comprises about 20 wt % to about 99.9 wt % of plant material; 0 to about 20 wt % of a polysaccharide; 0% to about 1 wt % of an alcohol; 0% to about 15 wt % of a base; 0% to about 10 wt % of a salt; 0% to about 10 wt % of an acid; 0% to about 10 wt % of an additive; and 0% to about 10 wt % water.

The plant material and, if present, the polysaccharide of the present substantially anhydrous compositions can be present in relative amounts such that they form a complex. Polysaccharides that are useful in the present substantially anhydrous compositions include those as described herein. In some embodiments, the present substantially anhydrous compositions do not comprise polysaccharide other than that derived from the plant material. In other embodiments, the present substantially anhydrous compositions do not comprise polysaccharide.

The polysaccharide can be present in the substantially anhydrous compositions in an amount ranging from about 0 to about 20 wt % (e.g., 0 to about 0.5 wt %, about 0.5 wt % to about 1 wt %, about 1 wt % to about 2 wt %, about 2 wt % to about 3 wt %, about 3 wt % to about 4 wt %, about 4 wt % to about 5 wt %, about 5 wt % to about 6 wt %, about 6 wt % to about 7 wt %, about 7 wt % to about 8 wt %, about 8 wt % to about 9 wt %, about 9 wt % to about 10 wt %, about 10 wt % to about 11 wt %, about 11 wt % to about 12 wt %, about 12 wt % to about 13 wt %, about 13 wt % to about 14 wt %, about 14 wt % to about 15 wt %, about 15 wt % to about 16 wt %, about 16 wt % about 17 wt %, about 17 wt % to about 18 wt %, about 18 wt % to about 19 wt %, about 19 wt % to about 20 wt %, or any other value or range of values therein). In some embodiments, the polysaccharide is present in an amount of from 0 wt % to about 10 wt %. In other embodiments, the present substantially anhydrous compositions do not comprise a polysaccharide other than that present in or derived from the plant material. When present, polysaccharides that are useful in the present substantially anhydrous compositions include those as described herein.

In some embodiments, the plant material is present in the substantially anhydrous compositions in an amount ranging from about 20 wt % to about 99.9 wt % (e.g., about 20 wt % to about 25 wt %, about 25 wt % to about 30 wt %, about 30 wt % to about 35 wt %, about 35 wt % to about 40 wt %, about 40 wt % to about 45 wt %, about 45 wt % to about 50 wt %, about 50 wt % to about 55 wt %, about 55 wt % to about 60 wt %, about 60 wt % to about 65 wt %, about 65 wt % to about 70 wt %, about 70 wt % to about 75 wt %, about 75 wt % to about 80 wt %, about 80 wt % to about 85 wt %, about 85 wt % to about 90 wt %, about 90 wt % to about 91 wt %, about 91 wt % to about 92 wt %, about 92 wt % to about 93 wt %, about 93 wt % to about 94 wt %, about 94 wt % to about 95 wt %, about 95 wt % to about 96 wt %, about 96 wt % to about 97 wt %, about 97 wt % to about 98 wt %, about 98 wt % to about 99 wt %, about 99 wt % to about 99.5 wt %, about 99.5 wt % to about 99.9 wt %, or any other value or range of values therein). Plant materials which are in the present substantially anhydrous compositions include those as described herein. In some embodiments, the plant material is present in an amount of from about 85 wt % to about 99.9 wt %. In certain embodiments, the plant material is present in an amount of from about 95 wt % to about 99.9 wt %. In some embodiments, the plant material comprises a plant protein.

The present substantially anhydrous compositions can further comprise an acid or a base. Acids and bases useful in the present substantially anhydrous compositions are those as described herein. The acid can be present in the substantially anhydrous compositions in an amount from 0 wt % to about 10 wt % (e.g., 0 to about 0.5 wt %, about 0.5 wt % to about 1 wt %, about 1 wt % to about 2 wt %, about 2 wt % to about 3 wt %, about 3 wt % to about 4 wt %, about 4 wt % to about 5 wt %, about 5 wt % to about 6 wt %, about 6 wt % to about 7 wt %, about 7 wt % to about 8 wt %, about 8 wt % to about 9 wt %, about 9 wt % to about 10 wt %, or any other value or range of values therein). In some embodiments, the acid is present from about 0.01 wt % to about 2 wt % of the substantially anhydrous compositions. In some embodiments, the substantially anhydrous compositions do not comprise an acid.

The base can present in the substantially anhydrous compositions in an amount from 0 wt % to about 50 wt % (e.g., 0 to about 0.5 wt %, about 0.5 wt % to about 1 wt %, about 1 wt % to about 2 wt %, about 2 wt % to about 3 wt %, about 3 wt % to about 4 wt %, about 4 wt % to about 5 wt %, about 5 wt % to about 6 wt %, about 6 wt % to about 7 wt %, about 7 wt % to about 8 wt %, about 8 wt % to about 9 wt %, about 9 wt % to about 10 wt %, about 10 wt % to about 15 wt %, about 15 wt % to about 20 wt %, about 20 wt % to about 25 wt %, about 25 wt % to about 30 wt %, about 30 wt % to about 35 wt %, about 35 wt % to about 40 wt %, about 40 wt % to about 45 wt %, about 45 wt % to about 50 wt %, or any other value or range of values therein). In some embodiments, the base is present from about 0.01 wt % to about 5 wt % of the substantially anhydrous compositions.

The substantially anhydrous compositions can also comprise a salt. Salts useful in the substantially anhydrous compositions are those as described herein. The salt can be present in the substantially anhydrous compositions in an amount from 0 wt % to about 50 wt % (e.g., 0 to about 0.5 wt %, about 0.5 wt % to about 1 wt %, about 1 wt % to about 2 wt %, about 2 wt % to about 3 wt %, about 3 wt % to about 4 wt %, about 4 wt % to about 5 wt %, about 5 wt % to about 6 wt %, about 6 wt % to about 7 wt %, about 7 wt % to about 8 wt %, about 8 wt % to about 9 wt %, about 9 wt % to about 10 wt %, about 11 wt % to about 12 wt %, about 12 wt % to about 13 wt %, about 13 wt % to about 14 wt %, about 14 wt % to about 15 wt %, about 15 wt % to about 16 wt %, about 16 wt % to about 17 wt %, about 17 wt % to about 18 wt %, about 18 wt % to about 19 wt %, about 19 wt % to about 20 wt %, about 20 wt % to about 21 wt %, about 21 wt % to about 22 wt %, about 22 wt % to about 23 wt %, about 23 wt % to about 24 wt %, about 24 wt % to about 25 wt %, about 25 wt % to about 26 wt %, about 26 wt % to about 27 wt %, about 27 wt % to about 28 wt %, about 28 wt % to about 29 wt %, about 29 wt % to about 30 wt %, about 30 wt % to about 31 wt %, about 31 wt % to about 32 wt %, about 32 wt % to about 33 wt %, about 33 wt % to about 34 wt %, about 34 wt % to about 35 wt %, about 35 wt % to about 36 wt %, about 36 wt % to about 37 wt %, about 37 wt % to about 38 wt %, about 38 wt % to about 39 wt %, about 39 wt % to about 40 wt %, about 40 wt % to about 41 wt %, about 41 wt % to about 42 wt %, about 42 wt % to about 43 wt %, about 43 wt % to about 44 wt %, about 44 wt % to about 45 wt %, about 45 wt % to about 46 wt %, about 46 wt % to about 47 wt %, about 47 wt % to about 48 wt %, about 48 wt % to about 49 wt %, about 49 wt % to about 50 wt %, or any other value or range of values therein). In some embodiments, the salt is present from about 0.01 wt % to about 1 wt % of the substantially anhydrous compositions. In some embodiments, the substantially anhydrous compositions do not comprise a salt.

As stated herein, the substantially anhydrous compositions can comprise water. The amount of water in the substantially anhydrous compositions can range from 0 to about 10 wt % (e.g., 0 to about 0.5 wt %, about 0.5 wt % to about 1 wt %, about 1 wt % to about 2 wt %, about 2 wt % to about 3 wt %, about 3 wt % to about 4 wt %, about 4 wt % to about 5 wt %, about 5 wt % to about 6 wt %, about 6 wt % to about 7 wt %, about 7 wt % to about 8 wt %, about 8 wt % to about 9 wt %, about 9 wt % to about 10 wt %, or any other value or range of values therein). In certain embodiments, the substantially anhydrous compositions comprise less than about 5 wt % water (e.g., less than about 4 wt %, less than about 3 wt %, less than about 2 wt %, less than about 1 wt % less than about 0.9 wt %, less than about 0.8 wt %, less than about 0.7 wt %, less than about 0.6 wt %, less than about 0.5 wt %, less than about 0.4 wt %, less than about 0.3 wt %, less than about 0.2 wt %, less than about 0.1 wt %, or any other value or range of values therein or therebelow).

The substantially anhydrous compositions can further comprise an organic solvent. Organic solvents which can be present in the substantially anhydrous compositions include those described herein. The amount of organic solvent, if present, can be in an amount of 0 wt % to about 1 wt % (e.g., 0 to about 0.05 wt %, about 0.05 wt % to about 0.1 wt %, about 0.1 wt % to about 0.2 wt %, about 0.2 wt % to about 0.3 wt %, about 0.3 wt % to about 0.4 wt %, about 0.4 wt % to about 0.5 wt %, about 0.5 wt % to about 0.6 wt %, about 0.6 wt % to about 0.7 wt %, about 0.7 wt % to about 0.8 wt %, about 0.8 wt % to about 0.9 wt %, about 0.9 wt % to about 1.0 wt %, or any other value or range of values therein). In certain embodiments, the substantially anhydrous compositions do not comprise organic solvent.

The substantially anhydrous compositions can also comprise one or more other additives. Additives that which can be present in the substantially anhydrous compositions include those described herein. The additive(s) can be present in the substantially anhydrous compositions in amounts ranging from 0 to about 30% (e.g., 0 to about 0.5 wt %, about 0.5 wt % to about 1 wt %, about 1 wt % to about 2 wt %, about 2 wt % to about 3 wt %, about 3 wt % to about 4 wt %, about 4 wt % to about 5 wt %, about 5 wt % to about 6 wt %, about 6 wt % to about 7 wt %, about 7 wt % to about 8 wt %, about 8 wt % to about 9 wt %, about 9 wt % to about 10 wt %, about 11 wt % to about 12 wt %, about 12 wt % to about 13 wt %, about 13 wt % to about 14 wt %, about 14 wt % to about 15 wt %, about 15 wt % to about 16 wt %, about 16 wt % to about 17 wt %, about 17 wt % to about 18 wt %, about 18 wt % to about 19 wt %, about 19 wt % to about 20 wt %, about 20 wt % to about 21 wt %, about 21 wt % to about 22 wt %, about 22 wt % to about 23 wt %, about 23 wt % to about 24 wt %, about 24 wt % to about 25 wt %, about 25 wt % to about 26 wt %, about 26 wt % to about 27 wt %, about 27 wt % to about 28 wt %, about 28 wt % to about 29 wt %, about 29 wt % to about 30 wt %, or any other value or range of values therein). In certain embodiments, the additive is Type-S hydrated lime. In some embodiments, the substantially anhydrous compositions do not comprise an additive. In some embodiments, the substantially anhydrous compositions do not comprise lime.

In particular embodiments of the present invention, the substantially anhydrous compositions comprise a polysaccharide that is guar gum and plant material that is hemp seed. In other embodiments of the present invention, the substantially anhydrous compositions comprise plant material that is hemp seed and do not comprise a polysaccharide other than that present in or derived from the hemp seed. In other embodiments, the substantially anhydrous compositions comprise one or more of water, isopropanol, citric acid, Type S hydrated lime, sodium hydroxide, and sodium chloride.

Thus, in certain embodiments the present invention provides substantially anhydrous compositions comprising about 20 wt % to about 99.9 wt % of plant material, 0 to about 20 wt %, of a polysaccharide, 0% to about 1 wt % of an alcohol, 0% to about 50 wt % of a base, 0% to about 50 wt % of a salt, 0% to about 10 wt % of an acid, 0% to about 30 wt % of an additive, and 0% to about 10 wt % water. In certain embodiments, the substantially anhydrous composition comprises about 85 wt % to about 99.9 wt % of the plant material and 0 to about 10 wt % of the polysaccharide. In other embodiments, the substantially anhydrous composition of comprises about 95 wt % to about 99.9 wt % of the plant material and 0 to about 5 wt % of the polysaccharide. In certain embodiments, plant is a cereal. In other embodiments, the cereal is corn, rice, wheat, barley, sorghum, millet, rye, triticale, fonio, buckwheat, spelt or quinoa. In certain embodiments, the cereal is corn. In some embodiments, the plant material is corn gluten meal. In some embodiments, the plant material is soybean or hemp seed. In certain embodiments, the plant is cotton. In some embodiments the plant material comprises a plant protein. In other embodiments, the plant protein is prolamine, zein, hordein, or gliadin.

In some embodiments, the substantially anhydrous composition comprises a polysaccharide which is alginate, carrageenan, gum Arabic, tragacanth gum, guar gum, pectin, ghatti gum, xanthan gum, or mixtures thereof. In other embodiments, the substantially anhydrous composition does not comprise one or more of the aforementioned polysaccharides. In certain embodiments, the polysaccharide is 0 wt % to about 20 wt % of the substantially anhydrous composition. In other embodiments, the substantially anhydrous composition does not comprise polysaccharide other than that present in or derived from the plant material. In some embodiments, the substantially anhydrous composition further comprises an alcohol. In one embodiments, the alcohol is ethanol, methanol, or isopropanol. In other embodiments, the alcohol is isopropanol. In certain embodiments, the alcohol is about 0 wt % to about 1 wt % of the substantially anhydrous composition. In some embodiments, substantially anhydrous composition does not comprise an alcohol.

In certain embodiments, the substantially anhydrous composition further comprises a base. In some embodiments, the base is an inorganic base or an inorganic base. In certain embodiments, inorganic base is an alkali metal or alkaline earth metal base. In certain embodiments, the inorganic base is sodium hydroxide, lithium hydroxide, or potassium hydroxide. In certain embodiments, the base is 0 wt % to about 10 wt % of the substantially anhydrous composition. In some embodiments, substantially anhydrous composition does not comprise a base.

In certain embodiments, the substantially anhydrous composition further comprises a salt. In some embodiments, the salt is sodium chloride, potassium chloride, calcium chloride, magnesium chloride, ammonium chloride, sodium bromide, potassium bromide, calcium bromide, magnesium bromide, ammonium bromide, sodium iodide, potassium iodide, calcium iodide, magnesium iodide, ammonium iodide, sodium sulfate, potassium sulfate, calcium sulfate, magnesium sulfate, ammonium sulfate, potassium nitrate, calcium nitrate, magnesium nitrate, ammonium nitrate, or mixtures thereof. In certain embodiments, the salt is 0 wt % to about 10 wt % of the substantially anhydrous composition. In some embodiments, substantially anhydrous composition does not comprise a salt.

In some embodiments, the substantially anhydrous composition further comprises an acid. In other embodiments, the acids include inorganic acids. In certain embodiments, the inorganic acids include carbonic acid, sulfuric acid, or hydrochloric acid. In some embodiments, the acid is an organic acid. In certain embodiments, the acid is a C1-C20 organic acid. In certain embodiments, the acid is citric acid, formic acid, ascorbic acid, acetic acid, malic acid, adipic acid, tannic acid, lactic acid, fumaric acid, or mixtures thereof. In other embodiments, the acid is citric acid. In some embodiments, the acid is 0 wt % to about 10 wt % of the substantially anhydrous composition. In some embodiments, substantially anhydrous composition does not comprise an acid.

In certain embodiments, the substantially anhydrous composition further comprises an additive. In some embodiments, the additive is lime. In certain embodiments, the lime is Type S Hydrated Lime. In certain embodiments, the Type S Hydrated Lime is 0 wt % to about 10 wt % of the substantially anhydrous composition. In some embodiments, substantially anhydrous composition does not comprise an additive. In some embodiments, substantially anhydrous composition does not comprise lime.

In some embodiments, the substantially anhydrous composition comprises 0 wt % to about 10 wt % water. In other embodiments, the substantially anhydrous composition comprises 0 wt % to about 1 wt % water. In some embodiments, the substantially anhydrous composition does not comprise a polysaccharide other than the present in or derived from the plant material. In some embodiments, the plant material of the present substantially anhydrous composition is an acidified plant material. In other embodiments, the plant material of the present substantially anhydrous composition is a basified plant material.

Preparation of the Substantially Anhydrous Compositions

The aqueous compositions or extractants described herein can be dehydrated to form the present substantially anhydrous compositions. The substantially anhydrous compositions can later be reconstituted with a suitable solvent as described herein to provide the aqueous compositions or extractants. This allows for preparation of substantially anhydrous compositions, which can be easier and or less costly to handle, maintain or store. For example, once the present aqueous compositions or extractants as described herein have been prepared, their solvent can be removed to yield a substantially anhydrous composition. In preparing the present substantially anhydrous compositions, an acid or base as described herein can be added to adjust the pH prior to solvent removal. For example, the pH can be adjusted to from about 5 to about 14 (e.g., from about 5 to about 6, from about 6 to about 7, from about 7 to about 8, from about 8 to about 9, from about 9 to about 10, from about 10 to about 11, from about 11 to about 12, from about 12 to about 13, from about 13 to about 14, or any other value or range of values therein).

Any number of solvent removal techniques useful for obtaining a substantially anhydrous composition, e.g., from a Composition of the Invention can be used to prepare the prepare the substantially anhydrous compositions, including, but not limited to, vacuum drying, centrifugation, evaporation, freeze drying, air drying, lyophilization, convection oven drying or a combination thereof. One method for removing the solvent is vacuum drying, which safely removes and recovers the solvent while drying the product to provide the present substantially anhydrous compositions. The substantially anhydrous compositions can be further processed by grinding or milling to a desired mesh particle size. The substantially anhydrous compositions can also be subjected to particle-size reduction to form, for example, powders. The substantially anhydrous compositions can be subsequently admixed with water or organic solvent and one more additive, e.g., salt, sugar, a solvent, a surfactant, to provide a reconstituted aqueous composition or extractant for immediate or later use, Thus, in certain embodiments, the present invention provides a method of making a substantially anhydrous composition comprising about 20 wt % to about 99.9 wt % of plant material, 0 to about 20 wt %, of a polysaccharide, 0% to about 1 wt % of an alcohol, 0% to about 50 wt % of a base, 0% to about 30 wt % of a salt, 0% to about 10 wt % of an acid, 0% to about 30 wt % of an additive, and 0% to about 10 wt % water, comprising removing water from an aqueous composition of the present invention. In certain embodiments, removing water comprises drying. In certain embodiments, drying comprises heating the aqueous composition or subjecting the aqueous composition to reduced pressure. In some embodiments, the invention provides a method of making a substantially anhydrous composition comprising about 20 wt % to about 99.9 wt % of plant material, 0 to about 20 wt %, of a polysaccharide, 0% to about 1 wt % of an alcohol, 0% to about 50 wt % of a base, 0% to about 30 wt % of a salt, 0% to about 10 wt % of an acid, 0% to about 30 wt % of an additive, and 0% to about 10 wt % water, comprising removing water from an extractant of the present invention. In some embodiments, removing water from the extractant comprises drying the extractant. In some embodiments, drying comprises heating the extractant or subjecting the extractant to reduced pressure.

Cosmetic Compositions

In another aspect of the present invention, a Composition of the Invention is useful as a cosmetic composition and optionally comprises a cosmetically acceptable vehicle. A cosmetic Composition of the Invention can be in the form of a skin-care or dermo-pharmaceutical composition (e.g., toiletries, health and beauty aids and cosmeceuticals) used for cosmetic and personal care applications, such as for cosmetic purposes, purposes of hygiene or skin-care, or as a basis for delivery of one or more pharmaceutical ingredients. In some embodiments, a cosmetic Composition of the Invention is used for two or more of these purposes. For example, a medicated dandruff shampoo may be used as a personal care product, i.e., to provide clean hair, and at the same time have pharmacological properties.

The cosmetically acceptable vehicle may act as a diluent, dispersant or carrier of a Composition of the Invention. The cosmetically acceptable vehicle may facilitate distribution of Composition of the Invention when the composition is applied to the skin or hair. The vehicle may be aqueous, anhydrous, a gel, or an emulsion. In one embodiment, a cosmetic Composition of the Invention is aqueous or an emulsion, such as a water-in-oil or oil-in-water emulsion. Relatively volatile solvents may also serve as a cosmetically acceptable vehicle.

In some embodiments, the cosmetically acceptable vehicle comprises monohydric $C_1$-$C_3$ alkanols. These include ethyl alcohol, methyl alcohol and isopropyl alcohol. The amount of monohydric alkanol may range from 1 to 70%, from 10 to 50%, or between 15 and 40% by weight of the cosmetically acceptable vehicle or cosmetic Composition of the Invention.

Emollient materials may also serve as cosmetically acceptable vehicles. These may be in the form of silicone oils and synthetic esters. Amounts of the emollients may range anywhere from 0.1 to 50%, such as between 1 and 20% by weight of the cosmetically acceptable vehicle or cosmetic Composition of the Invention. Silicone oils may be cyclic or linear polydimethylsiloxanes and may contain from 3 to 9, or from 4 to 5, silicon atoms. Linear silicone materials typically have viscosities less than about 5 centistokes at 25° C., while cyclic materials typically have viscosities of less than about 10 centistokes. Silicone oils useful that may be used as an emollient material include polyalkyl siloxanes, polyalkylaryl siloxanes and polyether siloxane copolymers. Polyalkyl siloxanes include polydimethyl siloxanes with viscosities of from about 5 to about 25 million centistokes at 25° C. Emollients useful in the present compositions can also be polydimethyl siloxanes having viscosities from about 10 to about 400 centistokes at 25° C.

The emollient can be a stearate, such as PEG-40 stearate, glyceryl steatrate, sorbitan tristearate, stearyl alcohol or mixtures thereof. In some embodiments, the stearate is glyceryl stearate. In still other embodiments, the emollient is a vegetable or animal fat or oil, such as castor oil, hydrogenated castor oil, cocoa butter, safflower oil, cottonseed oil, corn oil, olive oil, cod liver oil, almond oil, avocado oil, palm oil, sesame oil, squalene, phytosqalene, kikui oil, chamomilla recutita (*matricaria*) flower oil, *hypericum perforatum* oil, soybean oil or *vitis vinifera* (grape) seed oil. The emolliant may also be an acetoglyceride ester, such as acetylated monoglycerides; an alkyl ester of fatty acids having 10 to 24 carbon atoms, such as methyl, isopropyl, and butyl esters of fatty acids, such as hexyl laurate, isohexyl laurate, ethylhexyl palmitate, isohexyl palmitate, isopropyl palmitate, octyl palmitate, decyloleate, isodecyl oleate, hexadecyl stearate decyl stearate, isopropyl isostearate, diisopropyl adipate, diisohexyl adipate, dihexyldecyl adipate, diisopropyl sebacate, lauryl lactate, myristyl lactate, and cetyl lactate; an alkenyl ester of fatty acids having 10 to 20 carbon atoms such as oleyl myristate, oleyl stearate, and oleyl oleate; a fatty acid having 10 to 20 carbon atoms such as pelargonic, lauric, myristic, palmitic, stearic, isostearic, hydroxystearic, oleic, linoleic, ricinoleic, arachidic, behenic, and erucic acids; a fatty alcohol having 10 to 20 carbon atoms such as lauryl, myristyl, cetyl, hexadecyl, stearyl, isostearyl, hydroxystearyl, oleyl, ricinoleyl, behenyl, erucyl, and 2-octyl dodecanyl alcohols; a fatty alcohol ether such as propoxylated fatty alcohols of 10 to 20 carbon atoms, such as lauryl, cetyl, stearyl, isostearyl, oleyl, and cholesterol alcohols, having attached thereto from 1 to 50 propylene oxide groups; a lanolin or lanolin derivative, such as lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated sorbitol lanolin, and liquid and semisolid lanolin absorption base; a polyhydric alcohol ester, such as ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters.

Wax esters, such as beeswax, spermaceti, myristyl myristate, stearyl stearate; vegetable waxes, such as carnauba and candelilla waxes; surface active silicone derivatives, such as cyclopentasiloxane PEG/PPG-18/18 dimethicone, dimethicone, dimethicone crosspolymer, cyclomethicone, cyclomethicone and dimethiconol; caprylic/capric triglycerides; and cholesterol fatty acid esters, can also be used as a cosmetically acceptable vehicle. The cosmetically acceptable vehicle can also be cetyl hydroxyethylcellulose, cetyl alcohol, ceteth-20 (a polyethylene glycol derivative of cetyl alcohol), cetearyl olivate, cetyl palmitate, sorbitan olivate, sorbitan palmitate, stearates, steareth-20 (polyethylene glycol ethers of stearic acid-octadecyl polyoxyethylene ether), steareth-25 or mixtures thereof.

Humectants may also be utilized as a cosmetically acceptable vehicle. The humectant can aid in increasing the effectiveness of the emollient, such as by providing skin benefits. The humectant may be a polyhydric alcohol. Polyhydric alcohols include glycerol, polyalkylene glycols, such as alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. In one embodiment, the humectant is propylene glycol or sodium hyaluronate. The amount of humectant may range anywhere from 0.5 to 30%, such as between 1 and 15% by weight of the cosmetically acceptable vehicle or cosmetic Composition of the Invention.

Thickeners may also be utilized as part of the cosmetically acceptable vehicle. Thickeners include crosslinked acrylates (e.g. Carbopol 982), hydrophobically-modified acrylates (e.g. Carbopol 1382), cellulosic derivatives and natural gums. Among cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, such as from 0.001 to 1% or from 0.01 to 0.5% by weight of the cosmetically acceptable vehicle or cosmetic Composition of the Invention.

Collectively, the water, solvents, silicones, esters, fatty acids, humectants and/or thickeners may constitute the cosmetically acceptable vehicle in amounts from 1 to 99.9%, such as from 80 to 99% by weight. The cosmetically acceptable vehicle may constitute between about 0.05 to 15% of the total weight of the cosmetic Composition of the Invention. In some embodiments, the cosmetically acceptable vehicle constitutes between 0.05% and 10% or between 0.05% and 8%, or between 0.05% and 7%, or between 0.05% and 6%, or between 0.05% and 5% of the total weight of the cosmetic Composition of the Invention. Variations and other appropriate vehicles will be apparent to the skilled artisan and are appropriate for use in the present invention.

In some embodiments, a cosmetic Composition of the Invention can comprise an anti-acne agent, anti-aging agent, antibacterial agent, anti-viral agent, anticoagulant, antiplatelet agent, anti-cellulites agent, antidandruff agent, antifungal agent, anti-inflammatory agent, anti-irritation agent, antimicrobial agent, antioxidant agent, antiperspirant agent, antiseptic agent, cell stimulant, cleansing agent, conditioner, deodorant, depilatory, detergent, exfoliant, glosser, hair conditioner, hair set resin, hair sheen agent, hair waving agent, humectant, moisturizer, ointment base, perfume, skin calming agent, skin cleanser, skin conditioner, skin healing agent, skin lightening agent, skin protectant, skin smoothing agent, skin softening agent, skin soothing agent, sunscreen agent, tanning accelerator, or vitamin, such as those described in the Cosmetic, Toiletry, and Fragrance Association (CTFA) Cosmetic Ingredient Handbook (Second Edition, Eds. John A. Wenninger and Gerald N. McEwen, Washington, D.C., 1992; see also CTFA Cosmetic Ingredient Dictionary, 4th Edition, Washington, D.C., 1991; International Cosmetic Ingredient Dictionary & Handbook, 14th Edition, 2012, published by the Personal Care Products Council, each of which are incorporated by reference in its entirety).

Thus, in some embodiments, a cosmetic Composition of the Invention can comprise an ingredient from the CTFA Handbook. The ingredient can be from ingredient classes that include: fragrances (artificial and natural), dyes and color ingredients (e.g. Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, emulsifiers, stabilizers, lubricants, solvents, moisturizers (e.g. emollients, humectants, film formers, occlusive agents, and agents that affect the natural moisturization mechanisms of the skin), water-repellants, UV absorbers (physical and chemical absorbers such as paraaminobenzoic acid ("PABA") and corresponding PABA derivatives, titanium dioxide, zinc oxide), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. aloe vera, chamomile, cucumber extract, ginkgo biloba, ginseng, and rosemary), anti-microbial agents, antioxidants (e.g. BHT), chelating agents (e.g. disodium EDTA and tetrasodium EDTA), preservatives (e.g. methylparaben and propylparaben), pH adjusters (e.g. sodium hydroxide and citric acid), absorbents (e.g. aluminum starch octenylsuccinate, kaolin, corn starch, oat starch, cyclodextrin, talc, and zeolite), skin bleaching and lightening agents (e.g. hydroquinone and niacinamide lactate), humectants (e.g. propylene glycol, butylene glycol, pentylene glycol, sorbitol, urea, and manitol), exfoliants (e.g. alpha-hydroxyacids, and beta-hydroxyacids such as lactic acid, glycolic acid, and salicylic acid; and salts thereof) waterproofing agents (e.g. magnesium/aluminum hydroxide stearate), skin conditioning agents (e.g. aloe extracts, allantoin, bisabolol, ceramides, dimethicone, hyaluronic acid, and dipotassium glycyrrhizate), thickening agents (e.g. substances which that can increase the viscosity of a composition such as carboxylic acid polymers, cross-linked polyacrylate polymers, polyacrylamide polymers, polysaccharides, and gums), and silicone containing compounds (e.g. silicone oils and polyorganosiloxanes).

Various types of additional ingredients may be present in a cosmetic Composition of the Invention, such as an anti-sebum agent (e.g. talc or silica), anti-perspirant agent (e.g. astringent salt), or anti-aging agent (e.g. retinoid). The astringent salt may be an inorganic or organic salt of aluminum, zirconium, zinc or mixtures thereof. The salt can be an aluminum complex, such as aluminum hydroxide, aluminum halides, aluminum hydroxyhalides, zirconyl oxyhalides, zirconyl hydroxyhalides or mixtures of these salt materials. For example, the salt can be aluminum chloride, aluminum chlorohydrate, aluminum chlorohydrex, aluminum chlorohydrex PEG, aluminum chlorohydrex PG, aluminum dichlorohydrate, aluminum dichlorohydrex PEG, aluminum dichlorohydrex PG, aluminum sesquichlorohydrate, aluminum sesquichlorohydrex PEG, aluminum sesquichlorohydrex PG, aluminum sulfate, aluminum zirconium octachlorohydrate, aluminum zirconium octachlorohydrex GLY (abbreviation for glycine), aluminum zirconium pentachlorohydrate, aluminum zirconium pentachlorohydrex GLY, aluminum zirconium tetrachlorohydrate, aluminum zirconium trichlorohydrate, aluminum zirconium tetrachlorohydrate GLY, and aluminum zirconium trichlorohydrate GLY. Amounts of the salt may range from about 0.000001% to about 20%, from about 0.10% to about 18%, from about 1 to about 15%, or about 2% to about 3% by weight of the cosmetic Composition of the Invention.

A cosmetic Composition of the Invention may also include a retinoid. Retinoids can increase collagen synthesis by dermal fibroblasts, resulting in protection from sun damage and smoothening of wrinkled skin. The retinoid can be a retinoic acid, retinol, retinal, or retinyl ester, such as 13-cis retinoic acid, all-trans retinoic acid, all-trans-retinol, 13-cis-retinol, 11-cis-retinol, 9-cis-retinol, 3,4-didehydro-retinol. Preferred isomers are all-trans-retinol, 13-cis-retinol, 3,4-didehydro-retinol, and 9-cis-retinol. Retinyl esters that can be included in a cosmetic Composition of the Invention include $C_1$-$C_{30}$ esters of retinol, such as $C_2$-$C_{20}$ esters, such as $C_2$, $C_3$, or $C_{16}$ esters. Examples of retinyl esters include retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadecanoate, retinyl stearate, retinyl isostearate, retinyl nonadecanoate, retinyl arachidonate, retinyl behenate, retinyl linoleate, retinyl oleate, retinyl lactate, retinyl glycolate, retinyl hydroxy caprylate, retinyl hydroxy laurate, retinyl tartarate. The retinoids may present in an amount of from 0.001% to 10%, such as from 0.01% to 1% or from 0.01% to 0.05% weight of a cosmetic Composition of the Invention.

A beta-hydroxy acid, salicylic acid, or zinc pyrithione can also be used in a cosmetic Composition of the Invention.

A cosmetic Composition of the Invention can have UVA and UVB absorption properties, such as by comprising a UV absorption agent. A cosmetic Composition of the Invention can also comprise a sunscreen agent. Examples of UV absorption and sunscreen agents include para-aminobenzoic acid (PABA), PABA esters (e.g. glyceryl PABA, amyldimethyl PABA and octyldimethyl PABA), butyl PABA, ethyl PABA, ethyl dihydroxypropyl PABA, benzophenones (e.g. xybenzone, sulisobenzone, benzophenone, and benzophenone-1 through 12), cinnamates (e.g. octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (e.g. homomethyl salicylate, benzyl salicylate, glycol salicylate, isopropylbenzyl salicylate), anthranilates, ethyl urocanate, homosalate, octisalate, dibenzoylmethane derivatives, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidenecamphor, and isopentyl 4-methoxycinnamate. Other examples include kaolin, talc, petrolatum and metal oxides (e.g. titanium dioxide and zinc oxide). The amount of sunscreen in a cosmetic Composition of the Invention can vary depending upon the degree of protection desired from the sun's UV radiation.

A cosmetic Composition of the Invention can also comprise an antioxidant, such as acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfate, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocophersolan, tocopheryl linoleate, tocopheryl nicotinate, tocopheryl succinate, or tris(nonylphenyl) phosphite.

A cosmetic Composition of the Invention can also comprise a preservative. Suitable preservatives may include alkyl esters of p-hydroxybenzoic acid, hydantoin derivatives, propionate salts, and a variety of quaternary ammonium compounds. Other preservatives that may be used include methyl paraben, propyl paraben, phenoxyethanol or benzyl alcohol. Preservatives may be in amounts ranging from about 0.1% to 2% by weight of the cosmetic Composition of the Invention.

A cosmetic Composition of the Invention can comprise an anti-microbial agent. In some embodiments, the antimicrobial is a bacteriostatic or bactericidal agent, such as Asiatic acid, the monoethanolamine salt of 1-hydroxy-4-methyl 6-trimethylpentyl-2-pyridone; citronellic acid, perillic acid; glyceryl 2-ethylhexyl ether; glyceryl caprylate/caprate; sodium calcium phosphosilicate; silver-based particles; hop cone extract; St.-John's Wort extract; the mixture of extracts of roots of *Scutellaria baicalensis*, of *Paeonia suffruticosa* and *Glycyrrhiza glabra*; argan tree extract; bearberry leaf extracts; 10-hydroxy-2-decanoic acid, sodium ursolate, azelaic acid, diiodomethyl p-tolyl sulfone, malachite powder, zinc oxide, octadecenedioic acid; ellagic acid; 2,4,4'-trichloro-2'-hydroxydiphenyl ether (Triclosan); 2,4-dichloro-2'-hydroxydiphenyl ether, 3',4',5'-trichlorosalicylanilide, 1-(3',4'-dichlorophenyl)-3-(4'-chlorophenyl)urea (Triclocarban); 1-(3',4'-dichlorophenyl)-3-(4'-chlorophenyl) urea; 3,4,4'-trichlorocarbanilide; 3',4',5'-trichlorosalicylanilide, phenoxyethanol, phenoxypropanol, phenoxyisopropanol, hexamidine isethionate, metronidazole and salts thereof, miconazole and salts thereof, itraconazole, terconazole, econazole, ketoconazole, saperconazole, fluconazole, clotrimazole, butoconazole, oxiconazole, sulfaconazole, sulconazole, terbinafine, ciclopirox, ciclopiroxolamine, undecylenic acid and salts thereof, benzoyl peroxide, 3-hydroxybenzoic acid, 4-hydroxybenzoic acid, phytic acid, N-acetyl-L-cysteine, lipoic acid, azelaic acid and salts thereof, arachidonic acid, resorcinol, 3,4,4'-trichlorocarbanalide, octoxyglycerine, octanoylglycine, caprylyl glycol, 10-hydroxy-2-decanoic acid, dichlorophenylimidazoldioxolane and derivatives thereof, iodopropynyl butylcarbamate, 3,7, 11-trimethyldodeca-2,5,10-trienol (Farnesol), phytosphingosines; quaternary ammonium salts, cetylpyridinium salts, sodium cocoamphoacetate, disodium diacetate, betaines, sodium lauryl ether sulfate, decyl glucoside, branched $C_{12-13}$ dialkyl malates, propylene glycol monoesters, lauryldimethylamine betaine, polyquaternary ammoniums, quaternary ammonium salts, for instance cetyltrimethylammonium salts or cetylpyridinium salts; chlorhexidine and salts; diglyceryl monocaprate, diglyceryl monolaurate or glyceryl monolaurate; polyhexamethylene biguanide salts; or mixtures thereof.

A cosmetic Composition of the Invention can also comprise a moisturizing agent. The moisturizing agent can facilitate hydration of the skin by inhibiting or preventing loss of water from the skin, absorbing water from the atmosphere and hydrating the skin, or enhancing the skin's own ability to absorb water directly from the atmosphere, or a combination thereof. Suitable moisturizing agents may include hydrophobic agents, hydrophilic agents, and combinations thereof.

Examples of moisturizing agents that are hydrophobic include ceramide, borage oil (linoleic acid), tocopherol (Vitamin E), tocopherol linoleate, dimethicone, glycerine, and mixtures thereof. Examples of moisturizing agents that are hydrophilic agents include hyaluronic acid, sodium peroxylinecarbolic acid (sodium PCA), wheat protein (e.g., laurdimonium hydroxypropyl hydrolyzed wheat protein), and mixtures thereof. Other moisturizing agents include panthenol; primrose oil; GLA 3 and other fish oils that may include, for example, the omega-3 and omega-6 oils and/or linoleic acid; and flax seed oil.

In another embodiment, a cosmetic Composition of the Invention comprises an exfoliant. The exfoliant may be a mechanical or chemical exfoliant. The exfoliant may be an enzymatic exfoliant, such as fruit enzymes. Examples of enzymatic exfoliants include papain, from papaya, and bromalein, from pineapple. The exfoliant may be an acidic exfoliant, such as salicylic acid, glycolic acid, citric acid, malic acid, alpha hydroxy acid, or beta hydroxyl acid.

In certain aspects, the concentrations and combinations of the ingredients of a cosmetic Composition of the Invention is selected such that the concentrations and combinations are chemically compatible.

The cosmetic Composition of the Invention can have a pH from about 5.5 to about 9.0 or from about 6.0 to about 8.0. In some embodiments, the pH of the Composition of the Invention further comprising a cosmetically acceptable vehicle is about 7.0, 7.1, 7.2, 7.3, 7.4, 7.5, 7.6, 7.7, 7.8, 7.9 or 8.0. In one embodiment, the pH of the cosmetic Composition of the Invention is about 7.4.

A cosmetic Composition of the Invention can be encapsulated for delivery to a target area such as the skin, teeth or hair. Encapsulation techniques include the use of liposomes, vesicles, or nanoparticles that are useful as delivery vehicles to deliver a cosmetic Composition of the Invention to skin, teeth or hair.

A cosmetic Composition of the Invention can be in the form of a lotion; an ointment; a gel; a cream; a shampoo; a moisturizer; a sunscreen; a cream; a stick; a spray; an aerosol; a foam; a paste; a mousse; a dentrifice; a solid, semi-solid, or liquid make-up; a foundation; or an eye make-up. Examples of products that can incorporate the cosmetic Composition of the Invention include hand treatment products, decollete treatment products, sunless skin tanning products, hair products (e.g., shampoos, conditioners, colorants, dyes, bleaches, straighteners, and permanent wave products), fingernail products, moisturizing creams, skin creams and lotions, softeners, day lotions, gels, ointments, foundations, night creams, lipsticks, lip balms, cleansers, toners, masks, deodorants, antiperspirants, exfoliating compositions, shaving-related products (e.g., creams and aftershaves), pre-moistened wipes and washcloths, tanning lotions, bath products (e.g. oils), foot care products (e.g. powders and sprays), skin colorant, make-up products (e.g. foundations, blushes, eye shadows, eye liners, lip colors, mascaras), baby products (e.g., baby lotions, oils, shampoos, powders and wet wipes), pet products (e.g., shampoos, powders and wet wipes) and skin peel products.

Additionally, the cosmetic Composition of the Invention can be formulated as leave-on or rinse-off products.

The cosmetic Composition of the Invention can be in any form, e.g. formulated as a toner, gel, lotion, a fluid cream, or a cream. The cosmetic Composition of the Invention can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the cosmetic Composition of the Invention is a cream, it can be stored in a non-deformable bottle or squeeze container, such as a tube or a lidded jar. The cosmetic Composition of the Invention may also be included in capsules, such as those described in U.S. Pat. No. 5,063,057.

Articles

Another aspect of the present invention is an article containing a Composition of the Invention. The article can be a bandage, absorptive dental roll, tampon, sanitary napkin, diaper, body urinal, underarm perspiration pad, breast pad, disposable hat band, wiping cloth, tissue wipe, pre-moistened towelette, mattress pad, undersheet, surgical dressing, toilet paper or facial tissue. In some embodiments, the article contains an effective amount of a Composition of the Invention. In some embodiments, the article is an article of manufacture.

Accordingly, in one embodiment, a Composition of the Invention is applied to an article. In one embodiment, the article comprises a woven or unwoven material. The article can be a cellulose product, such as the gauze or other absorbent dressings. In another embodiment, the article is wound dressing, a burn dressing, or a gauze roll. In some embodiments, the article is a bandage. The bandage can be of the type used on acute wounds, minor wounds, burn wounds and irritations. In another embodiment, the article is a fabric, such as cotton, cloth, rayon, nylon, wool, surgical gauze, burlap, or paper.

In some embodiments, the article is a commercially available product, such as gauze and surgical sponge products manufactured by Johnson & Johnson Company (J&J). In another embodiment, the article is a commercially-available fabric material, such as a cotton knitted tee-shirt material, cloth diaper material, terry wash-cloth material, non-woven wiping cloth, or cellulose kitchen sponge. In some embodiments, the article comprises cotton, rayon or polyester. In some embodiments, the article is a cotton blend. In other embodiments, the article is 100% cotton.

In some embodiments, the article is a bandage or dressing containing a Composition of the Invention, and further containing a hemostatic agent. Examples of hemostatic agents include antifibrinolytics, vitamin K, fibrinogen, or styptics. In some embodiments, the hemostatic agent is kaolin, microfibrillar collagen hemostat, zeolite or chitosan. In some embodiments, the bandage or dressing further contains an antibiotic, antifungal agent, antimicrobial agent, anti-inflammatory agent, analgesic, antihistamine, or compound containing silver or copper ions.

Pharmaceutical Compositions

In another aspect of the present invention, a Composition of the Invention is useful as a pharmaceutical composition and optionally comprises a pharmaceutically acceptable carrier, vehicle or excipient.

The pharmaceutically acceptable excipient can provide the form for proper administration to the subject. Such pharmaceutically acceptable excipients can be liquids, such as water and oil, including those of petroleum, animal, vegetable, or synthetic origin, such as peanut oil, soybean oil, mineral oil, sesame oil and the like. The pharmaceutically acceptable excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when a Composition of the Invention is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also comprise minor amounts of wetting or emulsifying agents, or pH buffering agents.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutical composition is in the form of a capsule (see e.g. U.S. Pat. No. 5,698,155). Other examples of suitable pharmaceutical excipients are described in Remington's Pharmaceutical Sciences 1447-1676 (Alfonso R. Gennaro eds., 19th ed. 1995), incorporated herein by reference.

In one embodiment, a pharmaceutical Composition of the Invention is formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving a pharmaceutical Composition of the Invention are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the pharmaceutical Compositions of the Invention can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection.

Generally, the ingredients are supplied either separately or mixed together in unit dosage form, for example, as a dry lyophilized-powder or water-free concentrate in a hermetically sealed container such as an ampule or sachette indicating the quantity of active agent. Where a pharmaceutical Composition of the Invention is to be administered by infusion, it can be dispensed, for example, with an infusion bottle containing sterile pharmaceutical grade water or saline. Where the pharmaceutical Composition of the Invention is administered by injection, an ampule of sterile water for injection or saline can be provided so that the ingredients can be mixed prior to administration.

Pharmaceutical Compositions of the Invention can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with a Composition of the Invention. The present invention thus provides single unit dosage forms suitable for oral administration such as, but not limited to, tablets, capsules, gelcaps, and caplets that are adapted for controlled- or sustained-release.

Controlled- or sustained-release of an active ingredient can be stimulated by various conditions, including but not limited to, changes in pH, changes in temperature, concentration or availability of enzymes, concentration or availability of water, or other physiological conditions or compounds. The amount of the Composition of the Invention that is effective in the treatment or prevention of a disease can be determined by standard clinical techniques. In addition, in vitro or in vivo assays can optionally be employed to help identify optimal dosage ranges. The precise dose to be employed can also depend on the route of administration, and the seriousness of the condition being treated and can be decided according to the judgment of the practitioner and each subject's circumstances in view of, e.g., published clinical studies. Suitable effective dosage amounts, however, range from about 10 micrograms to about 5 grams about every 4 hours, although they are typically about 500 mg or less per every 4 hours. In one embodiment, the effective dosage is about 0.01 mg, 0.5 mg, about 1 mg, about 50 mg, about 100 mg, about 200 mg, about 300 mg, about 400 mg, about 500 mg, about 600 mg, about 700 mg, about 800 mg, about 900 mg, about 1 g, about 1.2 g, about 1.4 g, about 1.6 g, about 1.8 g, about 2.0 g, about 2.2 g, about 2.4 g, about 2.6 g, about 2.8 g, about 3.0 g, about 3.2 g, about 3.4 g, about 3.6 g, about 3.8 g, about 4.0 g, about 4.2 g, about 4.4 g, about 4.6 g, about 4.8 g, and about 5.0 g, every 4 hours.

In various embodiments, a suitable dosage may be in a range of about 0.1 mg/kg to about 100 mg/kg of body weight of the subject, for example, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg body weight, inclusive of all values and ranges therebetween.

Equivalent dosages can be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The effective dosage amounts described herein refer to total amounts administered; that is, if more than Composition of the Invention is administered, the effective dosage amounts correspond to the total amount administered.

Pharmaceutical Compositions of the Invention can be prepared according to conventional mixing, granulating or coating methods, respectively, and the present compositions can comprise, in one embodiment, from about 0.1% to about 99%; and in another embodiment from about 1% to about 70% of the compound of the invention by weight or volume.

The dosage regimen utilizing a pharmaceutical Composition of the Invention can be selected in accordance with a variety of factors including type, species, age, weight, sex and medical condition of the subject; the severity of the condition to be treated; the route of administration; the renal or hepatic function of the subject; and the specific compound of the invention employed. A pharmaceutical Composition of the Invention can be administered in a single daily dose, or the total daily dosage can be administered in divided doses of two, three or four times daily. Furthermore, a pharmaceutical Composition of the Invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of compound of the invention ranges from about 0.1% to about 15%, w/w or w/v. The pharmaceutical Composition of the Invention can be assayed in vitro or in vivo for the desired therapeutic or prophylactic activity prior to use in humans. Animal model systems can be used to demonstrate safety and efficacy.

In certain embodiments, a pharmaceutical Composition of the Invention is administered to a human that has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In some embodiments, a pharmaceutical Composition of the Invention is administered to a human infant. In other embodiments, a pharmaceutical Composition of the Invention is administered to a human toddler. In other embodiments, a pharmaceutical Composition of the Invention is administered to a human child. In other embodiments, a pharmaceutical Composition of the Invention is administered to a human adult. In yet other embodiments, a pharmaceutical Composition of the Invention is administered to an elderly human.

Methods

In one aspect the present invention provides methods for extracting a substance from a substrate comprising contacting the substrate with a Composition of the Invention under conditions effective for extracting at least some of the substance from the substrate. In one embodiment, "extracting" as used herein includes removing a substance from the surface of a substrate. In another embodiment, "extracting" as used herein includes extracting the substance from pores, fractures, cracks, fissures, crevices or interstitial spaces of a substrate.

Accordingly, in one aspect the present invention provides methods for extracting a substance, such as a substance comprising a protein, lipid, wax, fatty acid, fatty alcohol or hydrocarbon, from a substrate, comprising contacting the substrate with a Composition of the Invention under conditions effective for extracting at least some of the substance. In some embodiments, the substance is a protein, lipid, wax, fatty acid, fatty alcohol or hydrocarbon-containing substance. In one embodiment, the hydrocarbon-containing substance is a hydrocarbon. In one embodiment, extracting includes removing a protein, lipid, wax, fatty acid, fatty alcohol or hydrocarbon-containing substance from the surface of a substrate. In another embodiment, extracting includes extracting the protein, lipid, wax, fatty acid, fatty alcohol or hydrocarbon-containing substance from pores, fractures, cracks, fissures, crevices or interstitial spaces of a substrate.

Another aspect of the present invention is a method for extracting a substance comprising contacting the substrate with a Composition of the Invention under conditions effective for extracting at least some of the substance, wherein the substance is tar, tar sand, coal tar, or asphalt. In one embodiment, extracting includes removing tar, tar sand or coal tar from the surface of a substrate. In another embodiment, extracting includes extracting the tar, tar sand, coal tar or asphalt from pores, fractures, cracks, fissures, crevices or interstitial spaces of a substrate. In one embodiment, the substrate is a shingle.

In another aspect, the present invention provides methods for remediating a substrate, comprising contacting the substrate with a Composition of the Invention under conditions effective for remediating the substrate. As used herein, the term "remediating" includes extracting at least some substance, such as a protein, lipid, wax, fatty acid, fatty alcohol or hydrocarbon-containing substance from a substrate. In some embodiments, remediating includes extracting at least some substance, such as tar, tar sand, coal tar or asphalt from a substrate, such as shingles.

Remediating can include purifying water such that it becomes potable, suitable for swimming or non-toxic to aquatic species; converting contaminated soil to that which is useful as farmland or for real estate; converting oil sand to sand that is suitable for commercial or recreational use, etc. Thus, remediating a substrate can substantially improve the quality of a substrate, for example, rendering it non-toxic. In some embodiments, remediating the substrate includes removing a substance from the surface of a substrate, or extracting the substance from pores, fractures, cracks, fissures or crevices in a substrate. The present methods are useful for remediating environmentally contaminated sites, soils or animals. Accordingly, in certain embodiments, the present invention provides methods for remediating a substrate, comprising contacting the substrate with an aqueous composition of the present invention under conditions effective for remediating the substrate.

The substance can comprise a hydrocarbon, a protein, lipid, wax, fatty acid or fatty alcohol. The substance can be a hydrocarbon, a protein, lipid, wax, fatty acid or fatty alcohol. In some embodiments, the substance is tar, tar sand, coal tar, asphalt, or grease. In yet other embodiments, the substance can be a bodily fluid, such as blood or sebum. In certain embodiments, the substrate is soil, sand, beach sand, oil sand, heavy-oil plastic, mineral, bone, teeth, sand, rock, wood, paper, skin, water, gravel, mud, clay, plant, hair, fabric, glass, porcelain, concrete or metal. The substrate can be a solid or a liquid. Where the substrate is a solid, it can be a solid comprising a pore, fracture, crack, fissure or crevice; a smooth, non-porous solid; or a particulate material such as a powder, sand, gravel, silt or sediment. In certain embodiments, the substrate is water. In one embodiment, the substrate is a waterbody. A waterbody can include ponds, lakes, streams, rivers, oceans, seawater, fresh water, salt water, brackish water, groundwater, wastewaster, and the like.

In another embodiment, the substrate is a blood vessel, including the wall of a blood vessel. The blood vessel can be an artery, arteriole, venule, vein, or capillary. The substance can be any substance described herein, particularly a lipid, for example a sterol, for example cholesterol, a low-density lipid (LDL), or high-density lipid (HDL). Thus, in certain embodiments, the present methods are useful to extract, remove or decrease the amount of a substance from a blood vessel. In certain embodiments, the present invention provides methods for extracting, removing, or decreasing the amount of at least some of the substance from a blood vessel of a subject, comprising administering to a subject in need thereof an effective amount of a Composition of the Invention. The subject can be a mammal, such as a human. In some embodiments, the subject has dyslipidemia, high blood pressure or hypertension. The method can comprise administering a pharmaceutical Composition of the Invention to the subject. In some embodiments, a therapeutically effective amount of the pharmaceutical Composition of the Invention is administered to the subject. A therapeutically effective amount can be an amount that extracts or removes at least some of a substance from the blood vessel of a subject. In some embodiments, a therapeutically effective amount is an amount that decreases the amount or concentration of a substance in a subject, for example, in a subject's blood vessel. In some embodiments, the substance is a cholesterol, LDL, HDL, or any combination thereof. In some embodiments, a therapeutically effective amount is an amount of a Composition of the Invention that decreases the blood pressure in a subject.

In another embodiment, the substrate is fabric. Fabric can include any woven material or fibers, including natural fibers such as cotton, wool, linen, silk, hemp, jute, etc., and synthetic fibers including rayon, polyester, nylon, etc. Thus, in certain embodiments, the present methods may be employed to extract a protein, lipid, wax, fatty acid, fatty alcohol or hydrocarbon-containing substance from fabric or woven materials. In some embodiments, a bodily fluid is extracted from the fabric or woven materials. In some embodiments, the present invention provides a laundry detergent comprising a Composition of the Invention. In other embodiments, a Composition of the Invention is in the form of a laundry detergent. In certain embodiments, the present invention provides a method for extracting a protein, lipid, wax, fatty acid, fatty alcohol or hydrocarbon-containing substance from fabric comprising contacting the fabric with a laundry detergent comprising a Composition of the Invention under conditions effective for removing the substance from the fabric.

Accordingly, in another aspect, the present invention provides laundry detergents comprising an aqueous composition of the present invention. In some embodiments, the laundry detergent comprises an extractant of the present invention. In other embodiments, the laundry detergent comprises a substantially anhydrous composition of the present invention. In some embodiments, the invention further provides a method for removing a substance from fabric comprising contacting the fabric with the laundry detergent comprising a Composition of the Invention under conditions effective for removing the substance from the fabric.

In another aspect, the present invention provides cleaning agents comprising an aqueous composition of the present invention. In some embodiments, the cleaning agent comprises an extractant of the present invention. In other embodiments, the cleaning agent comprises a substantially anhydrous composition of the present invention. In some embodiments, the present invention provides a method for removing a substance from a substrate comprising contacting the substrate with a cleaning agent comprising a Composition of the Invention under conditions effective for removing the substance from the substrate. In some embodiments, a Composition of the Invention is in the form of a cleaning agent.

In certain embodiments, the present methods may be employed to clean a substrate by extracting a protein, lipid, wax, fatty acid, fatty alcohol or hydrocarbon-containing substance from the substrate. In other embodiments, the present methods is employed to remediate a substrate by extracting a protein, lipid, wax, fatty acid, fatty alcohol or hydrocarbon-containing substance from the substrate. The substrate can be a piece of machinery or equipment, such as that of a factory or refinery. In other embodiments, the substrate is a part of a house or building, such as the carpet, plumbing, floor, walls, windows, or roof. In some embodiments, the substrate is a bicycle, automobile, or boat. In other embodiments, the substrate is a piece of furniture, an instrument, an appliance, a grill or cookware.

In another aspect, the present invention provides paint thinners, paint cleaners or paint additives comprising an aqueous composition of the present invention. In some embodiments, the paint thinner, paint cleaner or paint additive comprises an extractant of the present invention. In other embodiments, the paint thinner, paint cleaner or paint additive comprises a substantially anhydrous composition of the present invention. One aspect of the present invention is a composition comprising paint and a Composition of the Invention. Another aspect of the invention is a method of preparing paint comprising admixing a paint and a Composition of the Invention. In one embodiment, the paint is an oil-based paint. In another embodiment, the paint is a water-based paint.

Another aspect of the invention is a paint thinner or cleaner comprising a Composition of the Invention. A paint thinner or cleaner comprising a Composition of the Invention can be useful for reducing or thinning coatings and water and oil based paint material, and can also be useful for cleaning paint. In some embodiments, the present invention provides methods for removing or thinning paint, comprising contacting paint with a Composition of the Invention under conditions effective for thinning paint. In another embodiment, a method for removing paint from a substrate comprises contacting the substrate with a Composition of the Invention under conditions effective for removing or extracting paint from a substrate.

In certain embodiments, the present methods may be employed to clean a substrate by removing paint from the substrate. In some embodiments, the methods comprise contacting a painted substrate with a Composition of the Invention under conditions that are effective to remove paint from the substrate. In other embodiments, the present method is employed to remediate a substrate by extracting paint from the substrate. The substrate can be a piece of machinery or equipment, such as that of a factory or refinery. In other embodiments, the substrate is a part of a house or building, such as the carpet, plumbing, floor, walls, windows, or roof. In some embodiments, the substrate is a bicycle, automobile, or boat. In other embodiments, the substrate is a piece of furniture, an instrument, an appliance, a grill or cookware. In some embodiments the substrate is a paintbrush or roller.

Another aspect of the invention is a polish or polishing composition comprising a Composition of the Invention. A polish or polishing composition comprising a Composition of the Invention can be useful in polishing a substrate. In some embodiments, the substrate is wood, ceramic, glass, stone, plastic, or metal. Also provided herein is a method of using the polish or polishing composition. In some embodiments, the present invention provides methods for polishing a substrate, comprising contacting a substrate with a Composition of the Invention under conditions effective for polishing a substrate. In some embodiments, the Composition of the Invention is in the form of a polish or polishing composition.

Another aspect of the invention is a mold and mildew remover comprising a Composition of the Invention. A mold and mildew remover comprising a Composition of the Invention can be useful in removing mold or mildew from a substrate or killing mold and mildew on a substrate, or for preventing or retarding growth or regrowth of mold and mildew on a substrate which has been contacted with a Composition of the Invention. In some embodiments, the substrate is wood, grout, ceramic, glass, stone, cement, plastic, or metal. Also provided herein is a method of using the mold and mildew remover comprising a Composition of the Invention. In some embodiments, the present invention provides methods for removing mold or mildew, comprising contacting a substrate having mold or mildew with a Composition of the Invention under conditions that are effective to remove at least some of the mold or mildew. In some embodiments, the present invention provides methods for inhibiting the growth of mold or mildew, comprising contacting a substrate having mold or mildew with a Composition of the Invention under conditions that are effective to inhibit the growth of the mold or mildew.

In another aspect, the present invention provides degreasing agents comprising an aqueous composition of the present invention. In some embodiments, the degreasing agent comprises an extractant of the present invention. In other embodiments, the degreasing agent comprises a substantially anhydrous composition of the present invention. In some embodiments, the invention provides methods for removing grease from a substrate, comprising contacting the substrate with a Composition of the Invention under conditions effective for removing grease from the substrate.

In certain embodiments, the present methods may be employed to degrease a substrate by extracting grease from the substrate. In other embodiments, the present method is employed to remediate a substrate by extracting grease from the substrate. The substrate can be a piece of machinery or equipment, such as that of a factory or restaurant. In other embodiments, the substrate is a part of a house or building, such as the carpet, plumbing, floor, walls, or windows. In some embodiments, the substrate is an appliance, a grill or cookware.

In some embodiments, the methods for extracting a protein, lipid, wax, fatty acid, fatty alcohol or hydrocarbon-containing substance from a substrate further comprise recovering the protein, lipid, wax, fatty acid, fatty alcohol or hydrocarbon-containing substance and optionally purifying it.

The present methods can be performed at less-than elevated temperature (e.g., at about 23° C.). However, in certain embodiments, it can be advantageous to heat a mixture of a Composition of the Invention and a substrate to improve or accelerate extraction or remediation. Thus, the present methods can be performed at a temperature of from about 5° C. to about 100° C. (e.g., about 5° C. to about 10° C., about 10° C. to about 15° C., about 15° C. to about 20° C., about 20° C. to about 25° C., about 25° C. to about 30° C., about 30° C. to about 35° C., about 35° C. to about 40° C., about 40° C. to about 45° C., about 45° C. to about 50° C., about 50° C. to about 55° C., about 55° C. to about 60° C., about 60° C. to about 65° C., about 65° C. to about 70° C., about 70° C. to about 75° C., about 75° C. to about 80° C., about 80° C. to about 85° C., about 85° C. to about 90° C., about 90° C. to about 95° C., about 95° C. to about 100° C., or any other value or range of values therein).

Contacting is conducted under conditions that are effective for extracting at least some substance from the substrate or for remediating the substrate. Thus, in certain embodiments, the contacting time is about 10 minutes, about 20 minutes, about 30 minutes, about 40 minutes, about 50 minutes, about 60 minutes, about 2 hours, about 3 hours, about 4 hours, about 5 hours, about 6 hours, about 12 hours, about 18 hours, about 24 hours, about two or three days, about a week, about a month or about several months (or any other value or range of values therein or thereabove). In addition, contacting can be conducted at a temperature of from about 5° C. to about 90° C. (e.g., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., or any other value or range of values therein). In one embodiment, the contacting occurs at an aqueous composition or a substrate temperature of about 4° C. to about 38° C. In one embodiment, the contacting is conducted at a temperature of from about 5° C. to about 50° C.; in other embodiments from about 20° C. to about 30° C. In other embodiments the contacting occurs at about 20° C., at about 30° C., at about 40° C., at about 50° C., at about 60° C., at about 70° C., at about 80° C., at about 90° C., or any other value or range of values therein or thereabove).

In certain embodiments, it can be advantageous to adjust the pH of the substrate or the aqueous compositions or extractants, for example, to effect a desired separation or to promote formation of aggregates of the substance. Thus, in certain embodiments, the pH of the substrate or the present aqueous compositions or extractants can be adjusted to about 13, about 12, about 11, about 10, about 9, about 8, about 7, about 6, about 5, about 4, about 3 (or any other value or range of values therein or therebelow). Such pH adjustment can be performed by adding an acid or base as previously described herein. The acid or base can be added continuously, or in aliquots. The acid or base can be added undiluted or as a mixture in water or organic solvent.

In certain embodiments, the present methods further comprise subjecting the aqueous composition, extractant or substrate to agitation. Thus, a substrate can be contacted with the aqueous composition or extractant, and subjected to mixing, stirring, fluid circulation, or any technique known in the art for agitating a mixture.

In some embodiments, a Composition of the Invention is combined with a hydrocarbon-containing substance, and the density of the composition is selected such that the hydrocarbon containing substance forms a layer on top of the Composition of the Invention. Thus, in some embodiments, the hydrocarbon-containing substance floats on the top of a Composition of the Invention. In some embodiments, the hydrocarbon-containing substance that floats on the top of a composition of the invention is #6 fuel oil, coal tar, or heavy oil. In some embodiments, the density difference, $\Delta\rho$, is from about 0.01 g/mL to about 10 g/mL; in some embodiments, about 0.02, about 0.03, about 0.04, about 0.05, about 0.06, about 0.07, about 0.08, about 0.09, about 0.11, about 0.12, about 0.13, about 0.14, about 0.15, about 0.16, about 0.17, about 0.18, about 0.19, about 0.20, about 0.22, about 0.24, about 0.26, about 0.28, about 0.30, about 0.32, about 0.34, about 0.36, about 0.38, about 0.40, about 0.42, about 0.44, about 0.46, about 0.48, about 0.50, about 0.55, about 0.60, about 0.65, about 0.70, about 0.75, about 0.80, about 0.85, about 0.90, about 0.95, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, about 10.0, or any other value or range of values therein.

In some embodiments, the present methods can further comprise aerating the present aqueous compositions or extractants when admixed or combined with a substrate comprising a substance such as a protein, lipid, wax, fatty acid, fatty alcohol or hydrocarbon-containing substance. Aeration can be effected by introducing a gas into a mixture comprising the present aqueous compositions or extractants and a substrate containing a substance. In some embodiments the gas is air. In other embodiments, the gas is an inert gas such as carbon dioxide, nitrogen or argon. Aeration can be conducted before stirring or agitation of the mixture, concurrent with stirring or agitation, after stirring or agitation, or any combination of before, during and after stirring or agitation. Such aeration of the present aqueous compositions or extractants can be effected by employing a suitable device for introducing a gas into a fluid, e.g., a fritted glass bubble, a gas manifold, solid or pliable tubes, etc. In some embodiments, the present methods may be performed at ambient pressure.

The extraction efficiency, i.e., amount of substance that can be extracted from a substrate, ranges from about 5 wt % of the substrate's substance to 100 wt % of the substrate's substance; in one embodiment from about 10 wt % of the substrate's substance to about 90 wt % of the substrate's substance; in other embodiments, at least about 5 wt %, at least about 10 wt %, at least about 15 wt %, at least about 20 wt %, at least about 25 wt %, at least about 30 wt %, at least about 35 wt %, at least about 40 wt %, at least about 45 wt %, at least about 50 wt %, at least about 55 wt %, at least about 60 wt %, at least about 65 wt %, at least about 70 wt %, at least about 75 wt %, at least about 80 wt %, at least about 85 wt %, at least about 90 wt %, at least about 95 wt %, at least about 96 wt %, at least about 97 wt %, at least about 98 wt %, at least about 99 wt %, about 99.5 wt %, or greater than about 99.5 wt %, (or any other value or range of values therein or thereabove) of the total amount of substance present in or on the substrate.

Accordingly, in one aspect of the present invention, the substance is a hydrocarbon-containing substance. In some embodiments, the hydrocarbon-containing substance is petrolatum, grease or oil, including heavy oil, crude oil, refined oil, shale oil, bitumen, coal tar, synthetic oil, and fractions or products thereof; automotive oil; oil from oil sand, for example, from Athabasca, Venezuela or Utah oil sand; oil obtained from hydraulic fracturing; and oil from the skin of an animal. In other embodiments, the hydrocarbon-containing substance comprises natural gas liquids.

In one embodiment, the substance is a hydrocarbon-containing substance and the substrate is a waterbody. In this regard, a hydrocarbon-containing substance can be extracted from a waterbody by treating it with a present aqueous composition or extractant. In certain embodiments, the substrate is soil. In other embodiments, the substrate is sediment. In other embodiments, the substrate is metal. In one embodiment, the substrate is a metal storage tank. In another embodiment, the substrate is a metal pipe. In another embodiment, the substrate is glass. In another embodiment, the substrate is porcelain. In another embodiment, the substrate is a concrete.

The present methods of extracting a hydrocarbon-containing substance can be performed at less-than elevated temperature (e.g., at about 23° C.). However, in certain embodiments, it can be advantageous to heat a mixture of a Composition of the Invention and a substrate to improve or accelerate extraction or remediation. Thus, the present methods can be performed at a temperature of from about 5° C. to about 100° C. (e.g., about 5° C. to about 10° C., about 10° C. to about 15° C., about 15° C. to about 20° C., about 20° C. to about 25° C., about 25° C. to about 30° C., about 30° C. to about 35° C., about 35° C. to about 40° C., about 40° C. to about 45° C., about 45° C. to about 50° C., about 50° C. to about 55° C., about 55° C. to about 60° C., about 60° C. to about 65° C., about 65° C. to about 70° C., about 70° C. to about 75° C., about 75° C. to about 80° C., about 80° C. to about 85° C., about 85° C. to about 90° C., about 90° C. to about 95° C., about 95° C. to about 100° C., or any other value or range of values therein).

The present methods are also useful for extracting hydrocarbon-containing substance (e.g., crude oil) from the skin of an animal, such as a fish, bird or mammal, for example, after an oil spill. Thus, in certain embodiments, the animal is a living animal. In other embodiments, the animal is a dead animal, which might be cleaned or decontaminated.

According to the present invention, extracting a hydrocarbon-containing substance comprises contacting the substrate with a Composition of the Invention under conditions that are effective for extracting at least some of the hydrocarbon-containing substance from the substrate. A hydrocarbon-containing substance comprises one or more hydrocarbons. In some embodiments, the hydrocarbon is aromatic, such as benzene, toluene, naphthalene, xylene and a polycyclic aromatic hydrocarbon (PAH). Illustrative PAHs include naphthalene, fluorene, phenanthrene, pyrene, chrysene, and $C_1$-$C_{10}$ homologs thereof. A $C_1$ homolog of a PAH is a PAH having a methyl group. A $C_2$ homolog of a PAH is a PAH having, for example, an ethyl group or two methyl groups. A $C_3$ homolog of a PAH is a PAH having, for example, a methyl and an ethyl group, three methyl groups, an n-propyl group or an i-propyl group. A $C_4$ homolog of a PAH is a PAH having, for example, two ethyl groups, four methyl groups, an ethyl group and two methyl groups, a methyl group and an n-propyl group, a methyl group and an i-propyl group, an n-butyl group, a sec-butyl group, and i-butyl group or a t-butyl group. In other embodiments, the hydrocarbon comprises one or more heteroatoms such as oxygen, nitrogen and sulfur. In some embodiment, the hydrocarbon is a heteroaromatic compound such as pyridine, pyrazine, quinoline, furan, or thiophene, or a polycyclic aromatic compound optionally comprising one or more heteroatoms such as N, O or S.

In other embodiments, the hydrocarbon is nonaromatic, such as a cycloalkane, cycloalkene, and straight-branched-chain alkane, alkene and alkyne. In some embodiments, the non-aromatic hydrocarbon is a linear, branched or cyclic pentane, hexane, heptane, octane, nonane, or $C_{10}$-$C_{20}$ alkane. In other embodiments, the hydrocarbon is a heteroatom-containing partially or fully saturated linear, branched, cyclic or caged compound. In some embodiments, the hydrocarbon comprises an ester, an amide, an amine, an imine, a carboxylic acid, a sulfide, a sulfoxide, a sulfone, a nitroxide or a nitrone moiety. In other embodiments, the hydrocarbon comprises a halogen. In some embodiments, the hydrocarbon-containing substance is an oil. Such oils include light oils having an API (American Petroleum Institute) gravity higher than 31.1° API (i.e., a density of less than 870 kg/m$^3$), medium oils having an API gravity between 22.3° API and 31.1° API (i.e., a density of from 870 kg/m$^3$ to 920 kg/m$^3$), heavy oils having an API gravity below 22.3° API to 10.0° API (i.e., a density of from 920 kg/m$^3$ to 1000 kg/m$^3$), or extra heavy oil having an API gravity below 10.0° API (i.e., a density of greater than 1000 kg/m$^3$). Thus, light, medium and heavy oils are less dense than water, whereas extra heavy oil is more dense than water. In some embodiments, the oil is a light tar oil. A light tar oil is an oil having an API gravity of 22.3° API to 10.0° API.

In other embodiments, the hydrocarbon-containing substance is coal tar. "Coal tar" as used herein refers to a dense non-aqueous phase liquid (DNAPL) which comprises mixture of highly aromatic hydrocarbons, where the mixture optionally comprises aliphatic hydrocarbons. Coal tar is typically a brown or black liquid having a very high viscosity, and is generally not pourable from a vessel at ambient temperatures. Coal tar is one by-product of the manufacture of coke from coal, or from gasification of coal. Coal tar can be complex or variable mixtures and can comprise one of more phenols, polycyclic aromatic hydrocarbons (PAHs), and heterocyclic compounds. "Coal tar sand" as used herein is a mixture of sand and coal tar, e.g., sand coated with coal tar, or coal tar with sand mixed or embedded therein.

In other embodiments, the hydrocarbon-containing substance is sludge, e.g., from a storage tank employed for storing industrial sewage or other waste materials. Such sludge can comprise any hydrocarbon-containing substance as described herein, including light oils, medium oils, heavy oils, extra-heavy oils, bitumen, or coal tar as described herein, in addition to sediment such as sand, silt or clay, metals or waxes. An oil-contaminated sludge is a sludge as which comprises an oil.

In certain embodiments, the oil is crude oil. In some embodiments, the crude oil is a sweet crude oil (oil having relatively low sulfur content, e.g., less than about 0.42% sulfur). In other embodiments, the crude oil is a sour crude oil (oil having relatively high sulfur content e.g., about 0.42% or more sulfur). In some embodiments, the hydrocarbon-containing substance is bitumen. Bitumen, also referred to as asphalt, typically comprises polycyclic aromatic hydrocarbons. In some embodiments, the hydrocarbon-containing substance comprises on or more petroleum distillates. In other embodiments, the hydrocarbon-containing substance is diesel fuel. In other embodiments, the hydrocarbon-containing substance is heating oil. In other embodiments, the hydrocarbon-containing substance is jet fuel. In other embodiments, the hydrocarbon-containing substance is aviation gasoline. In other embodiments, the hydrocarbon-containing substance is kerosene.

In some embodiments, the methods for extracting a hydrocarbon-containing substance from a substrate further comprise recovering the hydrocarbon-containing substance and optionally purifying it. For example, where the hydrocarbon-containing substance is crude oil, the extracted crude oil can be recovered and optionally refined to provide one or more conventional oil-derived products.

In some embodiments, the hydrocarbon-containing substance is removed from the substrate's surface. In other embodiments, hydrocarbon-containing substance is extracted from the substrate. In some embodiments the present methods for extracting the hydrocarbon-containing substance result in the formation of a biphasic or multiphasic mixture in which one of the phases is agglomerated hydrocarbon-containing substance (e.g., in the form of an "oil ball"), which can be easily removed from the aqueous composition or extractant by, for example, skimming, decantation, centrifugation or filtration. In certain embodiments, the hydrocarbon-containing substance extracted or removed from the substrate forms one or more agglomerations that can be spherical or spheroid in shape. In some embodiments, the agglomerations of hydrocarbon-containing material may range in diameter from about 0.1 mm to about 1 cm. The size of the present agglomerations can depend on the amount of hydrocarbon-containing substance present. Thus, where a large amount of hydrocarbon-containing substance is present, the agglomerations may be relatively larger in diameter, ranging from about 1 mm to about 10 cm or larger. In other embodiments, the hydrocarbon-containing substance does not agglomerate, but forms a layer on the top of the present aqueous compositions or extractants.

In still other embodiments, the hydrocarbon-containing substance can form "stringers," e.g., thread-like or filamentous masses of the hydrocarbon substance that can be extracted or removed from a substrate. For example, such stringers can have a width or diameter of from about 0.1 mm to about 1 cm or larger. The size of the present stringers can depend on the amount of hydrocarbon-containing substance present. Thus, where a large amount of hydrocarbon-containing substance is present, the stringers may be relatively larger in width or diameter, ranging from about 1 mm to about 10 cm or larger. Similarly, the stringers may have a length ranging from, e.g., about 5 mm to about 5 cm when employed in bench-scale experiments. As described with respect to width or diameter of the present stringers, that the length of the present stringers can depend on the amount of hydrocarbon-containing substance present.

In certain embodiments, the present methods further comprise subjecting the aqueous composition, extractant or substrate comprising a hydrocarbon-containing substance to agitation. Thus, a substrate can be contacted with the aqueous composition or extractant, and subjected to mixing, stirring, fluid circulation, or any technique known in the art for agitating a mixture.

In some embodiments, the present methods can further comprise aerating the present aqueous compositions or extractants when admixed or combined with a substrate comprising a hydrocarbon-containing substance. Aeration can be effected by introducing a gas into a mixture comprising the present aqueous compositions or extractants and a substrate containing a hydrocarbon-containing substance. In some embodiments the gas is air. In other embodiments, the gas is an inert gas such as carbon dioxide, nitrogen or argon. Aeration can be conducted before stirring or agitation of the mixture, concurrent with stirring or agitation, after stirring or agitation, or any combination of before, during and after stirring or agitation. Such aeration of the present aqueous compositions or extractants can be effected by employing a suitable device for introducing a gas into a fluid, e.g., a fritted glass bubble, a gas manifold, solid or pliable tubes, etc. Gas may be introduced into the mixture at a rate ranging from 0.01 L/min to about 10 L/min per liter of aqueous composition or extractant (e.g., from about 0.01 L/min to about 0.1 L/min, from about 0.1 L/min to about 0.2 L/min, from about 0.2 L/min to about 0.3 L/min, from about 0.3 L/min to about 0.4 L/min, from about 0.4 L/min to about 0.5 L/min, from about 0.5 L/min to about 0.6 L/min, from about 0.6 L/min to about 0.7 L/min, from about 0.7 L/min to about 0.8 L/min, from about 0.8 L/min to about 0.9 L/min, from about 0.9 L/min to about 1 L/min, from about 1 L/min to about 2 L/min, from about 2 L/min to about 3 L/min, from about 3 L/min to about 4 L/min, from about 4 L/min to about 5 L/min, from about 5 L/min to about 6 L/min, from about 6 L/min to about 7 L/min, from about 7 L/min to about 8 L/min, from about 8 L/min to about 9 L/min, from about 9 L/min to about 10 L/min, or any other value or range of values therein). The amount of gas introduced per liter of aqueous composition or extractant can depend on the total amount of solution present and the size of the container in which the aqueous composition or extractant is combined with the substrate containing the hydrocarbon-containing substance to be extracted. Extracted hydrocarbon-containing material in the produced froth may be separated from the froth by skimming or centrifugation. In such processes, hydrocarbon-containing material may be recovered from an extractant or aqueous composition after an extraction and frothing process, and then the extractant or aqueous composition can be recycled for reuse in an extraction process.

Aeration of the present aqueous compositions or extractants can create foam from the aqueous compositions or extractants. Such foams can have sufficient mechanical strength and/or stability to entrain or carry hydrocarbon-containing substance which has been removed or extracted from a substrate. Thus, aeration may provide a foam which entrains and transports an extracted hydrocarbon-containing substance out of the vessel in which such a substrate was combined with the present aqueous compositions or extractants.

In some embodiments, the present methods for extracting a hydrocarbon-containing substance from a substrate comprise hydraulically fracturing the substrate with a fracturing fluid that comprises a present aqueous composition or extractant. The method can comprise injecting a fracturing fluid comprising a present composition or extractant into a substrate (e.g., a rock formation) at a pressure effective to fracture the substrate. Surface pumping pressures can range from about 500 psi (pounds-per-square-inch, lb/in$^2$) to about 15,000 psi (e.g., about 500 psi, about 1,000 psi, about 1,500 psi, about 2,000 psi, about 2,500 psi, about 3,000 psi, about 3,500 psi, about 4,000 psi, about 4,500 psi, about 5,000 psi, about 5,500 psi, about 6,000 psi, about 6,500 psi, about 7,000 psi, about 7,500 psi, about 8,000 psi, about 8,500 psi, about 9,000 psi, about 9,500 psi, about 10,000 psi, about 10,500 psi, about 11,000 psi, about 11,500 psi, about 12,000 psi, about 12,500 psi, about 13,000 psi, about 13,500 psi, about 14,000 psi, about 14,500 psi, about 15,000 psi). The surface pumping pressure can vary depending on fluid injection rates, well depth and orientation (e.g., vertical, horizontal, inclined, etc.), formation type (e.g., sandstone, limestone, etc.), perforation size and number of perforations in the production casing across the production zone being fractured, etc. Furthermore, fluid pumping pressures typically vary over the course of the fracturing operation, and can increase, decrease, or both during the course of a fracturing operation.

The fracturing fluid can further comprise one or more additives such as a proppant, viscosity modifier, radioactive tracer, gel, alcohol, detergent, acid, fluid-loss additive, gas (e.g., nitrogen or carbon dioxide) dispersant or flocculant. The fracturing fluid can then be recovered or produced from the substrate (e.g., via a wellbore), extracting the hydrocarbon-containing substance from the substrate as the fracturing fluid is recovered or produced. The resultant mixture of the fracturing fluid and extracted hydrocarbon-containing substance can be further processed to separate the hydrocarbon-containing substance from the fracturing fluid.

Accordingly, in certain embodiments, the present invention provides a hydraulic fracturing fluid comprising an aqueous composition of the present invention. In certain embodiments, the hydraulic fracturing fluid further comprises an additive. In some embodiments, the additive is one or more of a proppant, a viscosity modifier, a radioactive tracer, a gel, an alcohol, a detergent, an acid, a fluid loss additive, a gas, a dispersant or a flocculant. In other embodiments, the present invention provides a hydraulic fracturing fluid comprising an extractant of the present invention. In certain embodiments, the hydraulic fracturing fluid further comprises an additive. In certain embodiments, the additive is one or more of a proppant, a viscosity modifier, a radioactive tracer, a gel, an alcohol, a detergent, an acid, a fluid loss additive, a gas, a dispersant or a flocculant. In certain embodiments, the invention further provides a method for extracting a hydrocarbon-containing substance from a substrate, comprising hydraulically fracturing the substrate with a hydraulic fracturing fluid comprising an aqueous composition of the present invention. In other embodiments, the present invention provides a method for extracting a hydrocarbon-containing substance from a substrate, comprising hydraulically fracturing the substrate with a hydraulic fracturing fluid comprising an extractant of the present invention.

The extraction efficiency, i.e., amount of hydrocarbon-containing substance that can be extracted from a substrate, ranges from about 5 wt % of the substrate's hydrocarbon-containing substance to 100 wt % of the substrate's hydrocarbon-containing substance; in one embodiment from about 10 wt % of the substrate's hydrocarbon-containing substance to about 90 wt % of the substrate's hydrocarbon-containing substance; in other embodiments, at least about 5 wt %, at least about 10 wt %, at least about 15 wt %, at least about 20 wt %, at least about 25 wt %, at least about 30 wt %, at least about 35 wt %, at least about 40 wt %, at least about 45 wt %, at least about 50 wt %, at least about 55 wt %, at least about 60 wt %, at least about 65 wt %, at least about 70 wt %, at least about 75 wt %, at least about 80 wt %, at least about 85 wt %, at least about 90 wt %, at least about 95 wt %, at least about 96 wt %, at least about 97 wt %, at least about 98 wt %, at least about 99 wt %, about 99.5 wt %, or greater than about 99.5 wt %, (or any other value or range of values therein or thereabove) of the total amount of hydrocarbon-containing substance present in or on the substrate.

In some embodiments, the present methods may be performed at ambient pressure. In other embodiments, the present methods may be conducted at a reduced pressure from about 100 mm Hg to about 760 mm Hg (e.g., from about 100 mm Hg to about 200 mm Hg, from about 200 mm Hg to about 300 mm Hg, from about 300 mm Hg to about 400 mm Hg, from about 400 mm Hg to about 500 mm Hg, from about 500 mm Hg to about 600 mm Hg, from about 600 mm Hg to about 700 mm Hg, from about 700 mm Hg to about 760 mm Hg, or any other value or range of values therein). In other embodiments, the present methods may be performed at an elevated pressure from about 760 mm Hg to about 7600 mm Hg (e.g., from about 760 mm Hg to about 1520 mm Hg, from about 1520 mm Hg to about 2280 mm Hg, from about 2280 mm Hg to about 3040 mm Hg, from about 3040 mm Hg to about 3800 mm Hg, from about 3800 mm Hg to about 4560 mm Hg, from about 4560 mm Hg to about 5320 mm Hg, from about 5320 mm Hg to about 6080 mm Hg, from about 6080 mm Hg to about 6840 mm Hg, from about 6840 mm Hg to about 7600 mm Hg, or any other value or range of values therein).

The present invention further provides methods for remediating a substrate by removing a hydrocarbon-containing substance comprising contacting the substrate with a Composition of the Invention of the invention under conditions effective for remediating the substrate. Remediating can include purifying water by removing a hydrocarbon-containing substance such that it becomes potable, suitable for swimming or non-toxic to aquatic species; converting soil contaminated with a hydrocarbon-containing substance to that which is useful as farmland or for real estate; converting hydrocarbon-containing oil sand to sand that is suitable for commercial or recreational use, etc. Thus, remediating a substrate can substantially improve the quality of a substrate, for example, rendering it non-toxic. In some embodiments, remediating the substrate includes removing a hydrocarbon-containing substance from the surface of a substrate, or extracting the hydrocarbon-containing substance from pores, fractures, cracks, fissures or crevices in a substrate. The present methods are useful for remediating environmentally contaminated sites, soils or animals.

Accordingly, in certain embodiments, the present invention provides methods for remediating a substrate, comprising contacting the substrate with an aqueous composition of the present invention under conditions effective for remediating the substrate. In some embodiments, the substrate is plastic, rock, mineral, bone, teeth, soil, sand, wood, paper, skin, a waterbody, gravel, mud, clay, plant, hair, fabric, glass, porcelain, concrete, metal or an animal. In certain embodiments, the substrate is a waterbody. In other embodiments, the substrate is soil. In some embodiments, the substrate is an animal. In some embodiments, the animal is a living animal. In other embodiments, the animal is a dead animal. In certain embodiments, remediating comprises extracting a hydrocarbon-containing substance from the substrate. In other embodiments, the contacting occurs at an aqueous composition or a substrate temperature of about 5° C. to about 90° C. (e.g., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., or any other value or range of values therein). In one embodiment, the contacting occurs at an aqueous composition or a substrate temperature of about 4° C. to about 38° C. In some embodiments, the method further comprises subjecting the aqueous composition or substrate to agitation. In some embodiments, the agitation is mixing. In some embodiments, the hydrocarbon-containing substance is petrolatum, grease, oil, coal tar, bitumen, coal tar sand, sludge, oil-contaminated sludge, light tar oil or creosote. In certain embodiments, the oil is automotive oil. In other embodiments, the automotive oil is synthetic automotive oil. In some embodiments, the oil is crude oil. In some embodiments, the hydrocarbon-containing substance comprises one or more petroleum distillates. In other embodiments, the hydrocarbon-containing substance is diesel fuel. In other embodiments, the hydrocarbon-containing substance is heating oil. In other embodiments, the hydrocarbon-containing substance is jet fuel. In other embodiments, the hydrocarbon-containing substance is aviation gasoline. In other embodiments, the hydrocarbon-containing substance is kerosene.

In another aspect, the present invention provides a method for remediating a substrate, comprising contacting the substrate with an extractant of the present invention under conditions effective for remediating the substrate. In certain embodiments, the substrate is soil, sand, wood, paper, skin, a waterbody, gravel, mud, clay, plant, hair, fabric, metal or an animal. In other embodiments, the substrate is a waterbody. In some embodiments, the substrate is soil. In other embodiments, the substrate is an animal. In some embodiments, the animal is a living animal. In other embodiments, the animal is a dead animal. In some embodiments, remediating comprises extracting a hydrocarbon-containing substance from the substrate. In certain embodiments, contacting occurs at an extractant or substrate temperature of about 5° to about 90° C. (e.g., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., or any other value or range of values therein). In one embodiment, the contacting occurs at an aqueous composition or a substrate temperature of about 4° C. to about 38° C. In other embodiments, the method further comprises subjecting the extractant or substrate to agitation. In some embodiments, the agitation is mixing. In certain embodiments, agitation comprises sonication. In other embodiments, agitation is effected by microwave. In other embodiments, the hydrocarbon-containing substance is grease, oil, coal tar, bitumen, coal tar sand, sludge, oil-contaminated sludge, light tar oil or creosote. In some embodiments, the oil is automotive oil. In other embodiments, the automotive oil is synthetic automotive oil. In certain embodiments, the oil is crude oil. In some embodiments, the hydrocarbon-containing substance comprises one or more petroleum distillates. In other embodiments, the hydrocarbon-containing substance is diesel fuel. In other embodiments, the hydrocarbon-containing substance is heating oil. In other embodiments, the hydrocarbon-containing substance is jet fuel. In other embodiments, the hydrocarbon-containing substance is aviation gasoline. In other embodiments, the hydrocarbon-containing substance is kerosene.

In another aspect, the present methods result in the sequestration of hydrocarbon-containing substance present in or on the substrate. Such methods can comprise introducing a present aqueous composition or extractant into the soil, e.g., the soil's subsurface, via, e.g., groundwater monitoring or one or more remediation wells. Without being bound by any particular theory of the mechanism of such sequestration, introducing a present aqueous composition or extractant into the soil can effectively encapsulate or agglomerate hydrocarbon-containing substance therein, rendering it relatively immobile. Accordingly, such methods can also render the hydrocarbon-containing substance effectively inert via sequestration.

The present methods can be performed by allowing the substrates and present aqueous compositions or extractants to contact within a container, such as a tank, vessel, pool or pit. The contacting can be performed at atmospheric pressure or above in a batch, semi-batch or continuous mode, for example, where hydrocarbon-containing substance is continuously removed from the substrate. In some embodiments, the present aqueous compositions or extractants are reused after removing hydrocarbon-containing substance from a substrate or after remediating a substrate. In other embodiments, "fresh," previously unused aqueous composition or extractant is continuously contacted with the substrate.

Contacting is conducted under conditions that are effective for extracting at least some hydrocarbon-containing substance from the substrate or for remediating the substrate. Thus, in certain embodiments, the contacting time is about 10 minutes, about 20 minutes, about 30 minutes, about 40 minutes, about 50 minutes, about 60 minutes, about 2 hours, about 3 hours, about 4 hours, about 5 hours, about 6 hours, about 12 hours, about 18 hours, about 24 hours, about two or three days, about a week, about a month or about several months (or any other value or range of values therein or thereabove). In addition, contacting can be conducted at a temperature of from about 5° C. to about 90° C. (e.g., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., or any other value or range of values therein). In one embodiment, the contacting occurs at an aqueous composition or a substrate temperature of about 4° C. to about 38° C. In one embodiment, the contacting is conducted at a temperature of from about 5° C. to about 50° C.; in other embodiments from about 20° C. to about 30° C. In other embodiments the contacting occurs at about 20° C., at about 30° C., at about 40° C., at about 50° C., at about 60° C., at about 70° C., at about 80° C., at about 90° C., or any other value or range of values therein or thereabove).

In certain embodiments, it can be advantageous to adjust the pH of the substrate or the aqueous compositions or extractants, for example, to effect a desired separation or to promote formation of aggregates of hydrocarbon-containing substance. Thus, in certain embodiments, the pH of the substrate or the present aqueous compositions or extractants can be adjusted to about 13, about 12, about 11, about 10, about 9, about 8, about 7, about 6, about 5, about 4, about 3 (or any other value or range of values therein or therebelow). Such pH adjustment can be performed by adding an acid or base as previously described herein. The acid or base can be added continuously, or in aliquots. The acid or base can be added undiluted or as a mixture in water or organic solvent.

Industrial extraction of oil from the Athabasca oil sands produces wastewater comprising fines, or small particulates, in the oil extraction process. These fines can remain suspended in waste water and prevent recycling of water in an extraction process, or alternatively, prevent discharge of fines-laden wastewater into the environment. Accordingly, a method to promote rapid settling of fines, thereby allowing discharge of the wastewater from an extraction process, is desirable. Thus, in one embodiment, the present invention provides a method for precipitating fines contained in a vessel further containing a hydrocarbon-containing material and a aqueous composition or an extractant as described herein, comprising acidifying the contents of said vessel to a pH of about 4.6 or less.

Any Composition of the Invention as described herein may be employed in an extraction process which produces fines-laden water. The resultant fines-laden water, which can further comprise hydrocarbon-containing material, can then be acidified to reduce the pH of the fines-laden water to less than about 4.6, and precipitate the fines suspended therein. Acids which may be suitable for reducing the pH of the fines-laden water may include organic or inorganic acids. For example, the inorganic acids may include hydrofluoric acid, hydrochloric acid, hydrobromic acid, hydroiodic acid, sulfurous acid, sulfuric acid, phosphoric acid, nitric acid and carbonic acid. Organic acids can alternatively be employed. Suitable organic acids include $C_1$ to $C_{20}$ organic acids such as formic acid, citric acid, malic acid, adipic acid, tannic acid, lactic acid, ascorbic acid, acetic acid, fumaric acid, and mixtures thereof.

The acid can be added in concentrated form, or as an aqueous solution. The acid is generally added to the solution in which the fines are present, and can be added with concomitant agitation. Alternatively, the solution may be agitated after addition of the acid. Such agitation may include mechanical agitation, or hydraulic mixing provided by pumping and circulation of the fines-laden fluid in the vessel in which it is contained.

The vessel may be a metal or polymer tank, or may be an earthen pit or excavated reservoir, which may be lined to prevent fluid communication of the wastewater with groundwater and/or subterranean water-nearing formations. After addition of the acid, and mixing to disperse the acid in solution, the solution is typically allowed to stand for a period of time to allow the fines to settle, and for any hydrocarbon-containing material released from the fines or present in the solution to float to the surface. Settling times may range from about 1 minute to about 1 week (e.g., from about 1 minute to about 2 minutes, from about 2 minutes to about 5 minutes, from about 5 minutes to about 10 minutes, from about 10 minutes to about 20 minutes, from about 20 minutes to about 30 minutes, from about 30 minutes to about 40 minutes, from about 40 minutes to about 50 minutes, from about 50 minutes to about 1 hour, from about 1 hour to about 2 hours, from about 2 hours to about 3 hours, from about 3 hours to about 4 hours, from about 4 hours to about 5 hours, from about 5 hours to about 6 hours, from about 6 hours to about 7 hours, from about 7 hours to about 8 hours, from about 8 hours to about 9 hours, from about 9 hours to about 10 hours, from about 10 hours to about 11 hours, from about 11 hours to about 12 hours, from about 12 hours to about 1 day, from about 1 day to about 2 days, from about 2 days to about 3 days, from about 3 days to about 4 days, from about 4 days to about 5 days, from about 5 days to about 6 days, from about 6 days to about 1 week, or any other value or range of values therein). Residual hydrocarbon-containing material released during or after acidification and/or settling can be recovered by, e.g., skimming. In other embodiments, remaining hydrocarbon-containing material may be separated by centrifugation. In such processes, hydrocarbon-containing material may be recovered from an extractant or aqueous composition after an extraction process; fines can be removed by lowering the pH; and then remaining hydrocarbon-containing material can be removed by centrifugation. The remaining extractant or aqueous composition can then be recycled for reuse in an extraction process.

In other embodiments, the aqueous compositions or extractants further comprise a substrate, which can be present in the aqueous composition or extractant in a weight ratio of substrate:aqueous composition or extractant from about 0.01:1 to about 1:1, in one embodiment, from about 0.1:1 to about 1:1. However, the substrate:aqueous composition or extractant ratio is not limited, and can be selected according to a particular application and to minimize the amount of the aqueous composition or extractant employed.

Thus, in certain embodiments, the present invention provides a method for extracting a hydrocarbon-containing substance from a substrate, comprising contacting the substrate with a Composition of the Invention under conditions effective for extracting at least some of the hydrocarbon-containing substance from the substrate. In other embodiments, the substrate is soil, sand, wood, rock, paper, skin, a waterbody, gravel, mud, clay, plant, hair, fabric, metal, glass, porcelain, concrete or an animal. In some embodiments, the substrate is a waterbody. In other embodiments, the substrate is soil. In other embodiments, the substrate is an animal. In some embodiments, the animal is a living animal. In one embodiment, the animal is a dead animal. In other embodiments, the extracting comprises removing the hydrocarbon-containing substance from the surface of the substrate. In some embodiments, the contacting occurs at an aqueous composition or a substrate temperature of about 5° to about 50° C. In other embodiments, the method further comprises subjecting the aqueous composition or the substrate to agitation.

In one embodiment, the agitation is mixing. In certain embodiments, agitation comprises sonication. In other embodiments, agitation is effected by microwave. In some embodiments, the hydrocarbon-containing substance is grease, oil, coal tar, bitumen, coal tar sand, sludge, oil-contaminated sludge, light tar oil or creosote. In other embodiments, the oil is automotive oil. In other embodiments, automotive oil is synthetic automotive oil. In certain embodiments, the oil is crude oil. In some embodiments, the hydrocarbon-containing substance comprises one or more petroleum distillates. In other embodiments, the hydrocarbon-containing substance is diesel fuel. In other embodiments, the hydrocarbon-containing substance is heating oil. In other embodiments, the hydrocarbon-containing substance is jet fuel. In other embodiments, the hydrocarbon-containing substance is aviation gasoline. In other embodiments, the hydrocarbon-containing substance is kerosene.

In another aspect, the present invention provides a method for extracting a hydrocarbon-containing substance from a substrate, comprising contacting the substrate with a Composition of the Invention under conditions effective for extracting at least some of the hydrocarbon-containing substance from the substrate. In certain embodiments, the substrate is plastic, mineral, bone, teeth, soil, sand, wood, rock, paper, skin, a waterbody, gravel, mud, clay, plant, hair, fabric, metal or an animal. In other embodiments, the substrate is a waterbody. In some embodiments, the substrate is soil. In other embodiments, the substrate is an animal. In some embodiments, the animal is a living animal. In one embodiment, the animal is a dead animal. In certain embodiments, extracting comprises removing the hydrocarbon-containing substance from the surface of the substrate. In some embodiments, contacting occurs at an extractant or a substrate temperature of about 5° to about 90° C. In some embodiments, the method further comprises subjecting the extractant or the substrate to agitation. In certain embodiments, the agitation is mixing. In some embodiments, the hydrocarbon-containing substance is grease, oil, coal tar, bitumen, coal tar sand, sludge, oil-contaminated sludge, light tar oil or creosote. In other embodiments, the oil is automotive oil. In some embodiments, the automotive oil is synthetic automotive oil. In some embodiments, the oil is crude oil.

In another aspect the present invention provides a method for extracting a hydrocarbon-containing substance from a substrate, comprising contacting the substrate with a Composition of the Invention under conditions effective for extracting at least some of the hydrocarbon-containing substance from the substrate. In some embodiments, extracting comprises removing a hydrocarbon-containing substance from the surface of the substrate. In other embodiments, the present methods for extracting hydrocarbon-containing substance from a substrate, comprising contacting the substrate with an extractant of the present invention under conditions effective for extracting at least some of the hydrocarbon-containing substance from the substrate. In certain embodiments, extracting comprises removing a hydrocarbon-containing substance from the surface of the substrate. In another embodiment, the present methods for remediating a substrate comprise contacting a substrate with an aqueous composition of the present invention under conditions effective for remediating the substrate. In some embodiments, remediating the substrate comprises sequestering one or more contaminants in the substrate. In other embodiments, the present methods for remediating a substrate comprise contacting the substrate with an extractant of the present invention under conditions effective for remediating the substrate. In some embodiments, remediating the substrate comprises sequestering one or more contaminants in the substrate.

As described herein, another aspect of the present invention is a method for extracting a substance from a substrate comprises contacting the substrate with a Composition of the Invention under conditions effective for extracting at least some of the substance from the substrate, wherein the substance comprises a protein, lipid, wax, fatty acid or fatty alcohol. In one embodiment, the substance is a protein, lipid, wax, fatty acid or fatty alcohol, and the substrate is plastic, rock, mineral, bone, teeth, soil, sand, wood, paper, skin, a waterbody, gravel, mud, clay, plant, hair, fabric, metal, glass, ceramic, porcelain, a living animal or a dead animal. In some embodiments, the substance is tar, tar sand, coal tar, or asphalt, and the substrate is plastic, rock, mineral, bone, teeth, soil, sand, wood, paper, skin, a waterbody, gravel, mud, clay, plant, hair, fabric, metal, glass, ceramic, porcelain, a living animal or a dead animal. In other embodiments, the substance is grease, and the substrate is plastic, rock, mineral, bone, teeth, soil, sand, wood, paper, skin, a waterbody, gravel, mud, clay, plant, hair, fabric, metal, glass, ceramic, porcelain, a living animal or a dead animal.

In another embodiment, a method for remediating a substrate from a substance comprises contacting the substrate with a Composition of the Invention under conditions effective for remediating the substrate from the substance, wherein the substance comprises a protein, lipid, wax, fatty acid or fatty alcohol, and wherein the substrate is plastic, rock, mineral, bone, teeth, soil, sand, wood, paper, skin, a waterbody, gravel, mud, clay, plant, hair, fabric, metal, glass, ceramic, porcelain, a living animal or a dead animal. In other embodiments, the substance is a protein, lipid, wax, fatty acid or fatty alcohol, and the substrate is plastic, rock, mineral, bone, teeth, soil, sand, wood, paper, skin, a waterbody, gravel, mud, clay, plant, hair, fabric, metal, glass, ceramic, porcelain, a living animal or a dead animal. In some embodiments, the substance is tar, tar sand, coal tar, or asphalt, and the substrate is plastic, rock, mineral, bone, teeth, soil, sand, wood, paper, skin, a waterbody, gravel, mud, clay, plant, hair, fabric, metal, glass, ceramic, porcelain, a living animal or a dead animal. In other embodiments, the substance is grease, and the substrate is plastic, rock, mineral, bone, teeth, soil, sand, wood, paper, skin, a waterbody, gravel, mud, clay, plant, hair, fabric, metal, glass, ceramic, porcelain, a living animal or a dead animal.

In one embodiment, the substance comprises a protein. The protein can comprise one or more amino acids. In some embodiments, the substance is a bodily fluid or plant extract.

In another embodiment, the substance comprises a lipid. The lipid can be a fat, for example a plant or animal fat; wax; sterol, for example chlolesterol; fat-soluble vitamin; glyceride; or phospholipid. In one embodiment, the glyceride is a monoglyceride, diglyceride, or triglyceride. The glyceride can be saturated or unsaturated. The wax can be an animal wax or plant wax. In some embodiments, the wax is a petroleum derived wax. The sterol can be a naturally occurring sterol, such as from a plant, animal or fungi. In another embodiment, the sterol is synthetic. The vitamin can be a vitamin A, D, E or K. In some embodiments, the substance is a fatty acid. The fatty acid can be saturated or unsaturated. In some embodiments, the lipid is a high-density lipid (HDL) or low-density lipid (LDL).

In some embodiments, the substance is from a plant source, such as a triglyceride from a plant source. In some embodiments, the substance is a fat, oil or grease from a plant source. The substance can be hydrogenated oil, such as hydrogenated oil from a plant source. The plant source can be a vegetable, fruit, nut, or seed. The plant source can be an olive, palm, soybean, rapeseed, sunflower, peanut, cotton, coconut, corn, grape, hazelnut, flax, rice, safflower, or sesame. In some embodiments, the substance is olive oil, palm oil, soybean oil, rapeseed oil, sunflower oil, peanut oil, cotton oil, coconut oil, corn oil, grape oil, hazelnut oil, flax oil, rice oil, safflower oil, or sesame oil.

In other embodiments, the substance is from an animal source, such as a triglyceride from an animal source. In some embodiments, the substance is a fat, oil or grease from an animal source. In some embodiments, the substance is an animal fat, oil or grease. The substance can be hydrogenated oil, such as hydrogenated oil from an animal source. The animal can be a fish, bird, or mammal.

In one embodiment, the substance is sebum. The Compositions of the Invention (optionally comprising a cosmetically acceptable vehicle) are useful for extracting or removing sebum. In one embodiment, an effective amount of a Composition of the Invention (optionally comprising a cosmetically acceptable vehicle) is applied to the skin of a subject in need thereof for controlling or preventing the appearance or perception of excessive sebum secretion.

The Compositions of the Invention (optionally comprising a cosmetically acceptable vehicle) are useful for providing a skin benefit. In one embodiment, a method for providing a skin benefit comprises applying to the skin of a subject in need thereof an effective amount of a Composition of the Invention (optionally comprising a cosmetically acceptable vehicle). The skin can be the skin on the face, neck, chest, back, arms, hands, legs or scalp of a subject.

In some embodiments, providing a skin benefit comprises protecting or improving the state of the skin, or preventing or treating imperfections of the skin, of a subject in need thereof. In other embodiments, providing a skin benefit comprises improving the appearance of oily skin, inhibiting sebum secretion, or inhibiting microbial activity. In other embodiments, providing a skin benefit comprises treating or preventing a wound, acne, psoriasis, atopic skin, diabetic skin, dermatitis, eczema, xerotic skin, dry skin, or chaffed skin. In yet other embodiments, providing a skin benefit comprises increased elasticity, increased firmness, decreased sagginess, decreased dryness, decreased flakiness, decreased fine lines or wrinkles, decreased pits or nodules, decreased damage caused by ultraviolet radiation, decreased age spots, or increased evenness in skin tone.

In some embodiments, an effective amount of a Composition of the Invention (optionally comprising a cosmetically acceptable vehicle) is used for treating rings under the eye, symptoms of aging, protecting the skin, increasing the detoxification of xenobiotics, intervening on pigmentation level, inhibiting melanogenesis, protecting the body against pollution, stimulating the detoxification systems, modulating DHT levels, intervening on adipocytes, or promoting lipolysis.

A quantity of a Composition of the Invention, for example from 1 to 100 mL, can be applied to the skin, from a suitable container or applicator and, if necessary, it is then spread over and/or rubbed into the skin using the hand or fingers or a suitable device.

In some embodiments, a Composition of the Invention (optionally comprising a cosmetically acceptable vehicle) is useful for controlling, preventing, or treating oily or greasy hair, or stimulating hair or body hair growth. The Composition of the Invention (optionally comprising a cosmetically acceptable vehicle) can be applied to the scalp can be a shampoo or conditioner, such as those described herein. Thus, another aspect of the present invention is a method for controlling, preventing, or treating oily or greasy hair comprising applying to the scalp or hair of a subject in need thereof an effective amount of a Composition of the Invention (optionally comprising a cosmetically acceptable vehicle). Another aspect of the present invention is a method for promoting hair growth comprising applying to the scalp of a subject in need thereof an effective amount of a Composition of the Invention (optionally comprising a cosmetically acceptable vehicle).

The subject may be suffering from a type of hair loss, such as alopecia. The subject may have considerable, temporary or permanent hair loss. The hair loss may be induced by poor nutrition, emotional stress, hormone imbalance, or medicinal drugs, such as cancer chemotherapy agents.

In some embodiments, the method for stimulating or promoting hair growth further comprises administering to the subject an additional agent. The administration of the additional agent can be topical or oral. The administration of the additional agent can be sequential or concurrent with a Composition of the Invention (optionally comprising a cosmetically acceptable vehicle). Thus, the additional agent can be administered prior to, concurrent with, or subsequent to, administration or application of Composition of the Invention (optionally comprising a cosmetically acceptable vehicle). In some embodiments, the additional agent is in a composition with a Composition of the Invention (optionally comprising a cosmetically acceptable vehicle).

The additional agent can be minoxidil, procaine hydrochloride, niacin, pyrimidine 3-oxide compounds, or mixtures thereof. In one embodiment, the additional agent is hydrogen peroxide. The hydrogen peroxide can be administered in an amount effective to cleanse at least a portion of the skin. The cleansing can be removal of dirt, debris, air pollutants, desquamating cells, or cutaneous secretions of the skin. In one embodiment, the hydrogen peroxide is topically administered as a 3% solution (by mass) to cleanse the skin before topically administering a Composition of the Invention (optionally comprising a cosmetically acceptable vehicle).

In another embodiment, the additional agent is a moisturizing agent, such as described herein. In yet another embodiment, the additional agent is an exfoliant. Administering an exfoliant may help remove dead or dying skin cells and further improve the skin's ability to absorb a Composition of the Invention (optionally comprising a cosmetically acceptable vehicle).

Application of a Composition of the Invention (optionally comprising a cosmetically acceptable vehicle) to the scalp may be from 1 time to 3 times every 24 hours, every week, or every month.

The Compositions of the Invention (optionally comprising a cosmetically acceptable vehicle) are useful for treating or preventing an oral condition or disease. In one embodiment, a method for treating or preventing a periodontal disease, dental plaque or dental decay comprises administering to the oral cavity of a subject in need thereof an effective amount of a Composition of the Invention (optionally comprising a cosmetically acceptable vehicle). The periodontal disease can be gingivitis or periodontitis. The Composition of the Invention (optionally comprising a cosmetically acceptable vehicle) can be formulated as a toothpaste or mouthwash. In one embodiment, the Composition of the Invention (optionally comprising a cosmetically acceptable vehicle) further comprises fluoride or zinc ions.

The Compositions of the Invention are useful for healing wounds. In one embodiment, a method for accelerating wound healing comprises contacting a wound of a subject with a Composition of the Invention (optionally comprising a cosmetically acceptable vehicle) under conditions effective for accelerating wound healing. The Composition of the Invention (optionally comprising a cosmetically acceptable vehicle), may be contained in an article, such as described herein. In some embodiments, the article is a bandage, absorptive dental roll, napkin, diaper, pad, wiping cloth, tissue wipe, premoistened towelette, undersheet, surgical dressing, toilet paper or facial tissue.

The Compositions of the Invention are useful for purifying a mixture comprising an alcohol and an impurity. In one embodiment, a method for purifying a mixture comprising an alcohol and an impurity comprises contacting the mixture with a Composition of the Invention under conditions effective for removing at least some of the impurity from the mixture. In some embodiments, the impurity comprises an aldehyde, ketone, fusel oil, or inorganic salt. In some embodiments, the alcohol is methyl, ethyl, isopropyl, n-propyl, isobutyl, sec-butyl, tert-butyl or n-butyl alcohol. The mixture can be an alcoholic beverage, such as a beer, wine or alcoholic liquor. In one embodiment, the alcoholic liquor is distilled. The alcoholic liquor can be scotch, whiskey or rum. In some embodiments, purification of a mixture results in an alcoholic beverage with a different flavor, odor or color as compared to the mixture prior to purification.

The substantially anhydrous Compositions of the Invention are useful as an agent that inhibits the agglomeration of a granulated product. In some embodiments, the Composition of the Invention is an anti-caking agent. Also provided herein are methods for inhibiting the agglomeration of a granulated product comprising, contacting the granulated product with a substantially anhydrous Composition of the Invention under conditions effective for inhibiting agglomeration of the granulated product.

A granulated product is a conglomeration of discrete solid, particles, in which the particles flow freely when dry, and the particles agglomerate or clump when wet. The Composition of the Invention can improve the resistance to humidity and improve the flowability of the granulated product. The granulated product can comprise particles that are less than 5 mm in size. In some embodiments, the granulated product comprises particles that are less than 1, 2, 3, 4, or 5 mm in size. In some embodiments, the particles are less than 1, 5, 10, 100, 250 or 500 µm in size. In some embodiments, the granulated product is a powder.

The granulated product can be a food or beverage product. The food product can be salt, sugar, dry milk powder, flour, egg mix, pancake mix, cocoa, coffee powder, sugar substitute, powdered drink mix. In some embodiments, the granulated product is not a food product, such as road salt, fertilizer, powdered cosmetic or powdered detergent.

The Compositions of the Invention are useful as a plant fertilizer. In one embodiment, the fertilizer comprises sand and a Composition of the Invention. In another embodiment, the fertilizer comprises soil and a Composition of the Invention. In some embodiments, the fertilizer comprises a Composition of the Invention and one or more water-soluble mineral nutrients, such nitrogen, phosphorous, potassium, calcium, ionic magnesium, iron, manganese, zinc, copper, boron or molybdenum. In some embodiments, the fertilizer comprises a Composition of the Invention and compost. In other embodiments, the fertilizer comprises a Composition of the Invention and starch, fulvic acid, digested plant material, digested lignin, soluble seaweed, cane sugar, malt, beet vinasse, molasses, water-soluble hydrocolloid polysaccharides, compost tea extracts, vermicompost, cellulose, chitosan, or mixtures thereof. In other embodiments, the fertilizer may comprise a Composition of the Invention and a mineral salt. The mineral salt can be ammonium nitrate; ammonium phosphate; ammonium sulphate; calcium nitrate; calcium phosphate; calcium sulphate; magnesium nitrate; magnesium phosphate; magnesium sulphate; potassium nitrate; potassium phosphate; potassium sulphate; iron sulphate; iron phosphate; iron glycinate; iron lignosulphate; chelated iron such as iron chelated via ethylene-diamine-tetra-acetic acid (EDTA) or iron chelated via diethylenetri-amine pentaacetic acid (DTPA); and urea.

In some embodiments, the present invention also provides a fertilizer. The fertilizer comprises from about 5 wt % to about 50 wt % of a plant material as described herein. In some embodiments, the plant material comprises a protein. In some embodiments, the fertilizer comprises about 5 wt %, about 10 wt %, about 15 wt %, about 20 wt %, about 25 wt %, about 30 wt %, about 35 wt %, about 40 wt %, about 45 wt %, about 50 wt % of the plant material. In some embodiments, the plant material is hemp seed.

The fertilizer can comprise a base in an amount of from about 3 wt % to about 20 wt %, e.g., about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %. Bases which are useful are those described herein which are useful in the aqueous solutions, extractants and substantially anhydrous compositions.

The fertilizer can also comprise a sugar, a polysaccharide or molasses in an amount of from about 0.1 wt % to about 5 wt %, e.g., about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 2 wt %, about 3 wt %, about 4 wt %, about 5 wt %. Sugars and polysaccharides which are useful in the present fertilizer include those which are useful in the aqueous solutions, extractants and substantially anhydrous compositions as described herein.

The fertilizer can comprise from about 0.05 wt % to about 20 wt % of an additive, e.g., about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %. Additives useful in the present fertilizer include those which are useful in the aqueous solutions, extractants and substantially anhydrous compositions as described herein. Suitable additives also include dolomitic lime, calcium carbonate and magnesium carbonate.

The fertilizer can comprise from about 0 wt % to about 25 wt % of guar gum, e.g., about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt %, about 25 wt %.

The fertilizer can comprise from about 5 wt % to about 25 wt % of a nitrogen source such as urea, e.g., about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt %, about 25 wt %. Other suitable nitrogen sources can include nitrogen-containing organic compounds and inorganic nitrogen-containing salts.

The fertilizer can comprise from about 0.01 wt % to about 1 wt % of an iron-containing compound, e.g., about 0.01 wt %, about 0.05 wt %, about 0.1 wt %, about 0.15 wt %, about 0.2 wt %, about 0.25 wt %, about 0.3 wt %, about 0.35 wt %, about 0.4 wt %, about 0.45 wt %, about 0.5 wt %, about 0.55 wt %, about 0.6 wt %, about 0.65 wt %, about 0.7 wt %, about 0.75 wt %, about 0.8 wt %, about 0.85 wt %, about 0.9 wt %, about 0.95 wt %, about 1.0 wt %. Iron compounds which are useful in the present fertilizer include yellow iron, black iron, red iron, orange iron and brown iron.

The fertilizer can also comprise from about 30 wt % to about 60 wt % water, e.g., about 30 wt %, about 31 wt %, about 32 wt %, about 33 wt %, about 34 wt %, about 35 wt %, about 36 wt %, about 37 wt %, about 38 wt %, about 39 wt %, about 40 wt %, about 41 wt %, about 42 wt %, about 43 wt %, about 44 wt %, about 45 wt %, about 46 wt %, about 47 wt %, about 48 wt %, about 49 wt %, about 50 wt %, about 51 wt %, about 52 wt %, about 53 wt %, about 54 wt %, about 55 wt %, about 56 wt %, about 57 wt %, about 58 wt %, about 59 wt %, about 60 wt %, In one embodiment, the fertilizer comprises about 17 wt % of a plant material, about 13 wt % urea, about 12 wt % guar gum, about 6 wt % NaOH, about 6 wt % S-type hydrated lime, about 1.5 wt % sugar or molasses, about 0.15 weight % red iron oxide, about 0.15 weight % black iron oxide, and 44.3 wt % water. In one embodiment, a Composition of the Invention is a fertilizer comprising about 17 wt % of a protein source as described herein, about 13 wt % urea, about 12 wt % guar gum, about 6 wt % NaOH, about 6 wt % S-type hydrated lime, about 1.5 wt % sugar or molasses, about 0.15 weight % red iron oxide, about 0.15 weight % black iron oxide, and 44.3 wt % water.

Also provided herein is a method for making a plant fertilizer. In one embodiment, the method comprises admixing with sand or soil a Composition of the Invention. In other embodiments, the methods comprise admixing a Composition of the Invention and compost. In yet other embodiments, the method comprises admixing a Composition of the Invention with sand; soil; one or more water-soluble mineral nutrients, such nitrogen, phosphorous, potassium, calcium, ionic magnesium, iron, manganese, zinc, copper, boron or molybdenum; starch; fulvic acid; digested plant material; digested lignin; soluble seaweed; cane sugar; malt; beet vinasse; molasses; water-soluble hydrocolloid polysaccharides; compost tea extracts; vermicompost; cellulose; chitosan; a mineral salt, such as ammonium nitrate, ammonium phosphate, ammonium sulphate, calcium nitrate, calcium phosphate, calcium sulphate, magnesium nitrate, magnesium phosphate, magnesium sulphate, potassium nitrate, potassium phosphate, potassium sulphate, iron sulphate, iron phosphate, iron glycinate, iron lignosulphate, chelated iron (such as iron chelated via ethylene-diamine-tetra-acetic acid (EDTA) or iron chelated via diethylenetriamine pentaacetic acid (DTPA)), or urea; or a mixture thereof.

The present invention also provides methods for inducing plant growth, comprising contacting a plant seed, plant root, or soil in which a plant seed or root is present with a Composition of the Invention under conditions effective for inducing growth of the plant. The plant can be a flower, tree, or grass. In some embodiments, the plant produces, or is used as, an agricultural product, such as a vegetable, fruit or nut.

The Compositions of the Invention are useful for preventing erosion. Provided herein are methods for preventing soil, sand or road surface erosion, comprising applying to the soil, sand or road surface a Composition of the Invention under conditions effective to prevent erosion of the soil, sand or road surface. Erosion of soils, beaches and paved and unpaved road surfaces can be caused by environmental conditions, such as wind, rain, water flow, temperature change (e.g. freeze-thaw cycle) and physical traffic.

Soil, sand, dust, and other ground surfaces can be stabilized against erosion by treating these ground surfaces with a Composition of the Invention. The soil surface to be treated may be tilled or untilled and may contain plants or vegetation. The ground surface may be unpaved dirt and gravel road surfaces or paved road surfaces. In another embodiment, the ground surface is a paved, asphalt or concrete road surface. A Composition of the Invention can inhibit, reduce or prevent the erosion, rutting, cracking, formation of potholes, and washboarding of the road surface. A Composition of the Invention can be coated onto the soil or road surface. In another embodiment, a Composition of the Invention can be admixed with the soil, asphalt or concrete during preparation of the soil, asphalt or cement and the resulting admixture applied to where the soil is to be used or to the road.

Erosion of beaches caused by rainfall, wind and tidal water flows, including severe environmental conditions experienced during hurricanes, can also be inhibited, reduced or prevented by contacting the beach surface with a Composition of the Invention. A Composition of the Invention can be coated onto the beach surface. In another embodiment, a Composition of the Invention can be admixed with the sand of the beach and the admixture applied to the beach surface.

In one embodiment, the soil, sand (such as in a beach area), or road surface is treated with a Composition of the Invention. The Composition can be substantially anhydrous or aqueous. The Composition can be modified by adding up to 5%, such as about 0.125% to 5%, by weight of particulate metal oxides or sulfides containing metals. In one embodiment, the metal oxide or sulfide is any valent form of iron oxide and iron sulfide. These metal oxides or sulfides can be admixed with a Composition of the Invention during formation of the Composition of the Invention, or be subsequently added to and mixed. The admixture applied to the ground surfaces may additionally contain one or more additives, such as fillers, pigments, stabilizers, thickening agents, buffers, fertilizers, mineral salts and plant protection agents. Examples of fillers include waxes, paraffins, resin, lignin stabilizers, $SiO_2$, drilling muds and borax (sodium borate). In some embodiments, borax is separately applied as a post-treatment onto a ground surface after the ground surface has been treated with a Composition of the Invention. In some embodiments, the additive(s) are up to 20% by weight of the resulting composition.

A Composition of the Invention is useful to coat comminuted rock, such as crushed stone or gravel, to suppress dust. A Composition of the Invention can be applied to the surface of the crushed stone or gravel during the pulverization or the crushing procedure to reduce the emission of dust during comminution of the larger stone pieces. A Composition of the Invention can be in solution can be sprayed onto the surface of the gravel or crushed stone or after the deposition of the gravel or crushed stone on a ground surface such as a road bed, driveway or parking lot. A Composition of the Invention can be applied at a rate of 5 to 200 grams of the Composition per 100 ft$^2$ of stone surface to be coated.

In some embodiments, the ground surfaces are stabilized against erosion by treating the ground surface with 1 to 6000 grams of a Composition of the Invention per 100 ft$^2$ of ground surface area, such as from 5 to 20 grams of a Composition of the Invention per 100 ft$^2$ of soil or road ground surface area and 2000 to 6000 grams, such as 2000 to 4000 grams of a Composition of the Invention per 100 ft$^2$ of beach or sandy ground surface area. Beach areas to be stabilized against erosion may require higher end application rates due to the porosity of the sand and to provide stabilization of the sand against destructive wave action. A Composition of the Invention can be applied in solution by spraying or in granular form by spreading means such as a broadcast spreader or the like.

In some embodiments, a Composition of the Invention is added in granular form or in solution directly to cementitious or asphalt compositions in amounts of the Composition ranging from 0.0002 to 1%, such as 0.0001 to 0.1% by weight of the total cementitious or asphalt composition. The addition of a Composition of the Invention can improve tensile strength and internal adhesion properties of cement or asphalt. The incorporation of a Composition of the Invention into cement and asphalt can increase the elasticity and longevity of the subsequently formed cement or asphalt product or cementitious or asphalt paving coating, thereby reducing the likelihood of the product or coating to crack. A Composition of the Invention can also be added to the dry cement or asphalt during formation.

The following non-limiting examples illustrate various aspects of the present invention.

EXAMPLES

Example 1

An illustrative aqueous composition of the invention comprising plant material, but not comprising polysaccharide other than that present in or derived from the plant material, was prepared as follows. Citric acid (4.91 grams) was dissolved in 0.714 kg of 70% isopropanol at about 23° C. Corn gluten meal (2.28 kg) was added, and the resultant mixture was allowed to stir for 2 hours. 2.844 kg of a 50% aqueous sodium hydroxide solution was added to 13.6 kg of water, the resultant diluted sodium hydroxide solution was added to the isopropanol/corn gluten meal mixture, and the resultant mixture was allowed to stand for 6 hours. Sodium chloride (9.1 g) was then added, also with stirring. The resultant mixture was then allowed to stand an additional 2 hours. S-type hydrated lime (90.8 g) was then added with stirring, and the resultant mixture was stirred until uniform. The solids were allowed to settle, and the supernatant was decanted to provide the illustrative aqueous composition as the decanted supernatant.

Example 2

An illustrative aqueous composition of the invention comprising plant material and polysaccharide was prepared as follows. Citric acid (4.91 grams) was dissolved in 0.714 kg of 70% isopropanol at about 23° C. Corn gluten meal (2.28 kg) was added, and the resultant mixture was allowed to stir for 2 hours. 2.844 kg of a 50% aqueous sodium hydroxide solution was added to 13.6 kg of water, the resultant diluted sodium hydroxide solution was added to the isopropanol/corn gluten meal mixture, and the resultant mixture was allowed to stand for 6 hours. Guar gum (113.5 g) wetted with 70% isopropanol was then added to the isopropanol/corn gluten meal mixture with stirring. Sodium chloride (9.1 g) was then added, also with stirring. The resultant mixture was then allowed to stand an additional 2 hours. S-type hydrated lime (90.8 g) was then added with stirring, and the resultant mixture was stirred until uniform. The solids were allowed to settle, and the supernatant was decanted to provide the illustrative aqueous composition as the decanted supernatant.

Example 3

Figure 1B:
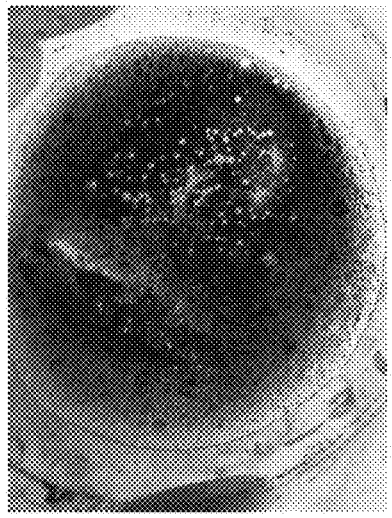

In a glass vessel, the aqueous composition of Example 1 (2.5 g) was combined with water (47.5 g) to provide an extractant. To the extractant was added 5 g of Athabasca oil sand. The pH of the resultant mixture was 13.2. The mixture was then stirred using a magnetic stir bar for 135 minutes at about 23° C. After 15 minutes of stirring, some extraction of oil from the oil sand was observed. Complete extraction of the oil, as determined by the observation of clean sand in the bottom of the vessel after a brief settling period, was not observed. FIGS. 1A-B are photographs showing a side view of the mixture in the vessel after 60 min of stirring then briefly allowing the mixture to settle (FIG. 1A), and a top view of the inside of the vessel after decanting the supernatant (FIG. 1B), also after 60 min of stirring. This example demonstrates that an illustrative Composition of the Invention is useful for extracting at least some hydrocarbon-containing oil from a substrate.

Example 4

Figure 2A:
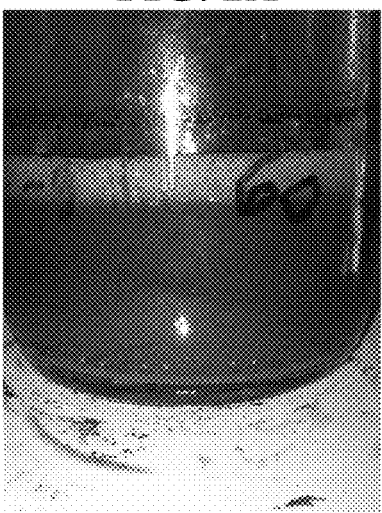
FIGS. 2A-B are photographs showing a side view of the vessel containing the mixture of Example 4 after 60 min of stirring then briefly allowing the mixture to settle (FIG. 2A), and a top view of the inside of the vessel after decanting the supernatant (FIG. 2B), also after 60 min of stirring.
Figure 2B:
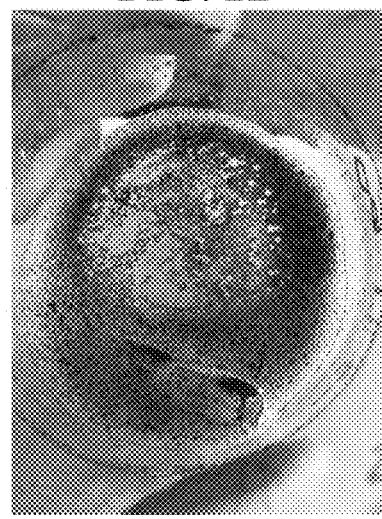

In a glass vessel, the aqueous composition of Example 1 (2.5 g) was combined with water (47.5 g) to provide an extractant. To the extractant was added 5 g of Athabasca oil sand. The pH of the mixture was then adjusted to about 11.1 with 1M citric acid. The mixture was then stirred using a magnetic stir bar for 135 minutes at about 23° C. After 15 minutes of stirring, some extraction of oil from the oil sand was observed. Complete extraction of the oil, as determined by the observation of clean sand in the bottom of the vessel after a brief settling period, was observed after 60 min of stirring. FIGS. 2A-B are photographs showing a side view of the mixture in the vessel after 60 min of stirring then briefly allowing the mixture to settle (FIG. 2A), and a top view of the inside of the vessel after decanting the supernatant (FIG. 2B), also after 60 min of stirring. This example demonstrates that an illustrative Composition of the Invention is useful for extracting hydrocarbon-containing oil from a substrate.

Example 5

Figure 3A:
FIGS. 3A-B are photographs showing a side view of the vessel containing the mixture of Example 5 after 60 min of stirring then briefly allowing the mixture to settle (FIG. 3A), and a top view of the inside of the vessel after decanting the supernatant (FIG. 3B), also after 60 min of stirring.
Figure 3B:
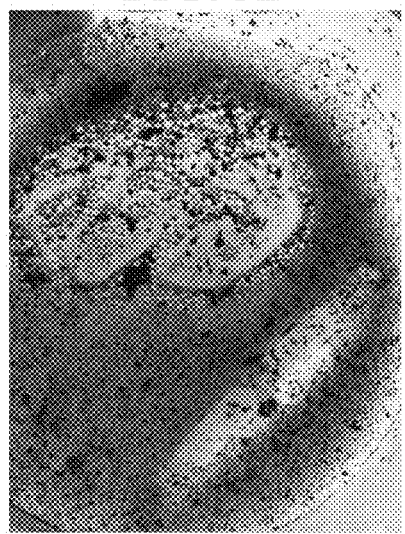

In a glass vessel, the aqueous composition of Example 1 (2.5 g) was combined with water (47.5 g) to provide an extractant. To the extractant was added 5 g of Athabasca oil sand. The pH of the mixture was then adjusted to about 9.1 with 1M citric acid. The mixture was then stirred using a magnetic stir bar for 135 minutes at about 23° C. After 15 minutes of stirring, some extraction of oil from the oil sand was observed. Complete extraction of the oil, as determined by the observation of clean sand in the bottom of the vessel after a brief settling period, was observed after 60 min of stirring. FIGS. 3A-B are photographs showing a side view of the mixture in the vessel after 60 min of stirring then briefly allowing the mixture to settle (FIG. 3A), and a top view of the inside of the vessel after decanting the supernatant (FIG. 3B), also after 60 min of stirring. This example demonstrates that an illustrative Composition of the Invention is useful for extracting hydrocarbon-containing oil from a substrate.

Example 6

Figure 4A:
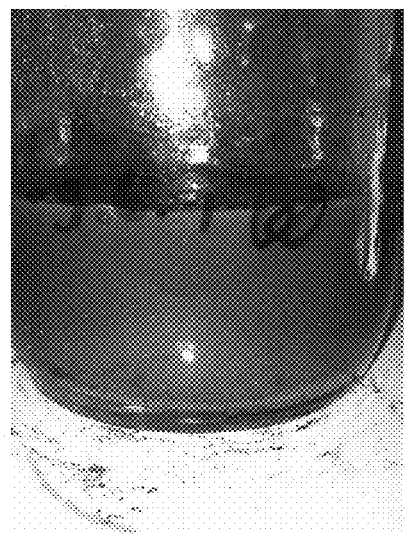
FIGS. 4A-B are photographs showing a side view of the vessel containing the mixture of Example 6 after 60 min of stirring then briefly allowing the mixture to settle (FIG. 4A), and a top view of the inside of the vessel after decanting the supernatant (FIG. 4B), also after 60 min of stirring.
Figure 4B:

In a glass vessel, the aqueous composition of Example 1 (2.5 g) was combined with water (47.5 g) to provide an extractant. To the extractant was added 5 g of Athabasca oil sand. The pH of the mixture was then adjusted to about 6.9 with 1M citric acid. The mixture was then stirred using a magnetic stir bar for 135 minutes at about 23° C. After 15 minutes of stirring, some extraction of oil from the oil sand was observed. Complete extraction of the oil, as determined by the observation of clean sand in the bottom of the vessel after a brief settling period, was observed after 60 min of stirring. FIGS. 4A-B are photographs showing a side view of the mixture in the vessel after 60 min of stirring then briefly allowing the mixture to settle (FIG. 4A), and a top view of the inside of the vessel after decanting the supernatant (FIG. 4B), also after 60 min of stirring. This example demonstrates that an illustrative Composition of the Invention is useful for extracting hydrocarbon-containing oil from a substrate.

Example 7

Figure 5A:
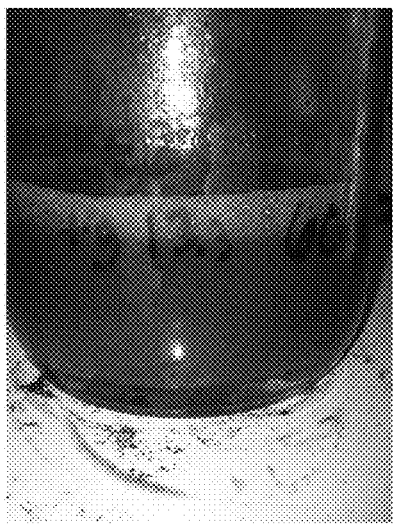
FIGS. 5A-B are photographs showing a side view of the vessel containing the mixture of Example 7 after 60 min of stirring then briefly allowing the mixture to settle (FIG. 5A), and a top view of the inside of the vessel after decanting the supernatant (FIG. 5B), also after 60 min of stirring.
Figure 5B:

In a glass vessel, the aqueous composition of Example 2 (2.5 g) was combined with water (47.5 g) to provide an extractant. To the extractant was added 5 g of Athabasca oil sand. The pH of the resultant mixture was 13.2. The mixture was then stirred using a magnetic stir bar for 135 minutes at about 23° C. After 15 minutes of stirring, some extraction of oil from the oil sand was observed. Complete extraction of the oil, as determined by the observation of clean sand in the bottom of the vessel after a brief settling period, was not observed. FIGS. 5A-B are photographs showing a side view of the mixture in the vessel after 60 min of stirring then briefly allowing the mixture to settle (FIG. 5A), and a top view of the inside of the vessel after decanting the supernatant (FIG. 5B), also after 60 min of stirring. This example demonstrates that an illustrative Composition of the Invention is useful for extracting at least some hydrocarbon-containing oil from a substrate.

Example 8

Figure 6A:
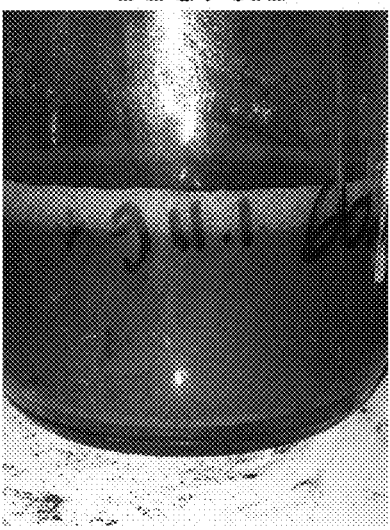
FIGS. 6A-B are photographs showing a side view of the vessel containing the mixture of Example 8 after 60 min of stirring then briefly allowing the mixture to settle (FIG. 6A), and a top view of the inside of the vessel after decanting the supernatant (FIG. 6B), also after 60 min of stirring.
Figure 6B:
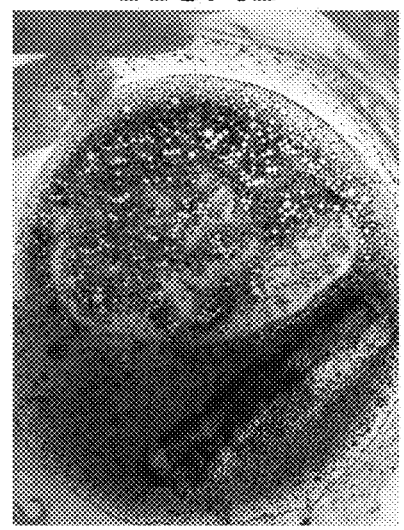

In a glass vessel, the aqueous composition of Example 2 (2.5 g) was combined with water (47.5 g) to provide an extractant. To the extractant was added 5 g of Athabasca oil sand. The pH of the mixture was then adjusted to about 11.1 with 1M citric acid. The mixture was then stirred using a magnetic stir bar for 135 minutes at about 23° C. After 15 minutes of stirring, some extraction of oil from the oil sand was observed. Complete extraction of the oil, as determined by the observation of clean sand in the bottom of the vessel after a brief settling period, was observed after 60 min of stirring. FIGS. 6A-B are photographs showing a side view of the mixture in the vessel after 60 min of stirring then briefly allowing the mixture to settle (FIG. 6A), and a top view of the inside of the vessel after decanting the supernatant (FIG. 6B), also after 60 min of stirring. This example demonstrates that an illustrative Composition of the Invention is useful for extracting hydrocarbon-containing oil from a substrate.

Example 9

Figure 7A:
FIGS. 7A-B are photographs showing a side view of the vessel containing the mixture of Example 9 after 60 min of stirring then briefly allowing the mixture to settle (FIG. 7A), and a top view of the inside of the vessel after decanting the supernatant (FIG. 7B), also after 60 min of stirring.
Figure 7B:
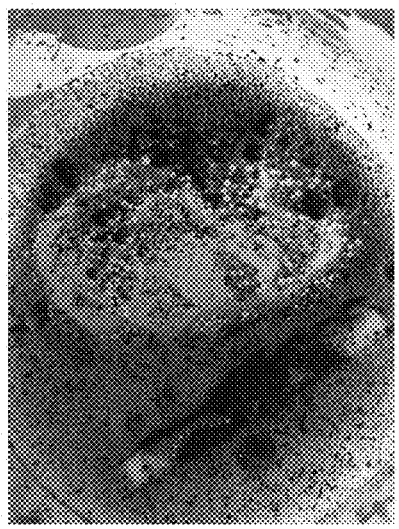

In a glass vessel, the aqueous composition of Example 2 (2.5 g) was combined with water (47.5 g) to provide an extractant. To the extractant was added 5 g of Athabasca oil sand. The pH of the mixture was then adjusted to about 9.1 with 1M citric acid. The mixture was then stirred using a magnetic stir bar for 135 minutes at about 23° C. After 15 minutes of stirring, some extraction of oil from the oil sand was observed. Complete extraction of the oil, as determined by the observation of clean sand in the bottom of the vessel after a brief settling period, was observed after 60 min of stirring. FIGS. 7A-B are photographs showing a side view of the mixture in the vessel after 60 min of stirring then briefly allowing the mixture to settle (FIG. 7A), and a top view of the inside of the vessel after decanting the supernatant (FIG. 7B), also after 60 min of stirring. This example demonstrates that an illustrative Composition of the Invention is useful for extracting hydrocarbon-containing oil from a substrate.

Example 10

Figure 8A:
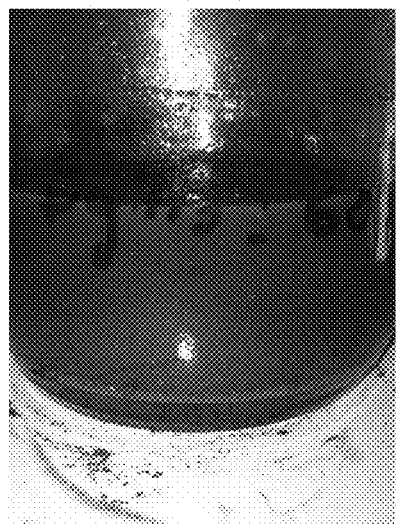
FIGS. 8A-B are photographs showing a side view of the vessel containing the mixture of Example 10 after 60 min of stirring then briefly allowing the mixture to settle (FIG. 8A), and a top view of the inside of the vessel after decanting the supernatant (FIG. 8B), also after 60 min of stirring.
Figure 8B:
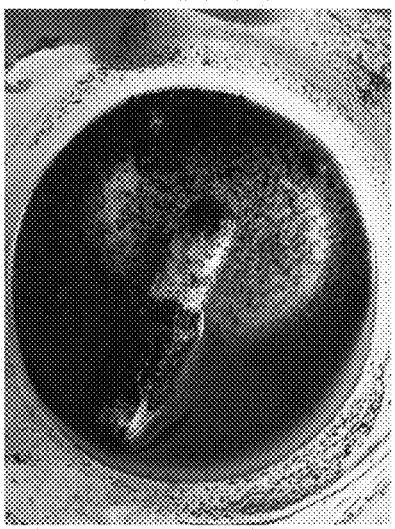

In a glass vessel, the aqueous composition of Example 2 (2.5 g) was combined with water (47.5 g) to provide an extractant. To the extractant was added 5 g of Athabasca oil sand. The pH of the mixture was then adjusted to about 7 with 1M citric acid. The mixture was then stirred using a magnetic stir bar for 135 minutes at about 23° C. After 15 minutes of stirring, some extraction of oil from the oil sand was observed. Complete extraction of the oil, as determined by the observation of clean sand in the bottom of the vessel after a brief settling period, was observed after 60 min of stirring. FIGS. 8A-B are photographs showing a side view of the mixture in the vessel after 60 min of stirring then briefly allowing the mixture to settle (FIG. 8A), and a top view of the inside of the vessel after decanting the supernatant (FIG. 8B), also after 60 min of stirring. This example demonstrates that an illustrative Composition of the Invention is useful for extracting hydrocarbon-containing oil from a substrate.

Polycyclic aromatic hydrocarbons (PAHs) and their alkylated analogs are ubiquitous environmental pollutants. They are in fossil fuels, and their by-products can enter the environment from natural seeps or runoff from asphalt. Incomplete combustion of organic materials can result in transporting these compounds over long distances as gaseous molecules or organically-bound particulate matter. In addition, there are tens of thousands of coal-tar contaminated gas plants worldwide that are and will continue to contribute to PAH pollution.

Some PAHs are toxic, mutagenic, and carcinogenic, and therefore pose risk to human health and the environment. Alkylated PAHs have been shown to contribute substantially to the toxicity of PAH mixtures, in some cases accounting for 80% of the toxic burden. Similarly, PASH bioaccumulates and can be toxic, mutagenic, and carcinogenic.

The US EPA provides guidelines for estimating the hazards posed by contaminated soils and sediments based on the concentration of 18 parent PAH and 16 C1 to C4 alkylated homologs. Thus, the removal and/or recovery of PAH is of importance in the remdiation of environmentally compromised sites and/or in the extraction of oil. The following Examples 11 and 12 demonstrate that illustrative Compositions of the Invention are effective for removing or extracting PAH from coal tar or from Athabasca oil sand.

Example 11

In a glass vessel, the aqueous composition of Example 1 (2.5 g) was combined with water (47.5 g) to provide an extractant. Athabasca oil sand (5 g) was added to the vessel. The resultant mixture was stirred using a magnetic stir bar for 4 hr at about 23° C., and an oil ball was formed. The PAH content of the oil sand was measured by GC-MS before and after extraction, to determine the extractant's extraction efficiency. PAHs whose concentration was detected include naphthalene, fluorene, phenanthrene, pyrene, chrysene, and $C_1$-$C_4$ homologs thereof. A $C_1$ homolog of a PAH is a PAH having a methyl group. A $C_2$ homolog of a PAH is a PAH having, for example, an ethyl group or two methyl groups. A $C_3$ homolog of a PAH is a PAH having, for example, a methyl and an ethyl group, three methyl groups, an n-propyl group or an i-propyl group. A $C_4$ homolog of a PAH is a PAH having, for example, two ethyl groups, four methyl groups, an ethyl group and two methyl groups, a methyl group and an n-propyl group, a methyl group and an i-propyl group, an n-butyl group, a sec-butyl group, and i-butyl group or a t-butyl group. The results of these analyses are shown in Table 1 below:

TABLE 1

PAH Concentrations in Oil Sand Before and
After Extraction (μg PAH/g Sand)

| PAH | Before Extraction (μg/g) | After Extraction (μg/g) |
|---|---|---|
| Naphthalene | not detected | not detected |
| $C_1$ homolog | not detected | not detected |
| $C_2$ homolog | not detected | not detected |
| $C_3$ homolog | not detected | not detected |
| $C_4$ homolog | not detected | not detected |
| Fluorene | not detected | not detected |
| $C_1$ homolog | 3.3 | not detected |
| $C_2$ homolog | not detected | not detected |
| $C_3$ homolog | not detected | not detected |
| $C_4$ homolog | not detected | not detected |
| Phenanthrene | 3.6 | not detected |
| $C_1$ homolog | 24.1 | 0.4 |
| $C_2$ homolog | 38.9 | 0.6 |
| $C_3$ homolog | 47.2 | 0.7 |
| $C_4$ homolog | 7.7 | not detected |
| Pyrene | 5.6 | not detected |
| $C_1$ homolog | 2.1 | not detected |
| $C_2$ homolog | not detected | not detected |
| $C_3$ homolog | not detected | not detected |
| $C_4$ homolog | not detected | not detected |
| Chrysene | 2.7 | not detected |
| $C_1$ homolog | 9.0 | not detected |
| $C_2$ homolog | 9.2 | not detected |
| $C_3$ homolog | not detected | not detected |
| $C_4$ homolog | not detected | not detected |

This example demonstrates that an illustrative Composition of the Invention is useful for extracting PAH-containing oil from a substrate.

Based on the low PAH content of the Athabasca oil sand, as shown in Example 11 above, relative to coal tar, as shown in Example 12, below, it was important to confirm for a larger group of PAH if the percent reduction in PAH content is characteristic of the present extraction methods employing Compositions of the Invention. Thus, a coal tar sand was extracted as described in Example 12, below.

Example 12

In a glass vessel, the aqueous composition of Example 1 (2.5 g) was combined with water (47.5 g) to provide an extractant. Coal tar sand from a North Carolina gasification plant site (5 g, 15 wt % coal tar) was added to the extractant. The resultant mixture was stirred using a magnetic stir bar for 90 minutes at about 23° C. Extraction of the coal tar from the sand was observed after 10 minutes, and a ball of coal tar was observed at 90 minutes. The polycyclic aromatic hydrocarbon (PAH) content of the coal tar sand was measured by GC-MS before and after above-described extraction to determine the extractant's extraction efficiency. The results of these analyses are shown in Table 2 below:

TABLE 2

PAH Concentrations in Coal Tar Sand Before and
After Extraction (mg PAH/kg) Sand)

| PAH | Before Extraction | After Extraction | % Extraction |
|---|---|---|---|
| Acenaphthene | 1.3 | 0.0 | 100 |
| Acenaphthylene | 392.4 | 7.4 | 98.1 |
| Anthracene | 418.8 | 8.5 | 98.0 |
| benz[a]anthracene | 299.9 | 6.7 | 97.8 |
| benzo[a]pyrene | 216.1 | 4.8 | 97.8 |
| Benzo[b]fluoranthene | 103.9 | 2.6 | 97.5 |
| benzo[ghi]perylene | 77.1 | 1.7 | 97.9 |
| benzo[k]fluoranthene | 126.6 | 2.6 | 98.0 |
| Chrysene | 299.3 | 6.8 | 97.7 |

TABLE 2-continued

PAH Concentrations in Coal Tar Sand Before and
After Extraction (mg PAH/kg) Sand)

| PAH | Before Extraction | After Extraction | % Extraction |
|---|---|---|---|
| dibenz[ah]anthracene | 23.2 | 0.4 | 98.1 |
| Fluoranthene | 712.5 | 11.7 | 98.4 |
| Fluorene | 419.5 | 8.3 | 98.0 |
| Indeno[1,2,3-cd]pyrene | 79.9 | 1.5 | 98.1 |
| Naphthalene | 502.5 | 8.1 | 98.4 |
| Phenanthrene | 1444.5 | 31.4 | 97.8 |
| Pyrene | 853.2 | 15.1 | 98.2 |

This example demonstrates that an illustrative Composition of the Invention is useful for extracting PAH-containing coal tar from a substrate.

The percent decrease in PAH content in the tar sand as shown in Example 12, above, was consistent from homolog to homolog. Since the concentration of the various PAHs measured decreases in similar amounts, these data indicate that the extractant removes PAH from the coal tar sand without selectivity.

Example 13

Figure 9:
FIGS. 9 and 10 are photographs showing a top-down (FIG. 9) and side (FIG. 10) view of the contents in the beaker in Example 13 before stirring.
Figure 10:
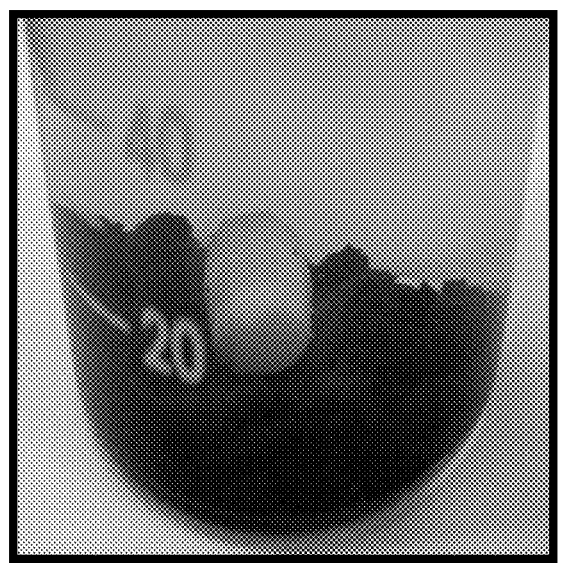

Athabasca oil sand (5 g) was added to a 100 ml glass beaker. An extractant of a mixture of the aqueous composition of Example 1 (2.5 g) in water (47.5 g) was added to the Athabasca oil sand (5 g) at about 23° C. FIGS. 9 and 10 are photographs showing a top-down (FIG. 9) and side (FIG. 10) view of the contents in the beaker before stirring (see also white magnetic stir bar in photograph). Evident in FIGS. 9 and 10 is the lumpiness of the oil sands, and that the sand is completely surrounded by oil. Also shown are air bubbles, produced upon addition of the extractant to the oil sands. In contrast, no bubbles appeared when pouring merely water over the oil sands or when pouring the extractant into an empty beaker. The extractant was yellow in color.

Figure 11:
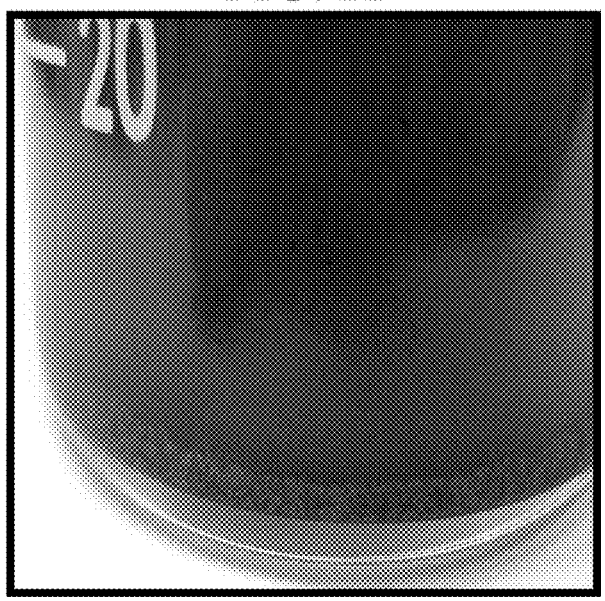
FIG. 11 is a photograph showing the contents of the beaker in Example 13 after stirring for 4 min, then allowing most of the solids to settle.

The mixture of extractant and oil sand was then stirred. FIG. 11 is a photograph showing the contents of the beaker after stirring for 4 min, then allowing most of the solids to settle. FIG. 11 shows stringers of oil separating from sand. This result is consistent with conventional, elevated temperature, water-based oil sand extraction processes. FIG. 11 shows separation occurring at room temperature within the same 5 minute timeframe as in current conventional, elevated temperature, water-based oil sand extraction processes. Evident is the change in color of the solution and the appearance of loosely scattered "free" oil and sand particles from the lumpy oil sands. As particles settle, oil-containing sands sit on top of "cleaner" sand as it is beginning to separate from the lumpier oil sands.

Figure 12:
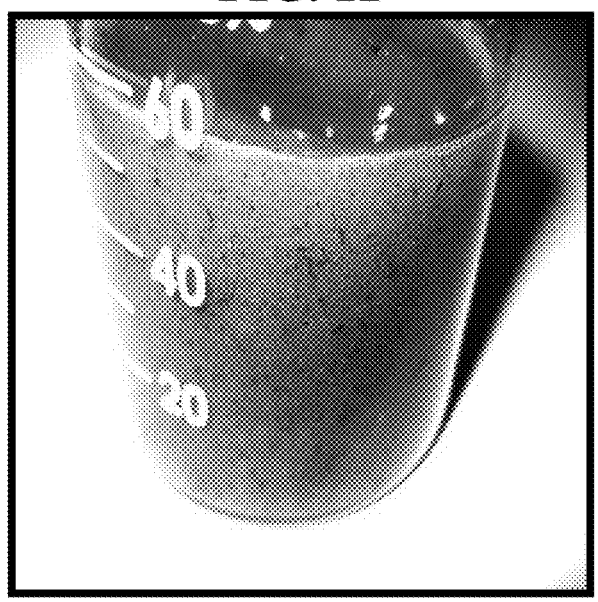
FIG. 12 is a photograph showing the contents of the beaker in Example 13 after stirring for 10 minutes.
Figure 13:
FIG. 13 is a photograph showing the contents of the beaker in Example 13, showing that sand free of oil that had settled to the bottom of the beaker a few minutes after stirring was stopped.
Figure 14:
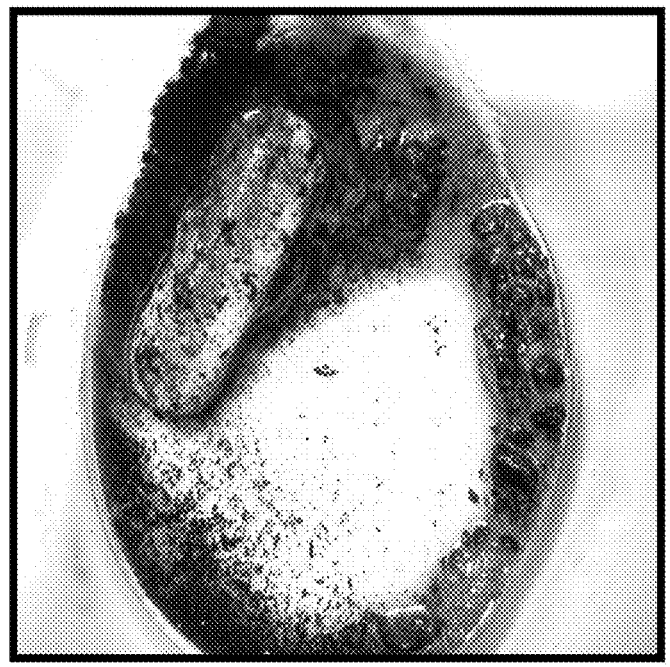
FIG. 14 is a photograph showing the contents of the beaker in Example 13, showing that agglomerating oil deposits sat on top of the sand after decanting the solution into another beaker.

FIG. 12 is a photograph showing the contents of the beaker after stirring for 10 minutes. Evident are longer stringers of "free" oil separated from the sands. Conversely, FIG. 13 is a photograph showing sand "free" of oil that has settled to the bottom of the beaker a few minutes after stirring was stopped. FIG. 14 is a photograph showing the agglomerating oil deposits sitting on top of the sand after decanting the solution into another beaker.

Figure 15:
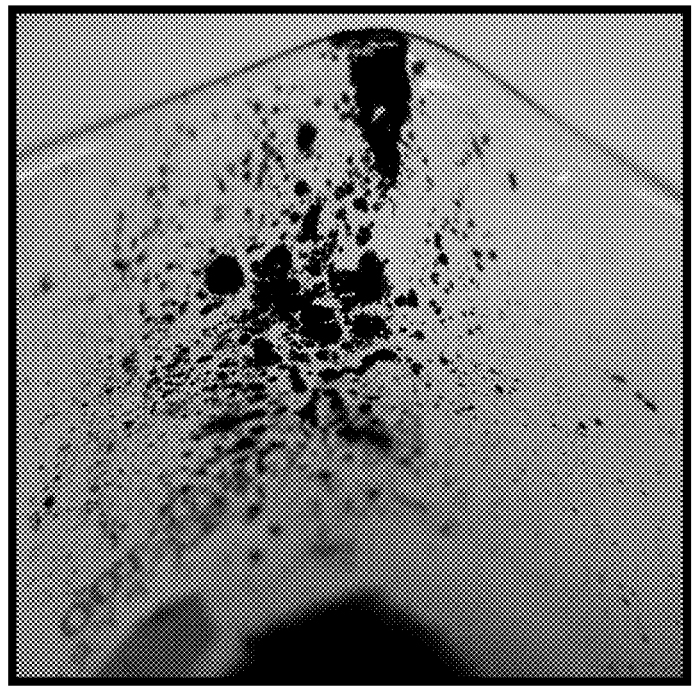
FIGS. 15-16 are photographs showing the contents of the beaker of Example 13 after stirring 30 min, then decanting the solution into another beaker.
Figure 16:

FIGS. 15-16 are photographs showing the contents of the beaker after stirring 30 minutes and then decanting the solution into a second beaker. FIG. 15 is a photograph of "free" oil sticking to the glass of the beaker in which the oil sand and extractant were stirred, after decanting the extractant liquid comprising some extracted oil into a second beaker. FIG. 16 is a photograph showing the remaining sand and oil in the beaker in which the oil sand and extractant were stirred after decanting the extractant liquid comprising some extracted oil into the second beaker. As shown in FIG. 16, the remaining oil in the bottom of the beaker begins to pool as a dense, non-aqueous phase liquid (DNAPL), which, for the most part, has separated from the sand.

Figure 17:
FIG. 17 is a photograph showing the sand, oil and magnetic stir bar remaining in the beaker of Example 13 after stirring for 1 hour and decanting the resultant supernatant.
Figure 18:
FIG. 18 is a photograph showing the oil remaining on the glass of the first beaker of Example 13 after transferring the sand, oil and extractant to a second beaker.

FIG. 17 is a photograph showing the sand, oil and magnetic stir bar remaining in the beaker after stirring for 1 hour and decanting the resultant supernatant. FIG. 18 is a photograph showing the oil remaining on the glass of the first beaker after transferring the sand, oil and extractant to a second beaker.

This example demonstrates that an illustrative Composition of the Invention is useful for extracting oil from Athabasca oil sands.

Example 14

Athabasca oil sand (5 g comprising 15±6 wt % oil and 83±6% sand) was combined with 50 mL of toluene and stirred at about 23° C. This toluene extraction was repeated seven times for each 5 g sample of Athabasca oil sand. The extractions were performed in triplicate (i.e., three different samples). A total of 2% of the mass of the oil sand was lost during separation of "free" oil from sand. As reported below, mass of oil (wt %) or mass of sand (wt %) are reported as the mass percent of each versus the total sample weight (i.e., mass of oil=oil extracted from Athabasca oil sand (g)/total mass of original Athabasca oil sand sample (g)×100; mass of sand=mass of sand remaining after extraction (g)/mass of original Athabasca oil sand sample (g)×100). Variation among the three extractions is reported as RSD (relative standard deviation). A summary of these analyses is shown below in Table 3:

TABLE 3

Mass Percent Oil and Sand in Athabasca Oil Sand by Solvent Extraction

|  | Extraction 1 | Extraction 2 | Extraction 3 |
| --- | --- | --- | --- |
| Mass of Oil (wt %) | 16% | 16% | 14% |
| Mass of Sand (wt %) | 84% | 82% | 84% |
| Average Mass of Oil (wt %) | 15% | Average Mass of Sand (wt %) | 83% |
| RSD | 6% | RSD | 1% |

The Athabasca oil sand was also analyzed by Alberta Innovates—Technology Futures of Canada to determine its total oil, water and solids content, as shown below in Table 4:

TABLE 4

Mass Percent Oil, Water and Solids and Sand in Athabasca Oil Sand by Solvent Extraction

| Total Athabasca Oil Sand (grams) | Total Mass Recovered (grams) | Oil (grams) | Water (grams) | Solids (grams) | Oil (wt %) | Water (wt %) | Solids (wt %) | Total Recovery (%) |
| --- | --- | --- | --- | --- | --- | --- | --- | --- |
| 87.03 | 86.18 | 10.68 | 1.00 | 74.50 | 12.27 | 1.15 | 85.6 | 99.02 |

In a glass vessel, the aqueous composition of Example 1 (2.5 g) was combined with water (47.5 g) to provide an extractant. Athabasca oil sand (5 g) was added to the extractant. The mixture of oil sand and extractant was stirred using a magnetic stir bar for 4 hr at about 23° C. Oil recovery extraction efficiency after 4 hr stirring, based on total oil present in the Athabasca oil sand, was 84±10 wt % based on the oil sand composition as shown in Table 3, above. However, if the oil sand composition data from the analyses performed by Alberta Innovates—Technology Futures of Canada in Table 4 above are used as the baseline for oil content in the oil sands, the extraction efficiency of an illustrative Composition of the Invention approaches 100%. These findings are impressive when contrasted with commercial recoveries of 80-95 wt % of oil from oil sands given that the present illustrative Composition of the Invention was employed at room temperature, whereas commercial extractions processes operate between 35° C. and 80° C. and need surfactants, steam, and air.

Figure 19:
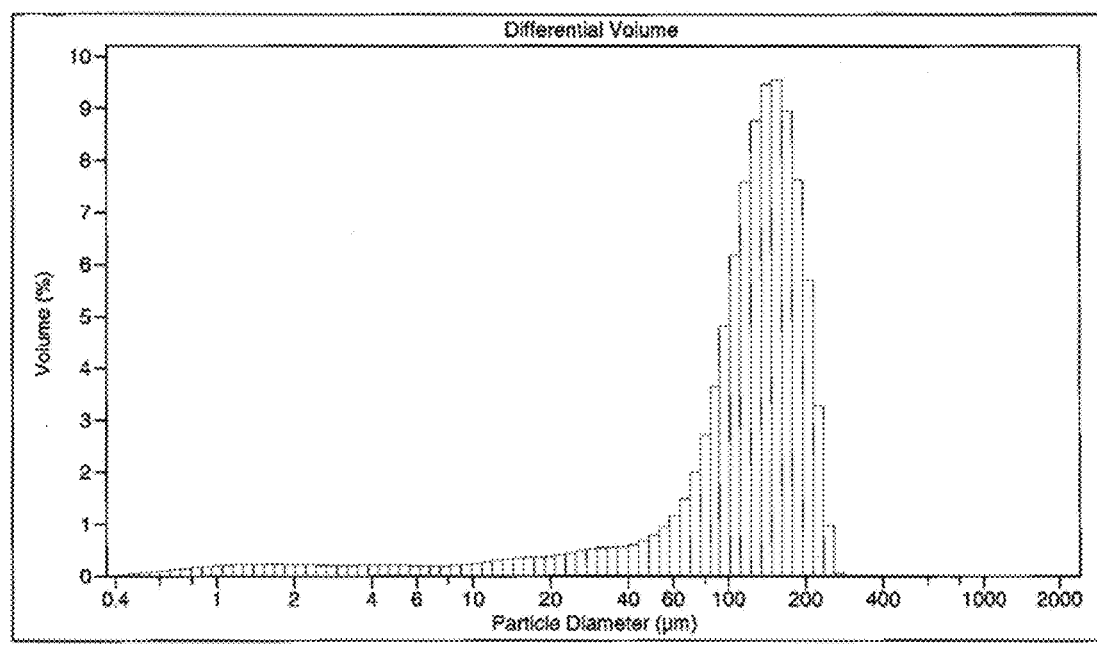
FIG. 19 is a chart showing the size distribution of the solids in the Athabasca oil sands of Example 14.

The particle-size distribution of the solids in the Athabasca oil sands was also determined (FIG. 19). The values from the particle size distribution analysis FIG. 19 were as follows:

| Volume Statistics (Arithmetic) Calculations from 0.375 µm to 2000 µm | | | |
| --- | --- | --- | --- |
| Volume: | 100% | | |
| Mean: | 121.8 µm | S.D.: | 59.13 µm |
| Median: | 127.9 µm | Variance: | 3496 µm² |
| Mean/Median ratio: | 0.953 | C.V.: | 48.5% |
| Mode: | 153.8 µm | Skewness: | −0.365 Left skewed |
| | | Kurtosis: | −0.462 Platykurtic |
| $d_{10}$: 24.59 µm $d_{50}$: 127.9 µm $d_{90}$: 194.4 µm | | | |
| <10% | <25% | <50% | <75% | <90% |
| 24.59 µm | 87.78 µm | 127.9 µm | 164.1 µm | 194.4 µm |

In summary, these findings show that an illustrative Composition of the Invention can provide at least as efficient extraction of oil from Athabasca oil sand relative to conventional, elevated temperature, water-based oil sand extraction processes.

Example 15

Athabasca oil sand (5 g) was combined with water (50 g) and stirred 4 hr at room temperature. The resultant mixture did not comprise a Composition of the Invention.

No extraction of oil from the oil sand was observed.

Example 16

To quantify the amount of protein present in illustrative aqueous compositions of the invention, a Biuret assay was employed. Each aqueous composition described in Table 5, below, was assayed to determine total protein concentration in parts per thousand (ppt). In each experiment, a first solution was prepared by dissolving 3.46 g of cupric sulfate in 20 mL of 50° C. water. A second solution was prepared by dissolving 34.6 g of sodium citrate and 20.0 g of sodium carbonate in 80 mL of 50° C. water. After allowing the first and second solutions to cool to 23° C., the first and second solutions were combined and mixed, yielding the Biuret assay reagent. Commercially sourced zein was dissolved in 70% isopropanol, and a calibration curve using various concentrations of zein was constructed. To measure the concentration of protein in the various aqueous compositions listed in Table 5, comprising as defined in Example 24 below, one mL of the aqueous composition was admixed with 1 ml of a 6 parts:100 (weight/weight) sodium hydroxide solution. To this mixture was added 0.4 mL of the Biuret assay reagent; providing a total volume was 2.4 mL. The test mixture's absorbance was measured at 545 nm in a 1 cm polystyrene cuvette after approximately 90 minutes. The absorbance was correlated to the calibration curve to provide protein concentration in the test mixture in parts per thousand. The results of the Biuret assay experiments are shown below:

TABLE 5

Protein concentration of Illustrative Aqueous Compositions as Determined via Biuret Assay.

| Aqueous Composition | Protein Source | Mass of NaOH (g) | Mass of Protein Source (g) | Protein Concentration (ppt) |
|---|---|---|---|---|
| 4.1 | Corn Gluten Meal | 15.9 | 39.8 | 53.4 |
| 10.2.1 | Corn Gluten Meal | 15.9 | 19.9 | 41.3 |
| 12.2.6 | Wheat Germ | 45.0 | 19.9 | 35.4 |
| 12.2.2 | Wheat Germ | 30.0 | 19.9 | 30.0 |
| 12.1.6 | Wheat Germ | 45.0 | 19.9 | 32.5 |
| 13.2.4 | Flax Seed Meal | 15.9 | 19.9 | 21.1 |
| 2.1.7 | Corn Gluten Meal | 15.9 | 19.9 | 23.0 |
| 13.2.3 | Flax Seed Meal | 45.0 | 19.9 | 15.5 |

Example 17

Approximately 5 ml of light tar oil obtained from an industrial oil storage tank in New Jersey (light tar oil is an oil having a viscosity similar to room-temperature honey or syrup, which is less dense than water, and is pourable) was introduced into each of two glass beakers. The light tar oil, while less dense than water, adhered to the bottom of the glass beaker. To the first beaker was added approximately 50 ml of water (labeled "water"). To the second beaker was added approximately 50 ml of a solution comprising 5 parts of the composition of Example 1 and 95 parts water by weight (labeled "Example 1").

Figure 20:
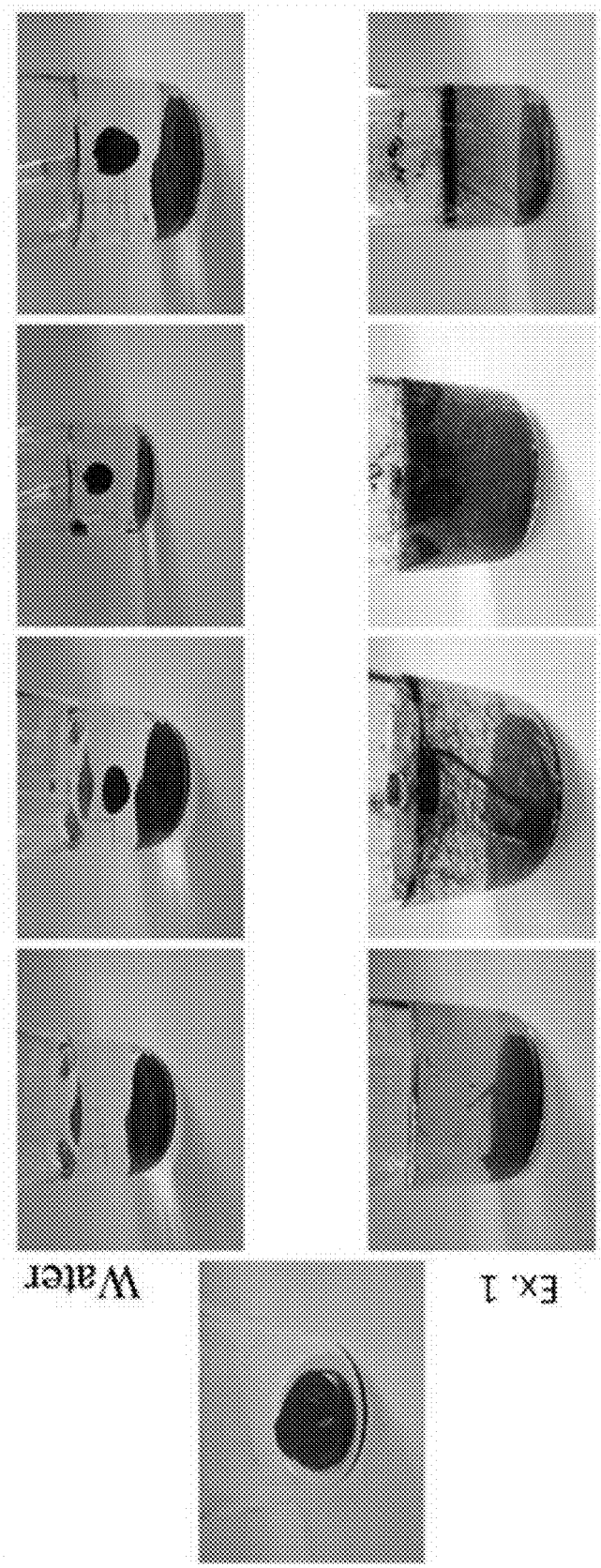
FIG. 20 depicts a series of photographs showing the contents of the beakers in Example 17, illustrating the effects of adding a solution comprising 5 parts of the composition of Example 1 and 95 parts water by weight to light tar oil in a glass beaker with subsequent stirring, and the effect of adding water to light tar oil in a glass beaker with subsequent stirring.

FIG. 20 is a series of photographs showing the effects of a solution comprising 5 parts of the composition of Example 1 and 95 parts water by weight versus water on light tar oil. The first photograph, on the far left, shows the light tar oil in the bottom of a glass beaker before the addition of either water or a Composition of the Invention. The top row of photographs is a time-lapse set of images showing the effects of adding water to light tar oil as described. Although the mechanical effect of pouring water spreads the light tar oil apart, it does not disperse the light tar oil in solution. As shown in FIG. 20, stirring with a glass pipette does not disperse the light tar oil; instead the light tar oil sticks to the beaker and the pipette. After vigorous stirring with the pipette, only small balls of light tar oil are formed, which eventually float to the surface.

In contrast, the bottom row of photographs in FIG. 20 illustrates the effect of a solution comprising 5 parts of the composition of Example 1 and 95 parts water by weight on the light tar oil. Immediately upon addition, "stringers" of light tar oil begin to from the tar oil and are released from the mass of tar oil adhering to the bottom of the beaker. Stirring the mixture with a glass pipette, as shown, releases more stringers, and the mixture becomes dark with the amount of released light tar oil. After allowing the mixture to stand for approximately 20 seconds, the light tar oil begins to float to the top of the mixture. This experiment illustrates the ability of a Composition of the Invention to remove light tar oil from a substrate.

Example 18

Approximately 5 ml of coal tar obtained from a utility plant in North Carolina was introduced into each of two glass beakers. The coal tar adhered to the bottom of the glass beaker. To the first beaker was added approximately 50 ml of water (labeled "water"). To the second beaker was added approximately 50 ml of a solution comprising 5 parts of the composition of Example 1 and 95 parts water by weight (labeled "Ex. 1").

Figure 21:
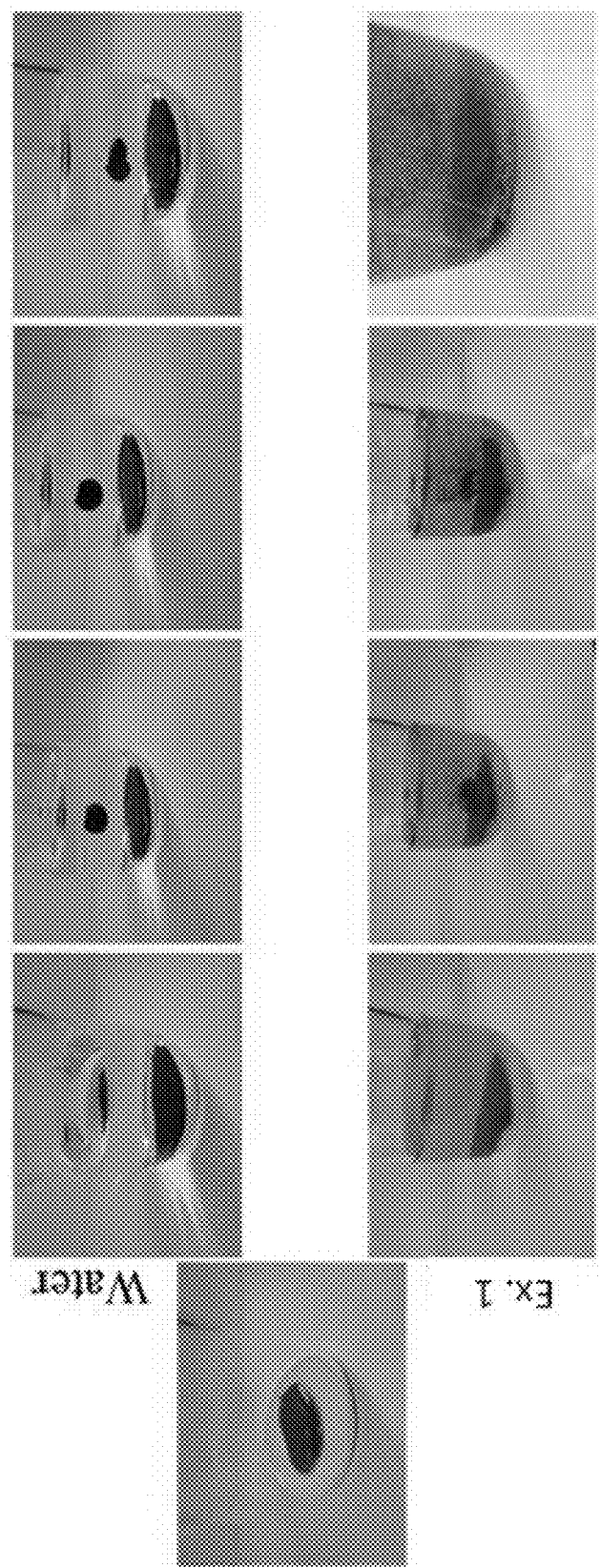
FIG. 21 depicts a series of photographs showing the contents of the beakers in Example 18, illustrating the effects of adding a solution comprising 5 parts of the composition of Example 1 and 95 parts water by weight to coal tar in a glass beaker with subsequent stirring, and the effect of adding water to coal tar in a glass beaker with subsequent stirring.

FIG. 21 is a series of photographs showing the effects of a solution comprising 5 parts of the composition of Example 1 and 95 parts water by weight versus water on coal tar. The first photograph, on the far left, shows the coal tar in the bottom of a glass beaker before the addition of either water or a Composition of the Invention. The top row of photographs is a time-lapse set of images showing the effects of adding water to coal tar as described. The mechanical effect of pouring water on coal tar does not disperse any of the coal tar in solution. As shown, stirring with a glass pipette also does not disperse the coal tar; instead the coal tar sticks to the beaker and the pipette. After vigorous stirring with the pipette, no coal tar is released from the mass adhered to the bottom of the beaker.

In contrast, the bottom row of photographs in FIG. 21 illustrates the effect of a solution comprising 5 parts of the composition of Example 1 and 95 parts water by weight on the coal tar. Upon stirring, the coal tar forms stringers in solution. The solution darkens with increased stirring, as more coal tar is liberated from the mass of coal tar adhered to the bottom of the beaker. Upon standing, the coal tar forms balls, which sink to the bottom of the beaker. This experiment illustrates the ability of a Composition of the Invention to remove coal tar from a substrate.

Example 19

Approximately 10 ml of oil-contaminated sludge, comprising sediment and oil, was introduced into each of two glass beakers. To the first beaker was added approximately 50 ml of water (labeled "water"). To the second beaker was added approximately 50 ml of a solution comprising 5 parts of the composition of Example 1 and 95 parts water by weight (labeled "Ex. 1").

Figure 22:
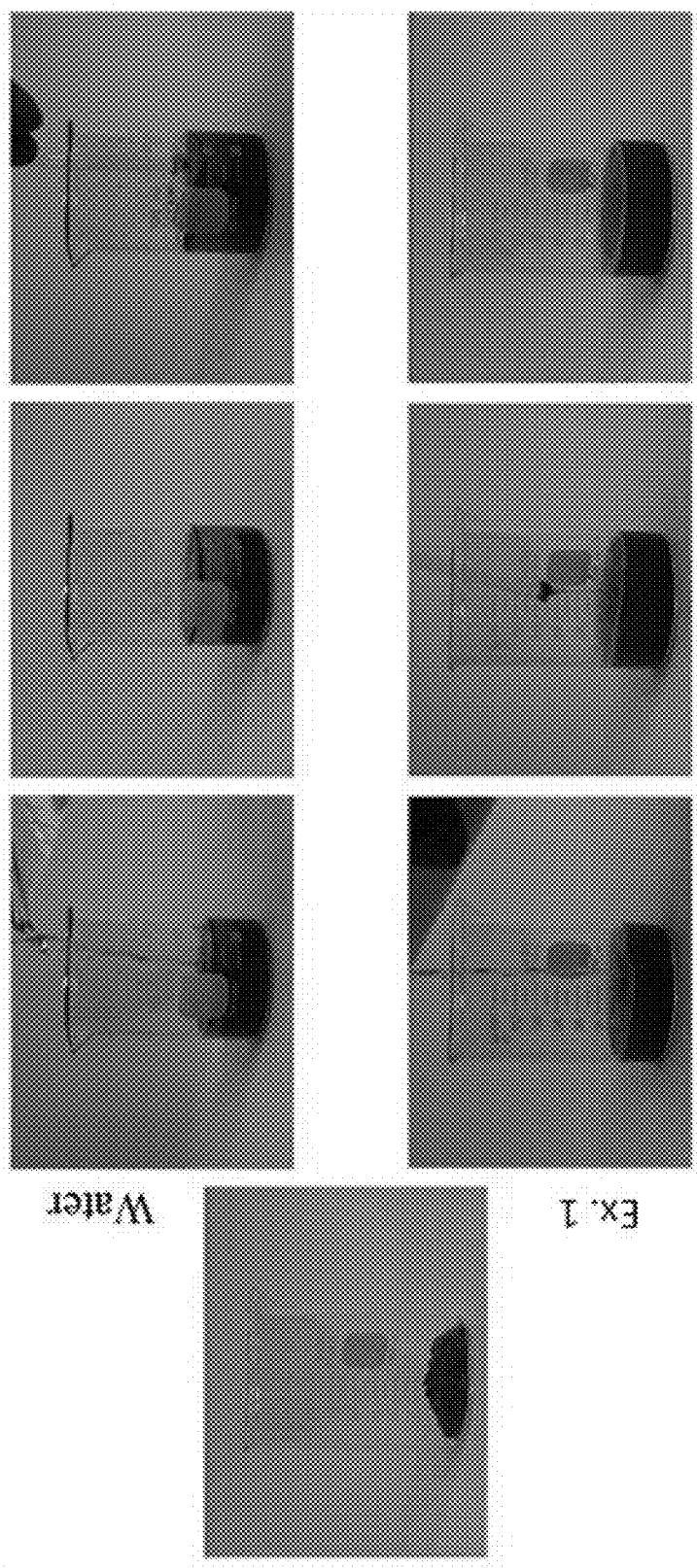
FIG. 22 depicts series of photographs showing the contents of the beakers in Example 19, illustrating showing the effects of adding a solution comprising 5 parts of the composition of Example 1 and 95 parts water by weight to oil-contaminated sludge in a glass beaker with subsequent stirring, and the effect of adding water to oil-contaminated sludge in a glass beaker with subsequent stirring.

FIG. 22 is a series of photographs showing the effects of a solution comprising 5 parts of the composition of Example 1 and 95 parts water by weight versus water on oil-contaminated sludge. The first photograph, on the far left, shows the oil-contaminated sludge in the bottom of a glass beaker before the addition of either water or a Composition of the Invention. The top row of photographs is a time-lapse set of images showing the effects of adding water to oil-contaminated sludge as described. The mechanical effect of pouring water on the oil-contaminated sludge breaks up the sludge slightly, but even with subsequent stirring, the majority of the oil-contaminated sludge remains adhered to the bottom of the beaker and the oil from the oil-contaminated sludge does not disperse in the solution. As shown, stirring with a glass pipette does not disperse the oil in the oil-contaminated sludge.

In contrast, the bottom row of photographs in FIG. 22 illustrates the effect of a solution comprising 5 parts of the composition of Example 1 and 95 parts water by weight on the oil-contaminated sludge. Upon stirring, the solution darkens, and oil is liberated from the oil-contaminated sludge. This experiment illustrates the ability of a Composition of the Invention to remove oil from oil-contaminated sludge.

Example 20

Athabasca oil sand (5 g) was added to a 100 ml glass beaker. 50 ml of an extractant made by admixing the aqueous composition of Example 1 (2.5 g) and water (47.5 g) was added to the Athabasca oil sand at about 23° C. The resultant mixture was stirred for 2 hrs. After stirring and allowing the solids to settle, the mixture was decanted and the extracted oil and sand were separated, then dried and weighed to determine recovery of oil. The supernatant recovered after stirring was reserved. A second sample of Athabasca oil sand and clean stir bar was added to a clean beaker, the reserved supernatant was added to the beaker, and the resultant mixture was stirred at 1000 rpm for 2 hours with a magnetic stir bar. This extraction, recovery, and re-use of the reserved supernatant was repeated for a total of 6 extraction iterations. Table 6, below, reports the percent of oil recovered, where the reserved supernatant is re-used for multiple sequential extractions of separate samples of Athabasca oil sands.

TABLE 6

Recovery of oil when extractant is used iteratively.

|  | Trial 1 | Trial 2 | Trial 3 | Trial 4 | Trial 5 | Trial 6 |
|---|---|---|---|---|---|---|
| wt % of oil recovered | 90% | 89% | 86% | 99% | 93% | 106% |
| Average | 94% | | | | | |
| RSD | 8% | | | | | |

As can be seen from the results presented in Table 6 above, the total recovery of oil from each 5 g sample of Athabasca oil sand does not change within error over successive extractions with the same extractant. This experiment illustrates the ability of a Composition of the Invention to be reused to remove oil from Athabasca oil sands.

Example 21

Figure 23:
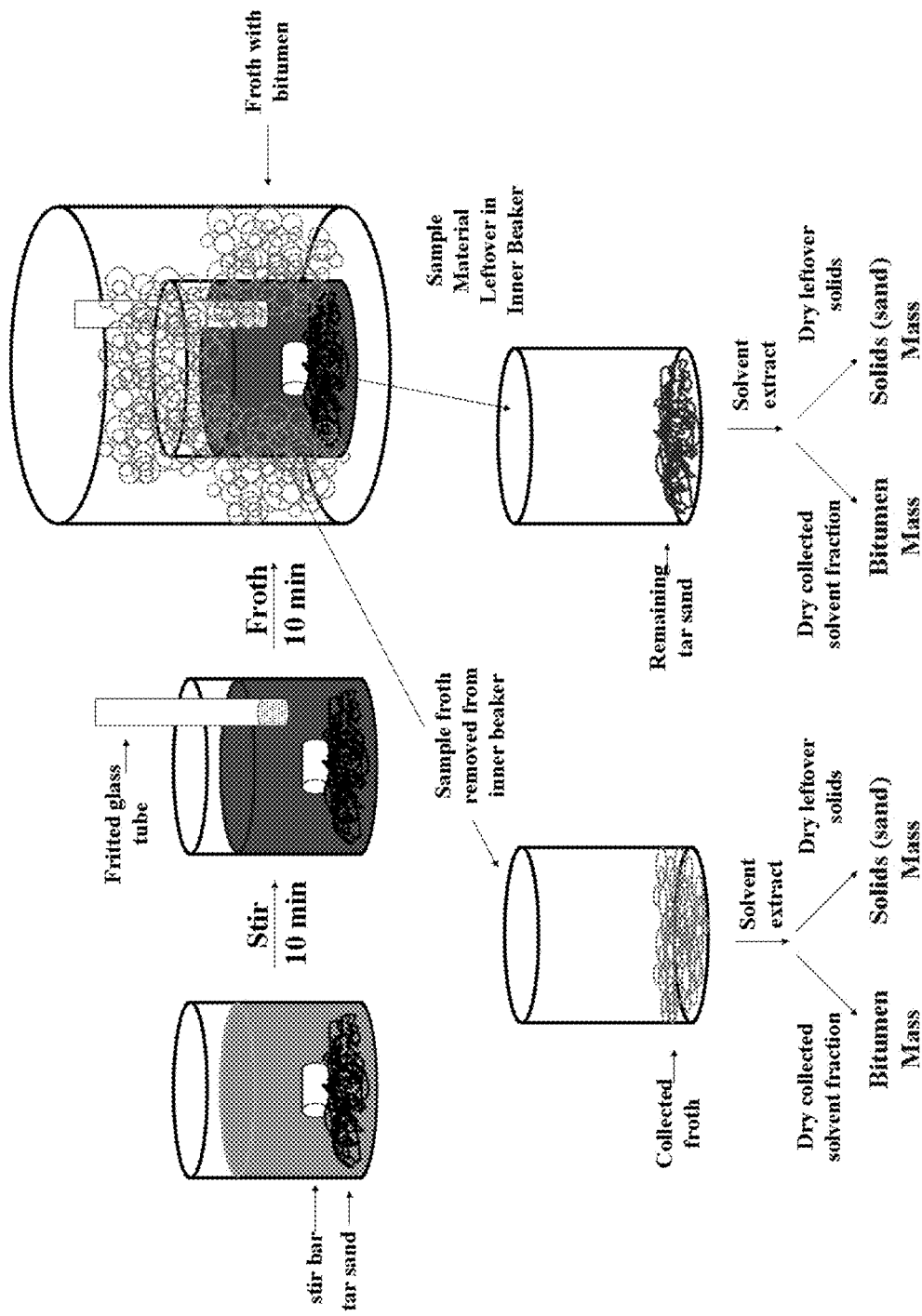
FIG. 23 is a process flow diagram illustrating the process described in Example 21 for frothing and extracting oil from Athabasca oils sand and quantifying recovery of oil therefrom, to quantitatively asses the foaming properties of Compositions of the Invention.

Approximately 5 g of Athabasca oil sand (containing 15 wt % oil), 50 ml of a solution comprising 5 parts of the composition of Example 1 and 95 parts water by weight, and a stir bar were added to a small glass beaker and stirred for 10 minutes. The small beaker was placed inside a larger beaker, and the mixture in the small beaker was aerated by introducing air into the mixture via a fritted glass bubbler at 0.15 L/min for 10 min. The aeration formed an oil-entrained froth which spilled over the sides of the small beaker into the larger beaker. The froth and oil in the larger beaker, and the sand and oil remaining in the small beaker, were each separately collected, dried, and then extracted with a 50/50 (v/v) mixture of toluene and dichloromethane. After removal of the toluene/dichloromethane solvent mixture under vacuum, the percent mass of oil recovered from each of the small and larger beakers was calculated to determine the amount of oil carried from the small beaker to the larger beaker by the froth generated during aeration. FIG. 23 is a process flow diagram illustrating the process employed for frothing and extracting oil from Athabasca oils sands. Forty-three wt % of the oil present in the 5 g of Athabasca oil sand was found to have been transported from the small beaker to the larger beaker by the froth generated during aeration. This amount is significant. Unlike the industrial process described herein, wherein oil sands are treated (e.g., stirred with high pH water and aerated) multiple times to remove oil therefrom, the present 43 wt % recovery was effected in a single aeration step. This example illustrates the ability of a Composition of the Invention to remove oil from Athabasca oil sand using aeration.

Figure 24:
FIG. 24 depicts three photographs illustrating aeration experiments performed as described in Example 21, but without recovery and quantification of oil, to qualitatively asses the foaming properties of illustrative Compositions of the Invention.
Figure 25:
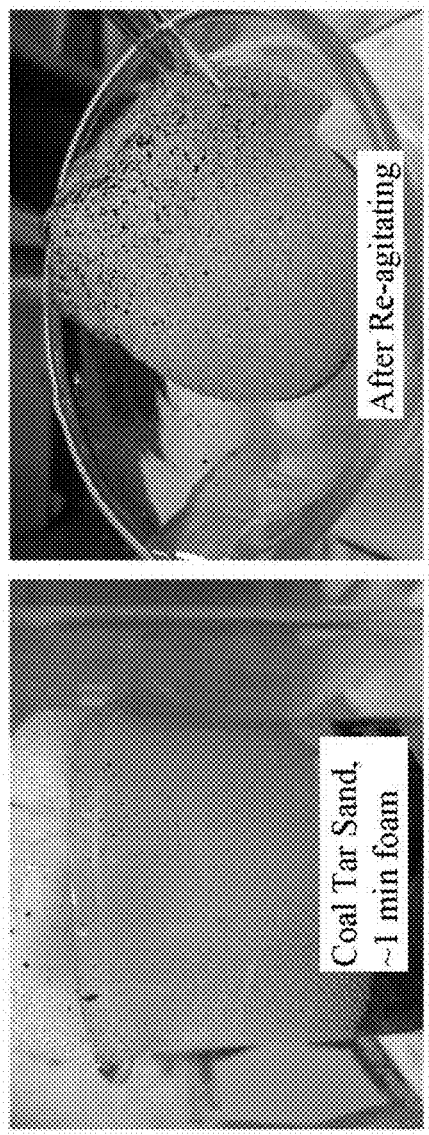
FIG. 25 depicts two photographs illustrating the results of when coal tar coated sand is stirred with a solution comprising 5 parts of the composition of Example 1 and 95 parts water by weight for two hours, then aerated as described in Example 21.

FIG. 24 is a series of photographs from three aeration experiments performed as described above, but without recovery and quantification of oil in the small and larger beakers, to qualitatively assess the frothing properties of the present Compositions of the Invention when aerated. The experiments employed (i) a solution comprising 5 parts of the composition of Example 1 and 95 parts water by weight (labeled "Ex. 1"), (ii) a solution comprising 5 parts of composition 2.2.8 (as described in Example 24 below) and 95 parts water by weight (labeled "2.2.8"), and (iii) a solution comprising 5 parts of composition 8.1 (as described in Example 24 below) and 95 parts water by weight (labeled "8.1"). All three photographs in FIG. 25 show froth with entrained oil being carried out of the small beaker and into the larger beaker. This example illustrates the ability of Compositions of the Invention to remove oil from Athabasca oil sand with aeration.

Example 22

Approximately 5 g of coal tar sand was placed in a glass beaker. 50 ml of an extractant made by admixing the aqueous composition of Example 1 (2.5 g) and water (47.5 g) was added to the beaker at about 23° C. The resultant mixture was stirred for 2 hours, then aerated for 10 minutes as described in Example 21. FIG. 25 is a series of two photographs illustrating the results. Coal tar from the coal tar sand is initially carried out with the froth, but its lower portion contains little or no coal tar (see photograph on the left in FIG. 25). After briefly agitating the sand and coal tar at the bottom of the beaker during aeration of the mixture, additional coal tar was carried out by the froth produced during aeration (see photograph on the right in FIG. 25). This example illustrates the ability of a Composition of the Invention to remove coal tar from coal tar sand with aeration.

Example 23

Figure 26:
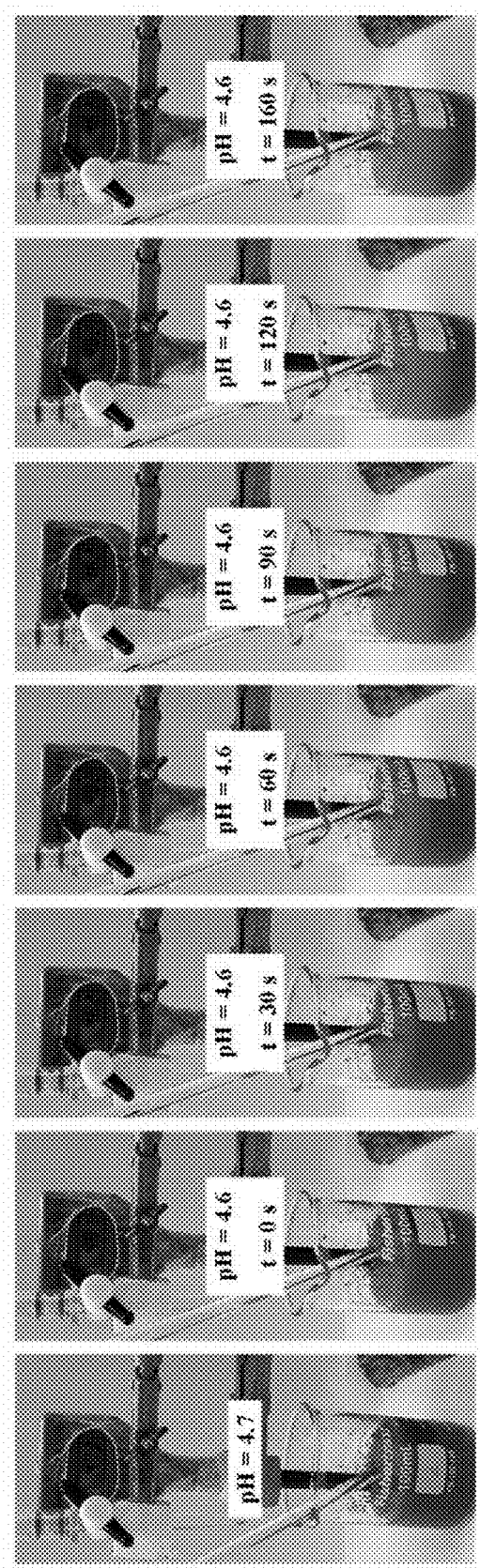
FIG. 26 depicts a series of photographs showing the effect of reducing the pH of a solution comprising 5 parts of the composition of Example 1 and 95 parts water by weight on suspended fines after extraction and removal of extracted oil from a 5 g sample of Athabasca oil sand in the experiment described in Example 23.

FIG. 26 is a series of photographs showing the settling effect on suspended fines by reducing the pH of a solution comprising 5 parts of the composition of Example 1 and 95 parts water by weight, after extraction and removal of extracted oil from a 5 g sample of Athabasca oil sand. Athabasca oil sand (5 g) was added to a 100 ml glass beaker. 50 ml of an extractant made by admixing the aqueous composition of Example 1 (2.5 g) and water (47.5 g) was added to the Athabasca oil sand at about 23° C. The resultant mixture was stirred for 2 hrs. After stirring, the mixture was decanted, extracted oil and sand were removed from the decanted mixture, and the remaining mixture, comprising suspended fines, was placed in a 100 ml glass beaker, was then acidified from pH 13 to pH 4.7. The pH of the mixture was then adjusted to 4.6, and as shown in FIG. 26, the fines in the mixture were precipitated over a 160 second time period. In addition, residual oil in the mixture was observed to rise to the top of the mixture concurrent with the observed precipitation of fines. This example illustrates that acidification of a Composition of the Invention, after extraction and removal of oil from Athabasca oil sand, can effect precipitation of fines.

Example 24

A series of Experiments was performed to evaluate illustrative compositions of the invention prepared using various plant sources, and to assess the effect of various components in Compositions of the Invention. Each composition was prepared by the method described in Experiment 1, then 5 parts by weight of it were admixed with 95 parts by weight of water to provide a solution of the composition to be tested. The contents of each composition are described in Tables 7-18, below. All experiments employed the method for extracting light tar oil as described in Example 17, using the light tar oil described therein.

Experiment Series 1

Experiment series 1 was performed as shown in Table 7, employing corn gluten meal as the plant source.

TABLE 7

Results of Experiment Series 1

| Expt. # | Plant Source (g) | 50% NaOH (g) | $H_2O$ (mL) | NaCl (g) | S-type hydrated lime (g) |
|---|---|---|---|---|---|
| 1.2 | 39.8 | 15.89 | 237.8 | 0.159 | 0 |
| 1.3 | 39.8 | 15.89 | 237.8 | 0 | 1.58 |
| 1.4 | 39.8 | 15.89 | 237.8 | 0.159 | 1.58 |

The compositions of Table 7 successfully released light tar oil from the mass of tar oil adhering to the bottom of the beaker. These experiments illustrate that Compositions of the Invention are effective in removing oil from a substrate.

Experiment Series 2.1

Experiment series 2.1 was performed as shown in Table 8, employing corn gluten meal at the protein source at a reduced concentration relative to the composition of Example 1.

TABLE 8

Results of Experiment Series 2.1

| Expt. # | Plant Source (g) | Citric Acid (g) | 70% isopropanol (mL) | 50% NaOH (g) | $H_2O$ (mL) | NaCl (g) | S-type hydrated lime (g) |
|---|---|---|---|---|---|---|---|
| 2.1.1 | 19.9 | 0.086 | 15.89 | 15.89 | 237.8 | 0.159 | 1.58 |
| 2.1.3 | 19.9 | 0 | 0 | 15.89 | 237.8 | 0.159 | 0 |
| 2.1.4 | 19.9 | 0 | 0 | 15.89 | 237.8 | 0 | 1.58 |
| 2.1.5 | 19.9 | 0 | 0 | 15.89 | 237.8 | 0.159 | 1.58 |
| 2.1.6 | 19.9 | 0.086 | 15.89 | 15.89 | 237.8 | 0 | 0 |
| 2.1.7 | 19.9 | 0.086 | 15.89 | 15.89 | 237.8 | 0 | 1.58 |
| 2.1.8 | 19.9 | 0.086 | 15.89 | 15.89 | 237.8 | 0.159 | 0 |

The compositions of Table 8 successfully released light tar oil from the mass of tar oil adhering to the bottom of the beaker. These experiments illustrate that Compositions of the Invention are effective in removing oil from a substrate.

Experiment Series 2.2

Experiment series 2.2 was performed as shown in Table 9, employing corn gluten meal at the protein source at a reduced concentration relative to the composition of Example 1.

TABLE 9

Results of Experiment Series 2.2

| Expt. # | Plant Source (g) | Citric Acid (g) | 70% isopropanol (mL) | 50% NaOH (g) | $H_2O$ (mL) | NaCl (g) | S-type hydrated lime (g) |
|---|---|---|---|---|---|---|---|
| 2.2.1 | 9.95 | 0.086 | 15.89 | 15.89 | 237.8 | 0.159 | 1.58 |
| 2.2.3 | 9.95 | 0 | 0 | 15.89 | 237.8 | 0.159 | 0 |
| 2.2.4 | 9.95 | 0 | 0 | 15.89 | 237.8 | 0 | 1.58 |
| 2.2.5 | 9.95 | 0 | 0 | 15.89 | 237.8 | 0.159 | 1.58 |
| 2.2.6 | 9.95 | 0.086 | 15.89 | 15.89 | 237.8 | 0 | 0 |
| 2.2.7 | 9.95 | 0.086 | 15.89 | 15.89 | 237.8 | 0 | 1.58 |
| 2.2.8 | 9.95 | 0.086 | 15.89 | 15.89 | 237.8 | 0.159 | 0 |

The compositions of Table 9 successfully released light tar oil from the mass of tar oil adhering to the bottom of the beaker. These experiments illustrate that Compositions of the Invention are effective in removing oil from a substrate.

Experiment Series 2.3

Experiment series 2.3 was performed as shown in Table 10, employing corn gluten meal at the protein source at a reduced concentration relative to the composition of Example 1.

TABLE 10

Results of Experiment Series 2.3

| Expt. # | Plant Source (g) | Citric Acid (g) | 70% isopropanol (mL) | 50% NaOH (g) | $H_2O$ (mL) | NaCl (g) | S-type hydrated lime (g) |
|---|---|---|---|---|---|---|---|
| 2.3.3 | 4.98 | 0 | 0 | 15.89 | 237.8 | 0.159 | 0 |
| 2.3.4 | 4.98 | 0 | 0 | 15.89 | 237.8 | 0 | 1.58 |
| 2.3.8 | 4.98 | 0.086 | 15.89 | 15.89 | 237.8 | 0.159 | 0 |

The compositions of Table 10 successfully released light tar oil from the mass of tar oil adhering to the bottom of the beaker. These experiments illustrate that Compositions of the Invention are effective in removing oil from a substrate.

Experiment Series 4

Experiment series 4 was performed as shown in Table 11, employing corn gluten meal as the plant source with added polysaccharide.

TABLE 11

Results of Experiment Series 4

| Expt. # | Plant Source (g) | Citric Acid (g) | 70% isopropanol (mL) | 50% NaOH (g) | $H_2O$ (mL) | Guar Gum (g) | NaCl (g) | S-type hydrated lime (g) |
|---|---|---|---|---|---|---|---|---|
| 4.1 | 39.8 | 0.086 | 15.89 | 15.89 | 237.8 | 1.978 | 0.159 | 1.58 |
| 4.2 | 39.8 | 0 | 0 | 15.89 | 237.8 | 1.978 | 0 | 0 |
| 4.3 | 39.8 | 0 | 0 | 15.89 | 237.8 | 1.978 | 0.159 | 0 |
| 4.4 | 39.8 | 0 | 0 | 15.89 | 237.8 | 1.978 | 0 | 1.58 |
| 4.5 | 39.8 | 0 | 0 | 15.89 | 237.8 | 1.978 | 0.159 | 1.58 |
| 4.6 | 39.8 | 0.086 | 15.89 | 15.89 | 237.8 | 1.978 | 0 | 0 |
| 4.7 | 39.8 | 0.086 | 15.89 | 15.89 | 237.8 | 1.978 | 0 | 1.58 |
| 4.8 | 39.8 | 0.086 | 15.89 | 15.89 | 237.8 | 1.978 | 0.159 | 0 |

The compositions of Table 11 successfully released light tar oil from the mass of tar oil adhering to the bottom of the beaker. These experiments illustrate that Compositions of the Invention are effective in removing oil from a substrate.

Experiment Series 4b

Experiment series 4b was performed as shown in Table 12, employing cotton seed meal as the plant source with added polysaccharide.

TABLE 12

Results of Experiment Series 4b

| Expt. # | Plant Source (g) | Citric Acid (g) | 70% isopropanol (mL) | 50% NaOH (g) | $H_2O$ (mL) | Guar Gum (g) | NaCl (g) | S-type hydrated lime (g) |
|---|---|---|---|---|---|---|---|---|
| 4b.1 | 19.9 | 0.086 | 15.89 | 15.89 | 237.8 | 1.978 | 0.159 | 1.58 |
| 4b.2 | 19.9 | 0 | 0 | 15.89 | 237.8 | 1.978 | 0 | 0 |
| 4b.3 | 19.9 | 0 | 0 | 15.89 | 237.8 | 1.978 | 0.159 | 0 |
| 4b.4 | 19.9 | 0 | 0 | 15.89 | 237.8 | 1.978 | 0 | 1.58 |
| 4b.5 | 19.9 | 0 | 0 | 15.89 | 237.8 | 1.978 | 0.159 | 1.58 |
| 4b.6 | 19.9 | 0 | 0 | 15.89 | 237.8 | 1.978 | 0 | 0 |
| 4b.8 | 19.9 | 0 | 0 | 15.89 | 237.8 | 1.978 | 0.159 | 0 |

The compositions of Table 12 successfully released light tar oil from the mass of tar oil adhering to the bottom of the beaker. These experiments illustrate that Compositions of the Invention are effective in removing oil from a substrate.

Experiment Series 6

Experiment series 6 was performed as shown in Table 13, employing wheat germ as the plant source.

TABLE 13

Results of Experiment Series 6

| Expt. # | Plant Source (g) | Citric Acid (g) | 70% isopropanol (mL) | 50% NaOH (g) | $H_2O$ (mL) | Guar Gum (g) | NaCl (g) | S-type hydrated lime (g) |
|---|---|---|---|---|---|---|---|---|
| 6.1 | 39.8 | 0.086 | 15.89 | 15.89 | 237.8 | 1.978 | 0.159 | 1.58 |

The compositions of Table 13 successfully released light tar oil from the mass of tar oil adhering to the bottom of the beaker. These experiments illustrate that Compositions of the Invention are effective in removing oil from a substrate.

Experiment Series 7

Experiment series 7 was performed as shown in Table 14, employing flax seed as the plant source.

TABLE 14

Results of Experiment Series 7

| Expt. # | Plant Source (g) | Citric Acid (g) | 70% isopropanol (mL) | 50% NaOH (g) | $H_2O$ (mL) | Guar Gum (g) | NaCl (g) | S-type hydrated lime (g) |
|---|---|---|---|---|---|---|---|---|
| 7.1 | 19.9 | 0.086 | 15.89 | 15.89 | 237.8 | 1.978 | 0.159 | 1.58 |

The compositions of Table 14 successfully released light tar oil from the mass of tar oil adhering to the bottom of the beaker. These experiments illustrate that Compositions of the Invention are effective in removing oil from a substrate.

Experiment Series 8

Experiment series 8 was performed as shown in Table 15, employing cotton seed meal in varying amounts as the plant source.

TABLE 15

Results of Experiment Series 8

| Expt. # | Plant Source (g) | Citric Acid (g) | 70% isopropanol (mL) | 50% NaOH (g) | $H_2O$ (mL) | NaCl (g) | S-type hydrated lime (g) |
|---|---|---|---|---|---|---|---|
| 8.1 | 19.9 | 0.086 | 15.89 | 15.89 | 237.8 | 0.159 | 0 |
| 8.2 | 9.95 | 0.086 | 15.89 | 15.89 | 237.8 | 0.159 | 0 |
| 8.3 | 4.975 | 0.086 | 15.89 | 15.89 | 237.8 | 0.159 | 0 |
| 8.4 | 19.9 | 0.086 | 15.89 | 15.89 | 237.8 | 0.159 | 1.58 |
| 8.5 | 9.95 | 0.086 | 15.89 | 15.89 | 237.8 | 0.159 | 1.58 |
| 8.6 | 4.975 | 0.086 | 15.89 | 15.89 | 237.8 | 0.159 | 1.58 |

The compositions of Table 15 successfully released light tar oil from the mass of tar oil adhering to the bottom of the beaker. These experiments illustrate that Compositions of the Invention are effective in removing oil from a substrate.

Experiment Series 10.2

Experiment series 10.2 was performed as shown in Table 16, employing corn gluten meal as the plant source, various concentration of base (sodium hydroxide), and corn gluten meal is either soaked in water for 12 hours prior to use (Expts. 10.2.1-10.2.3) or the used dry (Expts. 10.2.4-10.2.6).

TABLE 16

Results of Experiment Series 10.2

| Expt. # | Plant Source (g) | 50% NaOH (g) | $H_2O$ (mL) | NaCl (g) |
|---|---|---|---|---|
| 10.2.1 | 19.9 | 15.89 | 253.69 | 0.159 |
| 10.2.2 | 19.9 | 30 | 253.69 | 0.159 |
| 10.2.3 | 19.9 | 45 | 253.69 | 0.159 |
| 10.2.4 | 19.9 | 15.89 | 253.69 | 0.159 |
| 10.2.5 | 19.9 | 30 | 253.69 | 0.159 |
| 10.2.6 | 19.9 | 45 | 253.69 | 0.159 |

The compositions of Table 16 successfully released light tar oil from the mass of tar oil adhering to the bottom of the beaker. These experiments illustrate that Compositions of the Invention are effective in removing oil from a substrate.

Experiment Series 12.2

Experiment series 12.2 was performed as shown in Table 17, employing wheat germ as the plant source, various concentration of base (sodium hydroxide), and the wheat germ is either soaked in water for 12 hours prior to use (Expts. 12.2.1-12.2.3) or used dry (Expts. 12.2.4-12.2.6).

TABLE 17

Results of Experiment Series 12.2

| Expt. # | Plant Source (g) | 50% NaOH (g) | H2O (mL) | NaCl (g) |
|---|---|---|---|---|
| 12.2.1 | 19.9 | 15.89 | 253.69 | 0.159 |
| 12.2.2 | 19.9 | 30 | 253.69 | 0.159 |
| 12.2.3 | 19.9 | 45 | 253.69 | 0.159 |
| 12.2.4 | 19.9 | 15.89 | 253.69 | 0.159 |
| 12.2.5 | 19.9 | 30 | 253.69 | 0.159 |
| 12.2.6 | 19.9 | 45 | 253.69 | 0.159 |

The compositions of Table 17 successfully released light tar oil from the mass of tar oil adhering to the bottom of the beaker. These experiments illustrate that Compositions of the Invention are effective in removing oil from a substrate.

Experiment Series 13.2

Experiment series 13.2 was performed as shown in Table 18, employing flax seed meal as the plant source, various concentration of base (sodium hydroxide), and the flax seed is either soaked in water for 12 hours prior to use (Expts. 13.2.1-13.2.3) or used dry (Expts. 13.2.4-13.2.6).

TABLE 18

Results of Experiment Series 13.2

| Expt. # | Plant Source (g) | 50% NaOH (g) | H2O (mL) | NaCl (g) |
|---|---|---|---|---|
| 13.2.1 | 19.9 | 15.89 | 253.69 | 0.159 |
| 13.2.2 | 19.9 | 30 | 253.69 | 0.159 |
| 13.2.3 | 19.9 | 45 | 253.69 | 0.159 |
| 13.2.4 | 19.9 | 15.89 | 253.69 | 0.159 |
| 13.2.5 | 19.9 | 30 | 253.69 | 0.159 |
| 13.2.6 | 19.9 | 45 | 253.69 | 0.159 |

The compositions of Table 18 successfully released light tar oil from the mass of tar oil adhering to the bottom of the beaker. These experiments illustrate that Compositions of the Invention are effective in removing oil from a substrate.

Example 25

Compositions 10.2.1 and 12.2.6 as described in Example 24, above, were lyophilized, either before centrifugation, or after centrifugation to remove solids and gel formed during preparation. In addition, the Composition of Example 2 was lyophilized after its preparation by the method below.

Lyophilization was performed by placing each composition in a 50 mL loosely covered plastic vial, immersing the vial in liquid nitrogen for 30 min, then placing the vial in a bench-top manifold freeze dryer and applying vacuum (approximately $10^{-2}$ torr) for 48 hours. The compositions were weighed before and after lyophilization. The amount of liquid removed was determined by the difference between the initial mass of the composition prior to lyophilization and its mass after lyophilization. The results are reported in Table 19, below.

TABLE 19

Mass of Solids Recovered and Liquid Removed in Centrifugation of Exemplary Compositions of the Invention

| Expt. # | Mass of Solids (g) | Mass of Liquid Removed (g) |
|---|---|---|
| 10.2.1 - Centrifuged | 2.704 | 20.921 |
| 10.2.1 - Non-centrifuged | 2.723 | 21.307 |
| 12.2.6 - Centrifuged | 2.723 | 11.395 |

TABLE 19-continued

Mass of Solids Recovered and Liquid Removed in Centrifugation of Exemplary Compositions of the Invention

| Expt. # | Mass of Solids (g) | Mass of Liquid Removed (g) |
|---|---|---|
| 12.2.6 - Non-centrifuged | 5.497 | 21.647 |
| Example 2 - Centrifuged | 3.492 | 21.139 |

The recovered solids from each composition were reconstituted with water. Reconstitution was performed in each of two ways: 1) adding water to provide a solution having a concentration equal to 5 parts of the composition prior to lyophilization and 95 parts water; and 2) by reconstituting the solids to provide a mixture having the same mass as the composition prior to lyophilization, then admixing 5 parts of the reconstituted mixture and 95 parts water. No observable differences were observed in preparing the compositions using the two reconstitution methods.

The efficacy of the reconstituted materials for extraction of light tar oil, extraction of coal tar, and frothing and extraction of Athabasca sand was assessed using methods described herein. The compositions were observed to perform essentially the same as comparable, non-lyophilized, non-reconstituted counterparts in each experiment.

These experiments illustrate that lyophilized and reconstituted Compositions of the Invention are effective for removing oil from a substrate, for extracting coal tar from coal tar sands, and for removing oil from Athabasca oil sand using frothing.

Example 26

An illustrative aqueous Composition of the Invention comprising plant material, but not comprising polysaccharide other than that present in or derived from the plant material, was prepared as follows. Citric acid (0.086 grams) was dissolved in 15.89 ml of 70% isopropanol at about 23° C. Zein (26.5 g) was added, and the resultant mixture was allowed to stir for 2 hours. 15.89 g of a 50% aqueous sodium hydroxide solution was added to 237.8 g of water, the resultant diluted sodium hydroxide solution was added to the isopropanol/zein mixture, and the resultant mixture was allowed to stand for 6 hours. Sodium chloride (0.159 g) was then added, also with stirring. The resultant mixture was then allowed to stand for an additional 2 hours. S-type hydrated lime (1.58 g) was then added with stirring, and the resultant mixture was stirred until uniform. The solids were allowed to settle, and the supernatant was decanted to provide the illustrative aqueous composition as the decanted supernatant.

In a glass vessel, (2.5 g) of the aqueous composition prepared as described in the immediately preceding paragraph was combined with water (47.5 g) to provide an extractant. Coal tar sand (5 g, 15 wt % coal tar) from a North Carolina gasification plant site was added to the extractant. The resultant mixture was stirred using a magnetic stir bar for 90 minutes at about 23° C. Extraction of the coal tar from the coal tar sand was observed.

This example demonstrates that an illustrative Composition of the Invention is useful for extracting coal tar from coal tar sand.

Example 27

A comparative composition comprising a polysaccharide, but not comprising plant material, was prepared as follows. Guar gum (1.978 g), citric acid (0.086 g), 15.89 ml of 70% isopropanol, sodium chloride (0.159 g), S-type hydrated lime (1.58 g) and 15.89 g of a 50% aqueous sodium hydroxide solution were added to 237.8 g of water at about 23° C. The resultant mixture was stirred until uniform.

In a glass vessel, (2.5 g) of the comparative composition prepared as described in the immediately preceding paragraph was combined with water (47.5 g) to provide a test extractant. Coal tar sand (5 g, 15 wt % coal tar) from a North Carolina gasification plant site was added to the test extractant. The resultant mixture was stirred using a magnetic stir bar for 90 minutes at about 23° C. No extraction of the coal tar from the coal tar sand was observed.

Example 28

The weight percentage of protein, fat, fiber and carbohydrate was determined for Compositions of the Invention comprising soybean or hulled hemp seeds as the plant protein. The protein, fat, fiber and carbohydrate content of soybean and hulled hemp seeds is described in Table 20, below.

TABLE 20

Composition of soybean and hulled hemp seed.

| | Soybean | Hulled Hemp Seeds |
|---|---|---|
| Protein | 36.5% | 33.3% |
| Fat | 19.9% | 46.7% |
| Fiber | 9.3% | 6.7% |
| Carbohydrate | 30.2% | 20.0% |

Example 29

An illustrative aqueous composition of the invention comprising hemp, but not comprising polysaccharide other than that present in or derived from the plant material, was prepared employing $HNO_3$ instead of NaOH:

Citric acid (0.14 grams) was dissolved in 22.8 mL of 70% isopropanol at about 23° C. Hulled hemp seed (56.838 g) was added, and the resultant mixture was stirred until homogenous, then allowed to stand for 2 hours. The resultant mixture was added to 284 mL of 2.0 M $HNO_3$, and stirred 12 hours. Guar gum (2.84 g) and sodium chloride (0.23 g) wetted with 70% isopropanol was then added to hemp mixture with stirring, then allowed to stand an additional 3 hours. Calcium hydroxide (2.27 g) in 20 mL of distilled water was then added, and the resultant mixture was stirred until uniform then allowed to stand for 12 hours. The solids were filtered from the solution using a paint filter. The pH of the filtrate was then adjusted to pH 12.7 by adding 50 wt % sodium hydroxide solution with stirring. The pH 12.7 filtrate was then centrifuged for 20 minutes at 1,150 G. FIG. 27 is a photograph showing an aliquot of a pH 12.7 hemp-based composition, prepared by acid treatment of hemp seed, after centrifugation. As shown in FIG. 27, the solution forms three layers after centrifugation; the middle layer comprises protein from the hemp seed.

An aliquot of the centrifuged filtrate (3 mL) was then admixed with water (27 mL) to provide a 10 wt % solution of centrifuged hemp-based composition, which had a pH of 12.7. 2 g of a mixture of #2 and #4 Monarch oil was added to the solution. FIG. 28A is a picture showing the mixture of #2 and #4 Monarch oil after addition to a 10 wt % solution of the uncentrifuged hemp-based composition. As can be seen in FIG. 28A, the 10 wt % solution of the uncentrifuged hemp-based composition produces stringers of Monarch oil.

An aliquot of the uncentrifuged filtrate (3 mL) was also admixed with water (27 mL) to provide a 10 wt % solution of uncentrifuged hemp-based composition, which had a pH of 12.7. 2 g of coal tar was added to the solution. FIG. 28B is a picture showing coal tar after addition to a 10 wt % solution of the centrifuged hemp-based composition. As shown in FIG. 28B, the 10 wt % solution of the centrifuged hemp-based composition produced stringers of coal tar. This Example demonstrates that compositions of the invention produced by acid treatment of a plant material are useful in extracting hydrocarbon-containing oil or coal tar from a substrate.

Example 30

The sprouting process of a grain changes its protein and carbohydrate profiles as the proteins (enzymes) are used to process the carbohydrates (starches) into energy for the plant to grow. Malting a grain is the process by which a grain is steeped in water and aerated to begin the sprouting process, then heated to stop the starch conversion at a certain point. Sprouting of soybeans prior to their use in the preparation of illustrative Compositions of the Invention was conducted by rinsing soybeans with water 5 times, then placing the soybeans on damp paper towels covered with a layer of damp paper towels, then covering the damp paper towels with aluminum foil to prevent evaporation. The damp beans were placed in the dark for about 2 days until sprouts appeared.

An illustrative Composition of the Invention, prepared as described in Example 1, but substituting sprouted soybean for corn gluten meal, was prepared (the "soybean sprout-based composition"). A 10 wt % solution of the soybean sprout-based composition was prepared by combining 2 g of the soybean sprout-based composition with 18 g of water. 2 g of a mixture of #2 and #4 Monarch oil was added to the 10 wt % solution with stirring. The #2 and #4 Monarch oil was emulsified by the 10 wt % soybean sprout-based solution.

A second 10 wt % solution of the soybean sprout-based composition was prepared by combining 5 g of the soybean sprout-based composition with 45 g of water. 5 g of a coal tar coated sand, comprising about 10:1 sand to tar by mass, was added to the solution with stirring. After three hours of stirring, the coal tar was separated from the sand and formed balls in the second 10 wt % soybean sprout-based solution.

A third 10 wt % solution of the soybean sprout-based composition was prepared by combining 5 g of the soybean sprout-based composition with 45 g of water. 5 g of a coal tar coated sand, comprising about 10:1 sand to tar by mass, was added to the solution with stirring. After three hours of stirring, the coal tar was separated from the sand and formed balls in the third 10 wt % soybean sprout-based solution.

Example 31

Biodiesel was prepared by combining 90 g of vegetable oil with 19.2 g of methanol (with 1% by mass KOH dissolved in the methanol prior to mixing with the vegetable oil) to vegetable oil. Biodiesel is made by the catalytic trans-esterification of triglycerides (fats) which make up vegetable oils using methanol with a catalytic amount of hydroxide, as shown in Scheme 1, below.

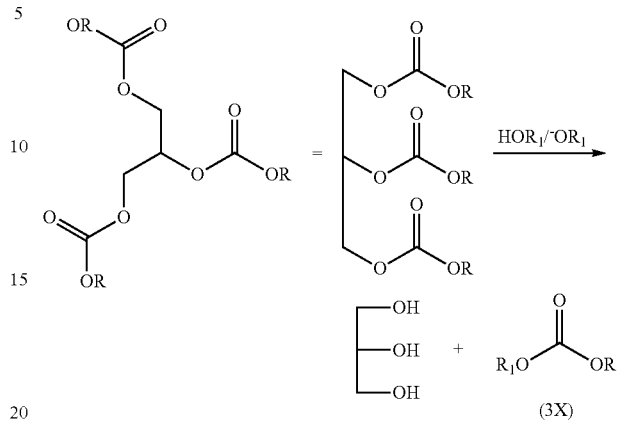

Scheme 1. Illustrative transesterification of triglycerides with methanol (HOR$_1$) with catalytic OH$^-$ to make biodiesel.

Biodiesel prepared as described above surpassed the efficacy of petroleum diesel in dissolving the #6 oil, i.e., it was the better solvent. The aqueous composition of Example 1 (1 g) was combined with water (19 g) to provide an extractant. When the extractant was combined in a 1:1 ratio with biodiesel prepared as described above, an emulsion was formed, unlike the phase separation observed when the extractant was combined with petroleum-based diesel in ratios ranging from 1:10 to 10:1 diesel to extractant.

Example 32

3.204 g of methanol was combined with 90 g of vegetable oil and stirred overnight to provide a partially trans-esterified glycerides (PTEG) mixture comprising triglycerides, diglycerides, monoglycerides, and fatty acid methyl esters (FAMEs). 2 g of the PTEG solution was combined with 2 g of #6 oil, and the PTEG was observed to be miscible with the #6 oil. However, when 10 mL of the PTEG solution was combined with 10 mL a solution comprising 2.5 g of the composition of Example 1 in 47.5 g of water, the resultant mixture formed an emulsion which persisted for about 1 hour.

Example 33

To examine the emulsifying characteristics of a mixture of PTEG and an illustrative composition of the invention, 1 mL of the PTEG solution was combined with 10 mL of a solution comprising 2.5 g of the composition of Example 35 in 47.5 g of water and 1 mL of d-limonene. A solvent-in water emulsion was formed and was visually observed to persist for 1 hour, significantly longer than the emulsion observed when 1 mL of the PTEG solution was combined with 10 mL a solution comprising 2.5 g of the composition of Example 1 in 47.5 g of water.

Example 34

6 Fuel oil contains approximately 25% asphaltenes. Because coal tar does not float in a solution comprising 3 g of the Composition of Example 35 and 27 g of water, a de-asphaltened coal tar sample was tested. The de-asphaltened coal tar was prepared by placing approximately 50 g of neat coal tar in a 4 L glass bottle. Pentane was added to cover the coal tar layer and a stir bar used to stir the pentane. The pentane was removed every two days and set aside, fresh pentane was replaced in the bottle. This procedure was repeated seven times. The pentane, containing de-asphaltened coal tar, was evaporated under a gentle flow of air overnight to obtain pure de-asphaltened coal tar. A few drops of the de-asphaltened coal tar was added to a solution comprising 2.5 g of the composition of Example 1 in 47.5 g of water, and did not float.

Figure 29:
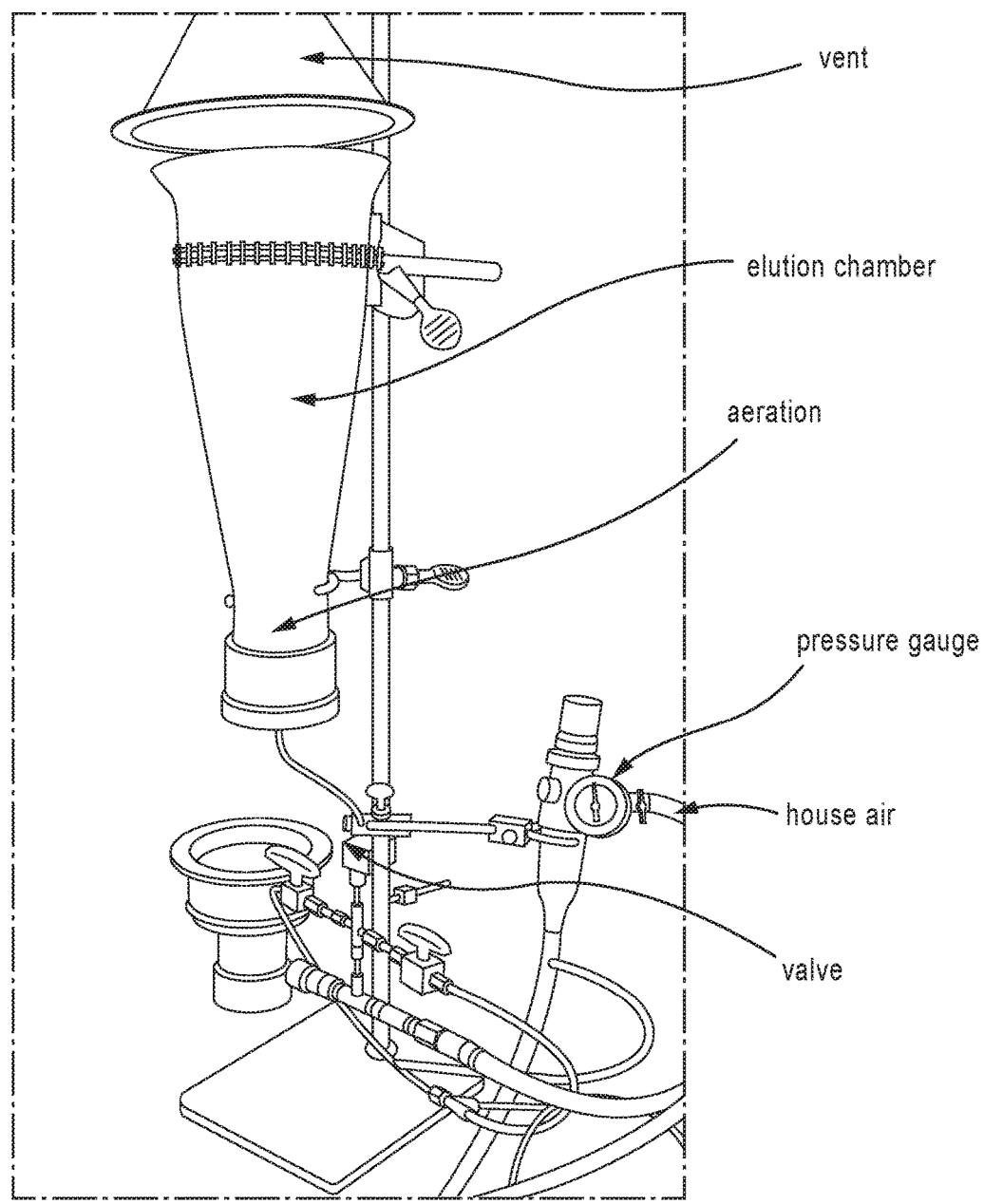
FIG. 29 is a line drawing of an illustrative frothing apparatus.

To liberate coal tar or oil from Athabasca oil sand, experiments including stirring a sample with a stirbar and frothing the solution by aerating the solution with compressed air have been performed (see, e.g., Examples 21 and 22). As when stirring a mixture of a composition of the invention and Athabasca oil sand, frothing can produce coagulated mass of tar-enriched sand. FIG. 29 is a photograph of an illustrative frothing apparatus. The elution chamber is configured to receive a sample of material from which a hydrocarbon-containing substance (e.g., oil, coal tar) is to be extracted. Air can be introduced into the apparatus from the bottom of the chamber.

Figure 30:
FIG. 30 is a photograph showing shows a sample comprising homogenized 5 wt % coal tar/95 wt % sand, in the bottom of the frothing apparatus of FIG. 29.
Figure 31:
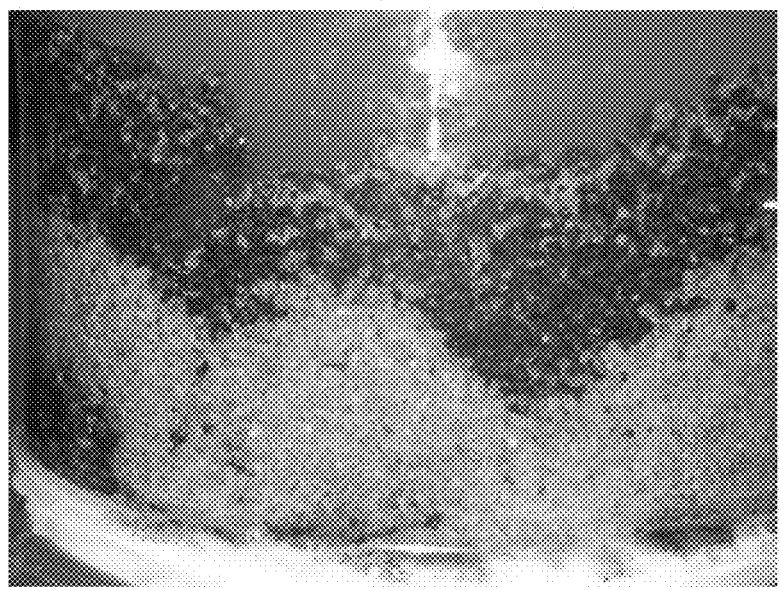
FIG. 31 is a photograph showing a sample comprising homogenized 5 wt % coal tar/95 wt % sand, in the bottom of the frothing apparatus of FIG. 29 after three hours of aeration with air at 60 psi.

FIG. 30 is a photograph showing shows a sample comprising homogenized 5 wt % coal tar/95 wt % sand, in the bottom of the frothing apparatus of FIG. 29, before frothing. As shown in FIG. 31, the coal tar (black) is dispersed relatively uniformly throughout the sand. 500 mL of a solution comprising 50 g of the composition of Example 35 and 450 g of water was placed in the apparatus of FIG. 29. After three hours of aeration, with air flow at approximately 60 psi through the coal tar/sand mixture, the tar is stripped from the sand, becoming suspended in the liquid. FIG. 31 is a photograph showing a sample comprising homogenized 5 wt % coal tar/95 wt % sand, in the bottom of the frothing apparatus of FIG. 29 after three hours of aeration with air at 60 psi. As shown in FIG. 31, coal tar is concentrated at the top of the sand, with clean sand below it.

A 10 wt % solution of the composition of Example 35 was prepared by combining 50 g of the soybean sprout-based composition with 450 g of water. The solution was placed into the aeration apparatus of FIG. 29. 5 g of a coal tar coated sand, comprising about 10:1 sand to tar by mass, was added to the solution, and the mixture was aerated. Time series experiments were performed, observing the aeration at half-hour intervals. After 30 min of aeration, most of the sand in sections where aeration was optimum was clean. However, after 3 hrs there were pockets of coal tar due to poor aeration.

Example 35

An illustrative aqueous composition of the invention comprising plant material, but not comprising polysaccharide other than that present in or derived from the plant material, was prepared as follows. Citric acid (1.07 grams) was dissolved in 0.156 kg of 70% isopropanol at about 23° C. Hulled hemp seed (0.497 kg) was added, and the resultant mixture was allowed to stir for 2 hours, then allowed to stand for 2 hours. 0.620 kg of granular sodium hydroxide was added to 2.966 kg of water, the resultant sodium hydroxide solution was added to the isopropanol/hemp mixture, and the resultant mixture was allowed to stand for 6 hours. Sodium chloride (1.98 g) was then added, also with stirring. The resultant mixture was then allowed to stand an additional 2 hours. S-type hydrated lime (19.8 g) was then added with stirring, and the resultant mixture was stirred until uniform. The solids were allowed to settle for 80 hours, and the supernatant was decanted to provide the illustrative aqueous composition as the decanted supernatant.

Example 36

An illustrative aqueous composition of the invention comprising plant material, but not comprising polysaccharide other than that present in or derived from the plant material, was prepared as follows. Citric acid (1.07 grams) was dissolved in 0.156 kg of 70% isopropanol at about 23° C. Hulled hemp seed (0.497 kg) was added, and the resultant mixture was allowed to stir for 2 hours, then allowed to stand for 2 hours. 0.620 kg of granular sodium hydroxide was added to 2.966 kg of water, the resultant sodium hydroxide solution was added to the isopropanol/hemp mixture, and the resultant mixture was allowed to stand for 6 hours. Guar gum (24.8 g) wetted with 70% isopropanol was then added to the isopropanol/hemp mixture with stirring. Sodium chloride (1.98 g) was then added, also with stirring. The resultant mixture was then allowed to stand an additional 2 hours. S-type hydrated lime (19.8 g) was then added with stirring, and the resultant mixture was stirred until uniform. The solids were allowed to settle for 80 hours, and the supernatant was decanted to provide the illustrative aqueous composition as the decanted supernatant.

Example 37

An illustrative aqueous Composition of the Invention comprising plant material, but not comprising polysaccharide other than that present in or derived from the plant material, was prepared as follows. Citric acid (1.07 grams) was dissolved in 0.156 kg of 70% isopropanol at about 23° C. Hulled hemp seed (0.497 kg) was added, and the resultant mixture was allowed to stir for 2 hours, then allowed to stand for 2 hours. 0.620 kg of granular sodium hydroxide was added to 2.966 kg of water, the resultant sodium hydroxide solution was added to the isopropanol/hemp mixture, and the resultant mixture was allowed to stand for 6 hours. Sodium chloride (1.98 g) was then added, also with stirring. The resultant mixture was then allowed to stand an additional 2 hours. S-type hydrated lime (19.8 g) was then added with stirring, and the resultant mixture was stirred until uniform. The solids were allowed to settle for 104 hours, and the supernatant was decanted to provide the illustrative aqueous composition as the decanted supernatant.

Example 38

An illustrative aqueous Composition of the Invention was prepared as follows. Citric acid (1.07 grams) was dissolved in 0.156 kg of 70% isopropanol at about 23° C. Hulled hemp seed (0.497 kg) was added, and the resultant mixture was allowed to stir for 2 hours, then allowed to stand for 2 hours. 0.620 kg of granular sodium hydroxide was added to 2.966 kg of water, the resultant sodium hydroxide solution was added to the isopropanol/hemp mixture, and the resultant mixture was allowed to stand for 6 hours. Guar gum (24.8 g) wetted with 70% isopropanol was then added to the isopropanol/hemp mixture with stirring. Sodium chloride (1.98 g) was then added, also with stirring. The resultant mixture was then allowed to stand an additional 2 hours. S-type hydrated lime (19.8 g) was then added with stirring, and the resultant mixture was stirred until uniform. The solids were allowed to settle for 104 hours, and the supernatant was decanted to provide the illustrative aqueous composition as the decanted supernatant.

Example 39

Figure 32A:
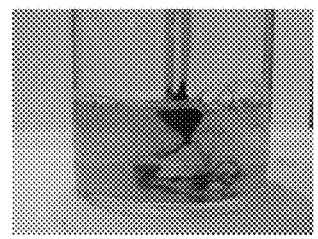
FIGS. 32A-D are photographs showing emulsification and frothing of coal tar in a composition of the invention.
Figure 32B:
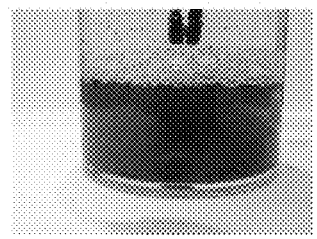
Figure 32C:
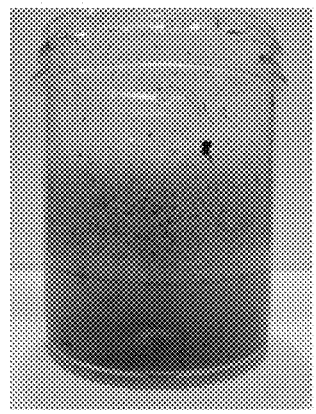
Figure 32D:
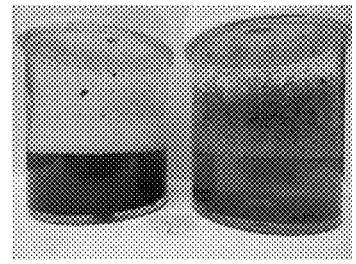

A 10 wt % solution of the composition of Example 37 was prepared by admixing 3 g of the composition of Example 37 and 27 g of water. The solution pH was 13.1. The solution was placed in a glass beaker, and 0.37 g of coal tar was added to the solution with a glass rod. FIG. 32A is a photograph showing the addition of coal tar oil to a 10 wt % solution of the composition of Example 37. As shown in FIG. 30A, initially stringers are formed upon introduction of the coal tar oil to the solution. FIG. 32B is a photograph showing the emulsification of coal tar oil in a 10 wt % solution of the composition of Example 37 upon stirring for about 10 seconds. After shaking the mixture vigorously, a foam is formed and the coal tar was carried into the foam where it remained until the foam subsided after approximately 8 hours. FIG. 32C is a photograph showing the foam that was formed after shaking the mixture. FIG. 30D is a picture showing the difference in foaming performance between 30 mL a 5 wt % solution of the composition of Example 37 (left beaker) and 30 mL a 10 wt % solution of the composition of Example 37 (right beaker), each comprising 0.37 g of coal tar oil, after 15 minutes of vigorous shaking.

As shown in FIG. 30D, there is a distinct difference between the layers formed in each beaker. In the beaker comprising the 5 wt % solution of Example 37, the coal tar is still in solution, whereas in the beaker comprising the 10 wt % solution of Example 37, the majority of the coal tar is carried in the foam.

After agitating the beaker comprising the 10 wt % solution of Example 37 with a glass rod by striking the outside of the beaker, coal tar balls fell out of the froth and to the bottom of the liquid in the beaker, then rose to top of liquid in the beaker. Without frothing, coal tar sinks to the bottom of the liquid in the beaker after stirring.

Example 40

5 wt %, 10 wt % and 20 wt % Solutions of the composition of Example 37 were prepared by admixing 1.5 g, 3 g and 6 g of the composition of Example 37 with 28.5 g, 27 g and 24 g of water, respectively. The pH of each of the solutions was 13.1. Each solution was placed in a glass beaker, and 0.37 g of #6 fuel oil was added to each solution.

Figures 33A, 33B, 33C:
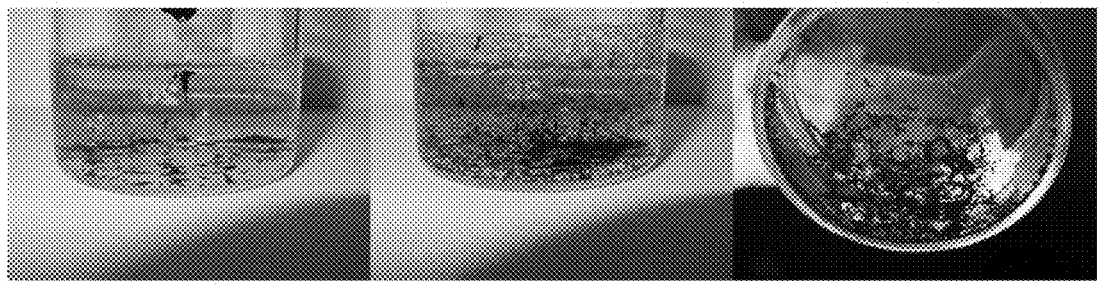
FIGS. 33A-C are photographs showing the dissolution behavior of #6 fuel oil in a 5 wt % solution of the composition of Example 35.

FIGS. 33A-C are photographs showing the dissolution behavior of #6 fuel oil in a 5 wt % solution of the composition of Example 37. As shown in FIG. 33A, on initial stirring, the #6 fuel oil did not significant disperse. As shown in FIG. 33B, after aggressive stirring for about 10 seconds, the #6 fuel oil formed small stringers in solution. FIG. 33C is a picture of the bottom of the beaker containing the 5 wt % solution of Example 37 and the #6 fuel oil after aggressive stirring. As can be seen, small stringers of the #6 fuel oil are formed.

Figures 34A, 34B, 34C:
FIGS. 34A-C are photographs showing the dissolution behavior of #6 fuel oil in a 10 wt % solution of the composition of Example 35.

FIGS. 34A-C are photographs showing the dissolution behavior of #6 fuel oil in a 10 wt % solution of the composition of Example 37. As shown in FIG. 34A, on initial stirring, small stringers of the #6 fuel oil are formed. As shown in FIG. 34B, after aggressive stirring for about 10 seconds, the #6 fuel oil formed small stringers in solution. FIG. 34C is a picture of the bottom of the beaker containing the 10 wt % solution of Example 37 and the #6 fuel oil after aggressive stirring. As can be seen, stringers of the #6 fuel oil are formed.

Figures 35A, 35B, 35C:
FIGS. 35A-C are photographs showing the dissolution behavior of #6 fuel oil in a 20 wt % solution of the composition of Example 35.

FIGS. 35A-C are photographs showing the dissolution behavior of #6 fuel oil in a 20 wt % solution of the composition of Example 37. As shown in FIG. 35A, on initial stirring, the #6 fuel oil did not significant disperse. As shown in FIG. 35B, after aggressive stirring for about 10 seconds, the #6 fuel oil formed small stringers in solution. FIG. 35C is a picture of the bottom of the beaker containing the 5 wt % solution of Example 37 and the #6 fuel oil after aggressive stirring. As can be seen, small stringers of the #6 fuel oil are formed.

Example 41

5 wt %, 10 wt % and 20 wt % solutions of the composition of Example 38 were prepared by admixing 1.5 g, 3 g and 6 g of the composition of Example 37 with 28.5 g, 27 g and 24 g of water, respectively. The pH of each of the solutions was 13.1. Each solution was placed in a glass beaker, and 2 g of #6 fuel oil was added to each solution.

Figure 36A:
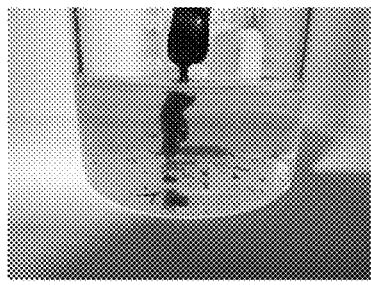
FIGS. 36A-C are photographs showing the dissolution behavior of #6 fuel oil in a 5 wt % solution of the composition of Example 36.
Figure 36B:
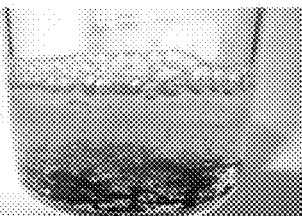
Figure 36C:

FIGS. 36A-C are photographs showing the dissolution behavior of #6 fuel oil in a 5 wt % solution of the composition of Example 38. As shown in FIG. 36A, on initial stirring, the #6 fuel oil formed a few small stringers. As shown in FIG. 36B, after aggressive stirring for about 10 seconds, the #6 fuel oil formed small stringers in solution. FIG. 36C is a picture of the bottom of the beaker containing the 5 wt % solution of Example 38 and the #6 fuel oil after aggressive stirring. As can be seen, small stringers of the #6 fuel oil are formed.

Figure 37A:
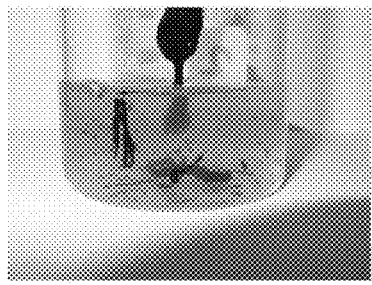
FIGS. 37A-C are photographs showing the dissolution behavior of #6 fuel oil in a 10 wt % solution of the composition of Example 36.
Figure 37B:
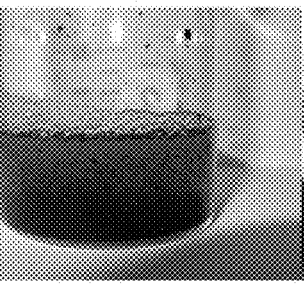
Figure 37C:
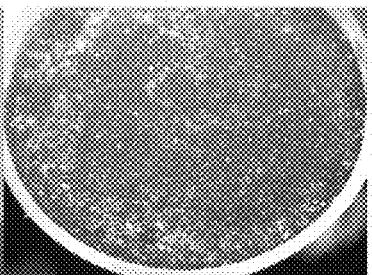

FIGS. 37A-C are photographs showing the dissolution behavior of #6 fuel oil in a 10 wt % solution of the composition of Example 38. As shown in FIG. 37A, on initial stirring, larger stringers of the #6 fuel oil are formed. As shown in FIG. 37B, after aggressive stirring for about 10 seconds, the solution darkened and the #6 fuel oil formed small stringers in solution. FIG. 37C is a photograph of the bottom of the beaker containing the 10 wt % solution of Example 38 and the #6 fuel oil after aggressive stirring. As can be seen, many small stringers of the #6 fuel oil are formed.

Figure 38A:
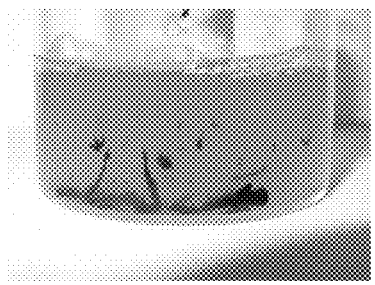
FIGS. 38A-C are photographs showing the dissolution behavior of #6 fuel oil in a 20 wt % solution of the composition of Example 36.
Figure 38B:
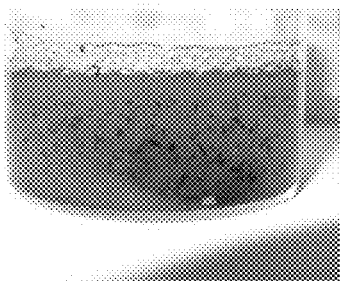
Figure 38C:
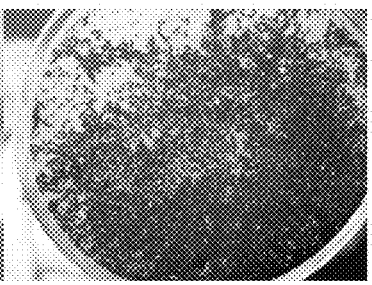

FIGS. 38A-C are photographs showing the dissolution behavior of #6 fuel oil in a 20 wt % solution of the composition of Example 38. As shown in FIG. 38A, on initial stirring, the #6 fuel oil formed large stringers. As shown in FIG. 38B, after aggressive stirring for about 10 seconds, the #6 fuel oil formed small stringers in solution. FIG. 38C is a photograph of the bottom of the beaker containing the 5 wt % solution of Example 38 and the #6 fuel oil after aggressive stirring. As can be seen, small stringers of the #6 fuel oil are formed.

Example 42

A 10 wt % solution of the composition of Example 37 (50 mL) was prepared by admixing 5 g of the composition of Example 37 and 45 g of water. The pH of the solution was 13.1. The solution was placed in a glass beaker, and 5 g of coal tar sand (5% coal tar/95% sand) was added. FIGS. 39, 40A-B and 41A-B are photographs showing the extraction of coal tar from coal tar sand in a 10 wt % solution of the composition of Example 37 over approximately 3 hours and 20 minutes of stirring. FIG. 39 shows that after 10 minutes, no coal tar has been separated from the coal tar sand. FIG. 40A shows that after 1 hour and 21 minutes, some clean sand is present and chunks and stringers of agglomerated coal tar can be seen on top of the sand. FIG. 40B shows the bottom of the beaker at 1 hour and 21 minutes. FIG. 41A shows that after 3 hours and 21 minutes, mostly clean sand is present and larger chunks and stringers of agglomerated coal tar can be seen on top of the sand. FIG. 41B shows the bottom of the beaker at 3 hours and 21 minutes. This Example demonstrates that a Composition of the Invention is effective at extracting coal tar from coal tar sand.

Example 43

A 10 wt % solution of the composition of Example 38 (50 mL) was prepared by admixing 5 g of the composition of Example 38 with 45 g of water. The pH of the solution was 13.1. The solution was placed in a glass beaker, and 5 g of coal tar sand (5% coal tar/95% sand) was added. FIGS. 42, 43A-B and 44A-B are photographs showing the extraction of coal tar from coal tar sand in a 10 wt % solution of the composition of Example 38 over approximately 3 hours and 20 minutes of stirring. FIG. 42 shows that after 10 minutes, no coal tar has been separated from the coal tar sand. FIG. 43A shows that after 1 hour and 21 minutes, some clean sand is present and chunks and stringers of agglomerated coal tar can be seen on top of the sand. FIG. 43B shows the bottom of the beaker at 1 hour and 21 minutes. FIG. 44A shows that after 3 hours and 21 minutes, mostly clean sand is present and larger chunks and stringers of agglomerated coal tar can be seen on top of the sand. FIG. 44B shows the bottom of the beaker at 3 hours and 21 minutes. This Example demonstrates that a Composition of the Invention is effective at extracting coal tar from coal tar sand.

Example 44

A 10 wt % solution of the composition of Example 37 (50 mL) was prepared by admixing 5 g of the composition of Example 37 and 45 g of water. The pH of the solution was 13.1. The solution was placed in a glass beaker, and 5 g of Athabasca oil sand was added. FIGS. 45, 46A-B and 47A-B are photographs showing the extraction of Athabasca oil from Athabasca oil sand in a 10 wt % solution of the composition of Example 37 over approximately 3 hours and 20 minutes of stirring. FIG. 45 shows that after 10 minutes, no oil has been separated from the Athabasca oil sand. FIG. 46A shows that after 1 hour and 21 minutes, very little oil has been extracted from the Athabasca oil sand. FIG. 46B shows the bottom of the beaker at 1 hour and 21 minutes. FIG. 47A shows that after 3 hours and 21 minutes, very little oil has been extracted from the Athabasca oil sand. FIG. 47B shows the bottom of the beaker at 3 hours and 21 minutes.

Example 45

A 10 wt % solution of the composition of Example 38 (50 mL) was prepared by admixing 5 g of the composition of Example 38 and 45 g of water. The pH of the solution was 13.1. The solution was placed in a glass beaker, and 5 g of Athabasca oil sand was added. FIGS. 48, 49A-B and 50A-B are photographs showing the extraction of Athabasca oil from Athabasca oil sand in a 10 wt % solution of the composition of Example 38 over approximately 3 hours and 20 minutes of stirring. FIG. 48 shows that after 10 minutes, no oil has been separated from the Athabasca oil sand. FIG. 49A shows that after 1 hour and 21 minutes, some oil has been extracted from the Athabasca oil sand, oil balls are formed, and clean sand is observed on the bottom of the beaker. FIG. 49B shows the bottom of the beaker at 1 hour and 21 minutes. FIG. 50A shows that after 3 hours and 21 minutes, most of the oil has been extracted from the Athabasca oil sand and some oil balls are formed. FIG. 50B shows the bottom of the beaker at 3 hours and 21 minutes.

Example 46

20 g of a 10 wt % solution of the composition of Example 35 is prepared by combining 18 g water and 2 g of the composition of Example 35. The solution is placed in a glass beaker with 2 g of Phil Wood bicycle grease. 1 drop of polysorbate is added to the mixture, and then d-limonene is added dropwise in increments to the solution, with agitation, to provide increasing ratios of polysorbate to d-limonene of 1:1, 1:2, 1:3, 1:5, 1:7 and 1:10 in the solution. At each ratio of polysorbate to d-limonene, the solution is stirred and observed before adding additional d-limonene.

Example 47

20 g of a 10 wt % solution of the composition of Example 35 is prepared by combining 18 g water and 2 g of the composition of Example 35. The solution is placed in a glass beaker with 2 g of Phil Wood bicycle grease. 20 drops of d-limonene are added to the solution, then polysorbate 80 is then added dropwise in increments to the solution, with agitation, to provide increasing ratios of polysorbate to d-limonene of 1:20, 2:20, 3:20 and 8:20 in the solution. At each ratio of polysorbate to d-limonene, the solution is stirred and observed before adding additional d-limonene.

Example 48

20 g of a 10 wt % solution of the composition of Example 35 is prepared by combining 18 g water and 2 g of the composition of Example 35. The solution is placed in a glass beaker with 2 g of Phil Wood bicycle grease. 10 drops of polysorbate is added to the mixture, and then d-limonene is added dropwise in increments to the solution, with agitation, to provide increasing ratios of polysorbate to d-limonene of 10:1, 10:4, 10:7, 10:13, 10:16 and 10:19 in the solution. At each ratio of polysorbate to d-limonene, the solution is stirred and observed before adding additional d-limonene.

Example 49

20 g of a 10 wt % solution of the composition of Example 35 is prepared by combining 18 g water and 2 g of the composition of Example 35. The solution is placed in a glass beaker with 2 g of #6 fuel oil.

Example 50

20 g of a 10 wt % solution of the composition of Example 35 is prepared by combining 18 g water and 2 g of the composition of Example 35. The solution is placed in a glass beaker. 2 g of #6 fuel oil is combined with 2 g of d-limonene, then added to the 10 wt % solution of the composition of Example 35.

Example 51

20 g of a 10 wt % solution of the composition of Example 35 is prepared by combining 18 g water and 2 g of the composition of Example 35. The solution is placed in a glass beaker with 2 g of coal tar.

Example 52

20 g of a 10 wt % solution of the composition of Example 35 is prepared by combining 18 g water and 2 g of the composition of Example 35. The solution is placed in a glass beaker. 2 g of coal tar is combined with 2 g of d-limonene, then added to the 10 wt % solution of the composition of Example 35.

Example 53

20 g of a 10 wt % solution of the composition of Example 35 is prepared by combining 18 g water and 2 g of the composition of Example 35. The solution is placed in a glass beaker. 5 g of NaCl is added to the 10 wt % solution of the composition of Example 35 and stirred. 2 g of #6 fuel oil is then added and the mixture is stirred and allowed to stand for 2 minutes.

Example 54

20 g of a 10 wt % solution of the composition of Example 35 is prepared by combining 18 g water and 2 g of the composition of Example 35. The solution is placed in a glass beaker. 5 g of sugar is added to the 10 wt % solution of the composition of Example 35 and stirred. 2 g of #6 fuel oil is then added and the mixture is stirred and allowed to stand for 2 minutes.

Example 55

20 g of a 10 wt % solution of the composition of Example 35 is prepared by combining 18 g water and 2 g of the composition of Example 35. The solution is placed in a glass beaker. 5 g of NaOH is added to the 10 wt % solution of the composition of Example 35 and stirred. 2 g of #6 fuel oil is then added and the mixture is stirred and allowed to stand for 2 minutes.

Example 56

20 g of a 10 wt % solution of the composition of Example 35 is prepared by combining 18 g water and 2 g of the composition of Example 35. The solution is placed in a glass beaker. 5 g of NaCl is added to the 10 wt % solution of the composition of Example 35 and stirred. 2 g of coal tar is then added and the mixture is stirred and allowed to stand for 2 minutes.

Example 57

20 g of a 10 wt % solution of the composition of Example 35 is prepared by combining 18 g water and 2 g of the composition of Example 35. The solution is placed in a glass beaker. 5 g of sugar is added to the 10 wt % solution of the composition of Example 35 and stirred. 2 g of coal tar is then added and the mixture is stirred and allowed to stand for 2 minutes.

Example 58

20 g of a 10 wt % solution of the composition of Example 35 is prepared by combining 18 g water and 2 g of the composition of Example 35. The solution is placed in a glass beaker. 5 g of NaOH is added to the 10 wt % solution of the composition of Example 35 and stirred. 2 g of coal tar is then added and the mixture is stirred and allowed to stand for 2 minutes.

Example 59

An illustrative aqueous composition comprising whey, but not comprising polysaccharide other than that present in or derived from the whey, is prepared. Citric acid (1.07 grams) is dissolved in 0.156 kg of 70% isopropanol at about 23° C. Whey powder (0.497 kg) is added, and the resultant mixture is allowed to stir for 2 hours. 0.620 kg of granular sodium hydroxide is added to 2.966 kg of water, the resultant sodium hydroxide solution is added to the isopropanol/hemp mixture, and the resultant mixture is allowed to stand for 6 hours. Sodium chloride (1.98 g) is then added, also with stirring. The resultant mixture is then allowed to stand an additional 2 hours. S-type hydrated lime (19.8 g) is then added with stirring, and the resultant mixture is stirred until uniform. The solids are allowed to settle for 80 hours, and the supernatant is decanted to provide an aqueous composition as the decanted supernatant.

Example 60

20 g of a 10 wt % solution of the composition of Example 59 is prepared by combining 18 g water and 2 g of the composition of Example 59. The solution is placed in a glass beaker with 2 g of coal tar. The solution is stirred for 1 hour.

Example 61

20 g of a 10 wt % solution of the composition of Example 59 is prepared by combining 18 g water and 2 g of the composition of Example 59. The solution is placed in a glass beaker with 2 g of Athabasca oil sand. The solution is stirred for 1 hour.

Example 62

An illustrative aqueous composition comprising tyrosine, but not comprising polysaccharide other than that present in or derived from the whey, is prepared. Citric acid (1.07 grams) is dissolved in 0.156 kg of 70% isopropanol at about 23° C. Tyrosine (0.497 kg) is added, and the resultant mixture is allowed to stir for 2 hours. 0.620 kg of granular sodium hydroxide is added to 2.966 kg of water, the resultant sodium hydroxide solution is added to the isopropanol/hemp mixture, and the resultant mixture is allowed to stand for 6 hours. Sodium chloride (1.98 g) is then added, also with stirring. The resultant mixture is then allowed to stand an additional 2 hours. S-type hydrated lime (19.8 g) is then added with stirring, and the resultant mixture is stirred until uniform. The solids are allowed to settle for 80 hours, and the supernatant is decanted to provide an aqueous composition as the decanted supernatant.

Example 63

20 g of a 10 wt % solution of the composition of Example 62 is prepared by combining 18 g water and 2 g of the composition of Example 62. The solution is placed in a glass beaker with 2 g of coal tar. The solution is stirred for 1 hour.

Example 64

20 g of a 10 wt % solution of the composition of Example 59 is prepared by combining 18 g water and 2 g of the composition of Example 59. The solution is placed in a glass beaker with 2 g of Athabasca oil sand. The solution is stirred for 1 hour. The solution is stirred for 1 hour.

Example 65

20 g of a 10 wt % solution of the composition of Example 35 is prepared by combining 18 g water and 2 g of the composition of Example 35. The solution is placed in a glass beaker. 2 g of #6 fuel oil is combined with 2 g of diesel fuel, then added to the 10 wt % solution of the composition of Example 35.

Example 66

20 g of a 10 wt % solution of the composition of Example 35 is prepared by combining 18 g water and 2 g of the composition of Example 35. The solution is placed in a glass beaker. 2 g of #6 fuel oil is combined with 2 g of biodiesel, then added to the 10 wt % solution of the composition of Example 35.

Example 67

20 g of a 10 wt % solution of the composition of Example 35 is prepared by combining 18 g water and 2 g of the composition of Example 35. The solution is placed in a glass beaker. 2 g of #6 fuel oil is combined with 2 g of hexane, then added to the 10 wt % solution of the composition of Example 35.

Example 68

20 g of a 10 wt % solution of the composition of Example 35 is prepared by combining 18 g water and 2 g of the composition of Example 35. The solution is placed in a glass beaker. 2 g of coal tar is combined with 2 g of diesel fuel, then added to the 10 wt % solution of the composition of Example 35.

Example 69

20 g of a 10 wt % solution of the composition of Example 35 is prepared by combining 18 g water and 2 g of the composition of Example 35. The solution is placed in a glass beaker. 2 g of coal tar is combined with 2 g of biodiesel, then added to the 10 wt % solution of the composition of Example 35.

Example 70

20 g of a 10 wt % solution of the composition of Example 35 is prepared by combining 18 g water and 2 g of the composition of Example 35. The solution is placed in a glass beaker. 2 g of coal tar is combined with 2 g of hexane, then added to the 10 wt % solution of the composition of Example 35.

The embodiments described herein and illustrated by the foregoing examples should be understood to be illustrative of the present invention, and should not be construed as limiting. On the contrary, the present disclosure embraces alternatives and equivalents thereof, as embodied by the appended claims. Each reference disclosed herein is incorporated by reference herein in its entirety.

What is claimed is:

1. A method for extracting a hydrocarbon-containing substance from a substrate, comprising contacting the substrate with an aqueous composition under conditions effective for extracting at least some of the hydrocarbon-containing substance from the substrate, wherein the aqueous composition comprises:
   a mixture obtained by (a) allowing water, corn gluten meal and an inorganic base to (i) stir at about 10° C. to about 100° C. for about 2 hours to about 4 hours or (ii) stand at about 10° C. to about 100° C. for about 10 minutes to about 8 hours, and (b) removing undissolved solids from the mixture;
   0% to about 10 wt % of an alcohol;
   about 0.5 wt % to about 15 wt % of a base;
   0% to about 10 wt % of a salt;
   0% to about 10 wt % of an acid;
   0% to about 10 wt % of an additive; and
   about 10 wt % to about 95 wt % of water;
   wherein
   the aqueous composition has a pH of about 13; and
   the amount of corn gluten meal is about 1 wt % to about 50 wt % of the aqueous composition.

2. The method of claim 1, wherein the substrate is soil, sand, wood, rock, mineral, paper, skin, a waterbody, gravel, mud, clay, plant, hair, fabric, metal, glass, porcelain, plastic, concrete, a living animal or a dead animal.

3. The method of claim 1 wherein the extracting comprises removing the hydrocarbon-containing substance from the surface of the substrate.

4. The method of claim 1, wherein the contacting occurs at an aqueous composition or a substrate temperature of about 5° to about 90° C.

5. The method of claim 1, wherein the method further comprises subjecting the aqueous composition or the substrate to agitation.

6. The method of claim 1, wherein the hydrocarbon-containing substance is grease, crude oil, coal tar, sludge, bitumen, automotive oil, petrolatum, one or more petroleum distillates, diesel fuel, heating oil, jet fuel, aviation gasoline, kerosene, creosote, coal tar sand, tar sand, light tar oil, bitumen, sludge, oil-contaminated sludge or refined products thereof.

7. The method of claim 1, wherein the alcohol is ethanol, methanol, or isopropanol.

8. The method of claim 1, wherein the base is sodium hydroxide, lithium hydroxide, or potassium hydroxide.

9. The method of claim 1, wherein the salt is sodium chloride, sodium nitrate, potassium chloride, calcium chloride, magnesium chloride, ammonium chloride, sodium bromide, potassium bromide, calcium bromide, magnesium bromide, ammonium bromide, sodium iodide, potassium iodide, calcium iodide, magnesium iodide, ammonium iodide, sodium sulfate, potassium sulfate, calcium sulfate, magnesium sulfate, ammonium sulfate or mixtures thereof.

10. The method of claim 1, wherein the acid is citric acid, formic acid, ascorbic acid, acetic acid, malic acid, adipic acid, tannic acid, lactic acid, fumaric acid, or mixtures thereof.

11. The method of claim 1, wherein the additive is lime, a surfactant, or a solvent.

12. The method of claim 11, wherein the solvent is d-limonene, petroleum-derived diesel fuel, biodiesel, or combinations thereof.

13. The method of claim 11, wherein the surfactant is a polysorbate.

14. A method for extracting a hydrocarbon-containing substance from a substrate, comprising contacting the substrate with an extractant under conditions effective for extracting at least some of the hydrocarbon-containing substance from the substrate, wherein the extractant comprises:
   a mixture obtained by (a) allowing water, corn gluten meal and an inorganic base to (i) stir at about 10° C. to about 100° C. for about 2 hours to about 4 hours or (ii) stand at about 10° C. to about 100° C. for about 10 minutes to about 8hours, and (b) removing undissolved solids from the mixture;

0% to about 1 wt % of an alcohol;
about 0.05 wt % to about 15 wt % of a base;
0% to about 1 wt % of a salt;
0% to about 1 wt % of an acid;
0% to about 1 wt % of an additive; and
about 50 wt % to about 95 wt % of water;
wherein
the amount of corn gluten meal is about 0.1 wt % to about 2 wt % of the extractant.

15. The method of claim 14, wherein the substrate is soil, sand, wood, rock, mineral, paper, skin, a waterbody, gravel, mud, clay, plant, hair, fabric, metal, glass, porcelain, plastic, concrete, a living animal or a dead animal.

16. The method of claim 14, wherein the extracting comprises removing the hydrocarbon-containing substance from the surface of the substrate.

17. The method of claim 14, wherein the contacting occurs at an extractant or a substrate temperature of about 5° to about 50° C.

18. The method of claim 14, wherein the method further comprises subjecting the extractant or the substrate to agitation.

19. The method of claim 14, wherein the hydrocarbon-containing substance is crude oil, one or more petroleum distillates, diesel fuel, heating oil, jet fuel, aviation gasoline, kerosene, creosote, coal tar sand, tar sand, light tar oil, bitumen, sludge, oil-contaminated sludge or refined products thereof.

20. The method of claim 14, wherein the alcohol is ethanol, methanol, or isopropanol.

21. The method of claim 14, wherein the base is sodium hydroxide, lithium hydroxide, or potassium hydroxide.

22. The method of claim 14, wherein the salt is sodium chloride, sodium nitrate, potassium chloride, calcium chloride, magnesium chloride, ammonium chloride, sodium bromide, potassium bromide, calcium bromide, magnesium bromide, ammonium bromide, sodium iodide, potassium iodide, calcium iodide, magnesium iodide, ammonium iodide, sodium sulfate, potassium sulfate, calcium sulfate, magnesium sulfate, ammonium sulfate or mixtures thereof.

23. The method of claim 14, wherein the acid is citric acid, formic acid, ascorbic acid, acetic acid, malic acid, adipic acid, tannic acid, lactic acid, fumaric acid, or mixtures thereof.

24. The method of claim 14, wherein the additive is lime, a surfactant, or a solvent.

25. The method of claim 14, wherein the pH of the extractant is from about 9 to about 13.

26. The method of claim 24, wherein the solvent is d-limonene, petroleum-derived diesel fuel, or biodiesel.

27. The method of claim 24, wherein the surfactant is a polysorbate.

28. A method for extracting a hydrocarbon-containing substance from a substrate, comprising hydraulically fracturing the substrate with a hydraulic fracturing fluid comprising an aqueous composition, wherein the aqueous composition comprises:
a mixture obtained by (a) allowing water, corn gluten meal and an inorganic base to (i) stir at about 10° C. to about 100° C. for about 2 hours to about 4 hours or (ii) stand at about 10° C. to about 100° C. for about 10 minutes to about 8 hours, and (b) removing undissolved solids from the mixture;
0% to about 10 wt % of an alcohol;
about 0.5 wt % to about 15 wt % of a base;
0% to about 10 wt % of a salt;
0% to about 10 wt % of an acid;
0% to about 10 wt % of an additive; and
about 10 wt % to about 95 wt % of water;
wherein
the aqueous composition has a pH of about 13; and
the amount of corn gluten meal is about 1 wt % to about 50 wt % of the aqueous composition.

29. The method of claim 28, wherein the alcohol is ethanol, methanol, or isopropanol.

30. The method of claim 28, wherein the base is sodium hydroxide, lithium hydroxide, or potassium hydroxide.

31. The method of claim 28, wherein the salt is sodium chloride, sodium nitrate, potassium chloride, calcium chloride, magnesium chloride, ammonium chloride, sodium bromide, potassium bromide, calcium bromide, magnesium bromide, ammonium bromide, sodium iodide, potassium iodide, calcium iodide, magnesium iodide, ammonium iodide, sodium sulfate, potassium sulfate, calcium sulfate, magnesium sulfate, ammonium sulfate or mixtures thereof.

32. The method of claim 28, wherein the acid is citric acid, formic acid, ascorbic acid, acetic acid, malic acid, adipic acid, tannic acid, lactic acid, fumaric acid, or mixtures thereof.

33. The method of claim 28, wherein the additive is lime, a surfactant, or a solvent.

34. The method of claim 33, wherein the solvent is d-limonene, petroleum-derived diesel fuel, biodiesel, or combinations thereof.

35. The method of claim 33, wherein the surfactant is a polysorbate.

36. A method for extracting a hydrocarbon-containing substance from a substrate, comprising hydraulically fracturing the substrate with a hydraulic fracturing fluid comprising an extractant, wherein the extractant comprises:
a mixture obtained by (a) allowing water, corn gluten meal and an inorganic base to (i) stir at about 10° C. to about 100° C. for about 2 hours to about 4 hours or (ii) stand at about 10° C. to about 100° C. for about 10 minutes to about 8 hours, and (b) removing undissolved solids from the mixture;
0% to about 1 wt % of an alcohol;
about 0.05 wt % to about 15 wt % of a base;
0% to about 1 wt % of a salt;
0% to about 1 wt % of an acid;
0% to about 1 wt % of an additive; and
about 50 wt % to about 95 wt % of water;
wherein
the amount of corn gluten meal is about 0.1 wt % to about 2 wt % of the extractant.

37. The method of claim 36, wherein the alcohol is ethanol, methanol, or isopropanol.

38. The method of claim 36, wherein the base is sodium hydroxide, lithium hydroxide, or potassium hydroxide.

39. The method of claim 36, wherein the salt is sodium chloride, sodium nitrate, potassium chloride, calcium chloride, magnesium chloride, ammonium chloride, sodium bromide, potassium bromide, calcium bromide, magnesium bromide, ammonium bromide, sodium iodide, potassium iodide, calcium iodide, magnesium iodide, ammonium iodide, sodium sulfate, potassium sulfate, calcium sulfate, magnesium sulfate, ammonium sulfate or mixtures thereof.

40. The method of claim 36, wherein the acid is citric acid, formic acid, ascorbic acid, acetic acid, malic acid, adipic acid, tannic acid, lactic acid, fumaric acid, or mixtures thereof.

41. The method of claim 36, wherein the additive is lime, a surfactant, or a solvent.

42. The method of claim 36, wherein the pH of the extractant is from about 9 to about 13.

43. The method of claim 41, wherein the solvent is d-limonene, petroleum-derived diesel fuel, or biodiesel.

44. The method of claim 41, wherein the surfactant is a polysorbate.

45. The method of claim 28, wherein the substrate is soil, sand, wood, rock, mineral, gravel, mud or clay.

46. The method of claim 36, wherein the substrate is soil, sand, wood, rock, mineral, gravel, mud or, clay.

* * * * *

UNITED STATES PATENT AND TRADEMARK OFFICE
CERTIFICATE OF CORRECTION

PATENT NO. : 9,624,437 B2
APPLICATION NO. : 15/187472
DATED : April 18, 2017
INVENTOR(S) : Peter Rehage It is certified that error appears in the above-identified patent and that said Letters Patent is hereby corrected as shown below:

On the Title Page

Under item (71), replace "New York, NY" with --Springfield, MA--.

Under item (73), replace "New York, NY" with --Springfield, MA--.

In the Specification

At Column 7, Line 48, replace "Example 35" with --Example 37--.

At Column 7, Line 51, replace "Example 35" with --Example 37--.

At Column 7, Line 54, replace "Example 35" with --Example 37--.

At Column 7, Line 57, replace "Example 36" with --Example 38--.

At Column 7, Line 60, replace "Example 36" with --Example 38--.

At Column 7, Line 63, replace "Example 36" with --Example 38--.

At Column 8, Line 7, replace "Example 35" with --Example 37--.

At Column 8, Line 11, replace "Example 36" with --Example 38--.

At Column 46, Line 33, replace "wastewaster" with --wastewater--.

At Column 80, Line 39, replace "FIG. 25" with --FIG. 24--.

At Column 91, Lines 16-17, replace "photo-graph" with --line drawing--.

Signed and Sealed this
Ninth Day of January, 2018

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,624,437 B2

At Column 93, Line 13, replace "30A" with --32A--.

At Column 93, Line 21, replace "30D" with --32D--.

At Column 93, Line 28, replace "30D" with --32D--.